United States Patent [19]

Lemischka

[11] Patent Number: 5,621,090
[45] Date of Patent: Apr. 15, 1997

[54] NUCLEIC ACIDS ENCODING SOLUBLE HUMAN FLK-2 EXTRACELLULAR DOMAIN

[75] Inventor: Ihor R. Lemischka, Princeton, N.J.

[73] Assignee: The Trustees of Princeton University, Princeton, N.J.

[21] Appl. No.: 906,397

[22] Filed: Jun. 26, 1992

Related U.S. Application Data

[63] Continuation-in-part of Ser. No. 813,593, Dec. 24, 1991, Pat. No. 5,185,438, which is a continuation-in-part of Ser. No. 793,065, Nov. 15, 1991, abandoned, which is a continuation-in-part of Ser. No. 728,913, Jun. 28, 1991, abandoned, which is a continuation-in-part of Ser. No. 679,666, Apr. 2, 1991, abandoned.

[51] Int. Cl.$^6$ .................................................. C07H 21/00
[52] U.S. Cl. ..................... 536/23.5; 435/69.1; 435/172.1
[58] Field of Search .................... 536/23.5, 23.1; 435/69.1, 172.1, 320.1; 530/350, 403, 387.1, 846; 514/2; 935/10

[56] References Cited

U.S. PATENT DOCUMENTS 5,185,438   2/1993   Lemischka ............................. 536/23.2

OTHER PUBLICATIONS

O. Rosnet et al Oncogene 6:1641 Sep. 1991.
O. Rosnet et al. Genomics 9:380 Feb. 1991.

*Primary Examiner*—Stephen G. Walsh
*Assistant Examiner*—L. Spector
*Attorney, Agent, or Firm*—Irving N. Feit; Eric Sheets; Thomas C. Gallagher

[57] ABSTRACT

Isolated mammalian nucleic acid molecules encoding receptor protein tyrosine kinases expressed in primitive hematopoietic cells and not expressed in mature hematopoietic cells are provided. Also included are the receptors encoded by such nucleic acid molecules; the nucleic acid molecules encoding receptor protein tyrosine kinases having the sequences shown in FIG. 1A (murine flk-2), FIG. 1B (human flk-2) and FIG. 2 (murine flk-1); the receptor protein tyrosine kinases having the amino acid sequences shown in FIG. 1A, FIG. 1B and FIG. 2; ligands for the receptors; nucleic acid sequences that encode the ligands; and methods of stimulating the proliferation and/or differentiation of primitive mammalian hematopoietic stem cells comprising contacting the stem cells with a ligand that binds to a receptor protein tyrosine kinase expressed in primitive mammalian hematopoietic cells and not expressed in mature hematopoietic cells.

2 Claims, 22 Drawing Sheets

FIGURE 1A-1

```
GCGGCCTGGC TACCGCGCGC TCCGGACGCC ATG CGG GCG TTG GCG CAG CGC AGC
                                     Met Arg Ala Leu Ala Gln Arg Ser
                                      1                5

GAC CGG CGG CTG CTG CTG CTT GTT GTT TTG TCA GTA ATG ATT CTT GAG
Asp Arg Arg Leu Leu Leu Leu Val Val Leu Ser Val Met Ile Leu Glu
     10              15                  20

ACC GTT ACA AAC CAA GAC CTG CCT GTG ATC AAG TGT GTT TTA ATC AGT
Thr Val Thr Asn Gln Asp Leu Pro Val Ile Lys Cys Val Leu Ile Ser
 25              30              35                          40

CAT GAG AAC AAT GGC TCA TCA GCG GGA AAG CCA TCA TCG TAC CGA ATG
His Glu Asn Asn Gly Ser Ser Ala Gly Lys Pro Ser Ser Tyr Arg Met
             45              50                      55

GTG CGA GGA TCC CCA GAA GAC CTC CAG TGT ACC CCG AGG CGC CAG AGT
Val Arg Gly Ser Pro Glu Asp Leu Gln Cys Thr Pro Arg Arg Gln Ser
             60              65                  70

GAA GGG ACG GTA TAT GAA GCG GCC ACC GTG GAG GTG GCC GAG TCT GGG
Glu Gly Thr Val Tyr Glu Ala Ala Thr Val Glu Val Ala Glu Ser Gly
         75              80                  85

TCC ATC ACC CTG CAA GTG CAG CTC GCC ACC CCA GGG GAC CTT TCC TGC
Ser Ile Thr Leu Gln Val Gln Leu Ala Thr Pro Gly Asp Leu Ser Cys
     90              95                  100

CTC TGG GTC TTT AAG CAC AGC TCC CTG GGC TGC CAG CCG CAC TTT GAT
Leu Trp Val Phe Lys His Ser Ser Leu Gly Cys Gln Pro His Phe Asp
105                  110                 115                 120

TTA CAA AAC AGA GGA ATC GTT TCC ATG GCC ATC TTG AAC GTG ACA GAG
Leu Gln Asn Arg Gly Ile Val Ser Met Ala Ile Leu Asn Val Thr Glu
                 125             130                 135

ACC CAG GCA GGA GAA TAC CTA CTC CAT ATT CAG AGC GAA CGC GCC AAC
Thr Gln Ala Gly Glu Tyr Leu Leu His Ile Gln Ser Glu Arg Ala Asn
             140             145                 150

TAC ACA GTA CTG TTC ACA GTG AAT GTA AGA GAT ACA CAG CTG TAT GTG
Tyr Thr Val Leu Phe Thr Val Asn Val Arg Asp Thr Gln Leu Tyr Val
         155             160             165

CTA AGG AGA CCT TAC TTT AGG AAG ATG GAA AAC CAG GAT GCA CTG CTC
Leu Arg Arg Pro Tyr Phe Arg Lys Met Glu Asn Gln Asp Ala Leu Leu
     170             175                 180
```

FIGURE 1A-2

```
TGC ATC TCC GAG GGT GTT CCG GAG CCC ACT GTG GAG TGG GTG CTC TGC
Cys Ile Ser Glu Gly Val Pro Glu Pro Thr Val Glu Trp Val Leu Cys
185             190             195             200

AGC TCC CAC AGG GAA AGC TGT AAA GAA GAA GGC CCT GCT GTT GTC AGA
Ser Ser His Arg Glu Ser Cys Lys Glu Glu Gly Pro Ala Val Val Arg
                205             210             215

AAG GAG GAA AAG GTA CTT CAT GAG TTG TTC GGA ACA GAC ATC AGA TGC
Lys Glu Glu Lys Val Leu His Glu Leu Phe Gly Thr Asp Ile Arg Cys
            220             225             230

TGT GCT AGA AAT GCA CTG GGC CGC GAA TGC ACC AAG CTG TTC ACC ATA
Cys Ala Arg Asn Ala Leu Gly Arg Glu Cys Thr Lys Leu Phe Thr Ile
        235             240             245

GAT CTA AAC CAG GCT CCT CAG AGC ACA CTG CCC CAG TTA TTC CTG AAA
Asp Leu Asn Gln Ala Pro Gln Ser Thr Leu Pro Gln Leu Phe Leu Lys
    250             255             260

GTG GGG GAA CCC TTG TGG ATC AGG TGT AAG GCC ATC CAT GTG AAC CAT
Val Gly Glu Pro Leu Trp Ile Arg Cys Lys Ala Ile His Val Asn His
265             270             275             280

GGA TTC GGG CTC ACC TGG GAG CTG GAA GAC AAA GCC CTG GAG GAG GGC
Gly Phe Gly Leu Thr Trp Glu Leu Glu Asp Lys Ala Leu Glu Glu Gly
                285             290             295

AGC TAC TTT GAG ATG AGT ACC TAC TCC ACA AAC AGG ACC ATG ATT CGG
Ser Tyr Phe Glu Met Ser Thr Tyr Ser Thr Asn Arg Thr Met Ile Arg
            300             305             310

ATT CTC TTG GCC TTT GTG TCT TCC GTG GGA AGG AAC GAC ACC GGA TAT
Ile Leu Leu Ala Phe Val Ser Ser Val Gly Arg Asn Asp Thr Gly Tyr
        315             320             325

TAC ACC TGC TCT TCC TCA AAG CAC CCC AGC CAG TCA GCG TTG GTG ACC
Tyr Thr Cys Ser Ser Ser Lys His Pro Ser Gln Ser Ala Leu Val Thr
    330             335             340

ATC CTA GAA AAA GGG TTT ATA AAC GCT ACC AGC TCG CAA GAA GAG TAT
Ile Leu Glu Lys Gly Phe Ile Asn Ala Thr Ser Ser Gln Glu Glu Tyr
345             350             355             360

GAA ATT GAC CCG TAC GAA AAG TTC TGC TTC TCA GTC AGG TTT AAA GCG
Glu Ile Asp Pro Tyr Glu Lys Phe Cys Phe Ser Val Arg Phe Lys Ala
                365             370             375
```

FIGURE 1A-3

```
TAC CCA CGA ATC CGA TGC ACG TCG ATC TTC TCT CAA GCC TCA TTT CCT
Tyr Pro Arg Ile Arg Cys Thr Trp Ile Phe Ser Gln Ala Ser Phe Pro
            380             385                 390

TGT GAA CAG AGA GGC CTG GAG GAT GGG TAC AGC ATA TCT AAA TTT TGC
Cys Glu Gln Arg Gly Leu Glu Asp Gly Tyr Ser Ile Ser Lys Phe Cys
        395                 400                 405

GAT CAT AAG AAC AAG CCA GGA GAG TAC ATA TTC TAT GCA GAA AAT GAT
Asp His Lys Asn Lys Pro Gly Glu Tyr Ile Phe Tyr Ala Glu Asn Asp
    410                 415                 420

GAC GCC CAG TTC ACC AAA ATG TTC ACG CTG AAT ATA AGA AAG AAA CCT
Asp Ala Gln Phe Thr Lys Met Phe Thr Leu Asn Ile Arg Lys Lys Pro
425                 430                 435                 440

CAA GTG CTA GCA AAT GCC TCA GCC AGC CAG GCG TCC TGT TCC TCT GAT
Gln Val Leu Ala Asn Ala Ser Ala Ser Gln Ala Ser Cys Ser Ser Asp
                445                 450                 455

GGC TAC CCG CTA CCC TCT TGG ACC TGG AAG AAG TGT TCG GAC AAA TCT
Gly Tyr Pro Leu Pro Ser Trp Thr Trp Lys Lys Cys Ser Asp Lys Ser
            460                 465                 470

CCC AAT TGC ACG GAG GAA ATC CCA GAA GGA GTT TGG AAT AAA AAG GCT
Pro Asn Cys Thr Glu Glu Ile Pro Glu Gly Val Trp Asn Lys Lys Ala
        475                 480                 485

AAC AGA AAA GTG TTT GGC CAG TGG GTG TCG AGC AGT ACT CTA AAT ATG
Asn Arg Lys Val Phe Gly Gln Trp Val Ser Ser Ser Thr Leu Asn Met
    490                 495                 500

AGT GAG GCC GGG AAA GGG CTT CTG GTC AAA TGC TGT GCG TAC AAT TCT
Ser Glu Ala Gly Lys Gly Leu Leu Val Lys Cys Cys Ala Tyr Asn Ser
505                 510                 515                 520

ATG GGC ACG TCT TGC GAA ACC ATC TTT TTA AAC TCA CCA GGC CCC TTC
Met Gly Thr Ser Cys Glu Thr Ile Phe Leu Asn Ser Pro Gly Pro Phe
                525                 530                 535

CCT TTC ATC CAA GAC AAC ATC TCC TTT TAT GCG ACC ATT GGG CTC TGT
Pro Phe Ile Gln Asp Asn Ile Ser Phe Tyr Ala Thr Ile Gly Leu Cys
            540                 545                 550

CTC CCC TTC ATT GTT GTT CTC ATT GTG TTG ATC TGC CAC AAA TAC AAA
Leu Pro Phe Ile Val Val Leu Ile Val Leu Ile Cys His Lys Tyr Lys
            555                 560                 565
```

FIGURE 1A-4

```
AAG CAA TTT AGG TAC GAG AGT CAG CTG CAG ATG ATC CAG GTG ACT GGC
Lys Gln Phe Arg Tyr Glu Ser Gln Leu Gln Met Ile Gln Val Thr Gly
    570                 575                 580

CCC CTG GAT AAC GAG TAC TTC TAC GTT GAC TTC AGG GAC TAT GAA TAT
Pro Leu Asp Asn Glu Tyr Phe Tyr Val Asp Phe Arg Asp Tyr Glu Tyr
585                 590                 595                 600

GAC CTT AAG TGG GAG TTC CCG AGA GAG AAC TTA GAG TTT GGG AAG GTC
Asp Leu Lys Trp Glu Phe Pro Arg Glu Asn Leu Glu Phe Gly Lys Val
                605                 610                 615

CTG GGG TCT GGC GCT TTC GGG AGG GTG ATG AAC GCC ACG GCC TAT GGC
Leu Gly Ser Gly Ala Phe Gly Arg Val Met Asn Ala Thr Ala Tyr Gly
                620                 625                 630

ATT AGT AAA ACG GGA GTC TCA ATT CAG GTG GCG GTG AAG ATG CTA AAA
Ile Ser Lys Thr Gly Val Ser Ile Gln Val Ala Val Lys Met Leu Lys
            635                 640                 645

GAG AAA GCT GAC AGC TGT GAA AAA GAA GCT CTC ATG TCG GAG CTC AAA
Glu Lys Ala Asp Ser Cys Glu Lys Glu Ala Leu Met Ser Glu Leu Lys
    650                 655                 660

ATG ATG ACC CAC CTG GGA CAC CAT GAC AAC ATC GTG AAT CTG CTG GGG
Met Met Thr His Leu Gly His His Asp Asn Ile Val Asn Leu Leu Gly
665                 670                 675                 680

GCA TGC ACA CTG TCA GGG CCA GTG TAC TTG ATT TTT GAA TAT TGT TGC
Ala Cys Thr Leu Ser Gly Pro Val Tyr Leu Ile Phe Glu Tyr Cys Cys
                685                 690                 695

TAT GGT GAC CTC CTC AAC TAC CTA AGA AGT AAA AGA GAG AAG TTT CAC
Tyr Gly Asp Leu Leu Asn Tyr Leu Arg Ser Lys Arg Glu Lys Phe His
                700                 705                 710

AGG ACA TGG ACA GAG ATT TTT AAG GAA CAT AAT TTC AGT TCT TAC CCT
Arg Thr Trp Thr Glu Ile Phe Lys Glu His Asn Phe Ser Ser Tyr Pro
            715                 720                 725

ACT TTC CAG GCA CAT TCA AAT TCC AGC ATG CCT GGT TCA CGA GAA GTT
Thr Phe Gln Ala His Ser Asn Ser Ser Met Pro Gly Ser Arg Glu Val
    730                 735                 740

CAG TTA CAC CCG CCC TTG GAT CAG CTC TCA GGG TTC AAT GGG AAT TCA
Gln Leu His Pro Pro Leu Asp Gln Leu Ser Gly Phe Asn Gly Asn Ser
745                 750                 755                 760
```

FIGURE 1A-5

```
ATT CAT TCT GAA GAT GAG ATT GAA TAT GAA AAC CAG AAG AGG CTG GCA
Ile His Ser Glu Asp Glu Ile Glu Tyr Glu Asn Gln Lys Arg Leu Ala
            765             770                 775

GAA GAA GAG GAG GAA GAT TTG AAC GTG CTG ACG TTT GAA GAC CTC CTT
Glu Glu Glu Glu Glu Asp Leu Asn Val Leu Thr Phe Glu Asp Leu Leu
            780             785                 790

TGC TTT GCG TAC CAA GTG GCC AAA GGC ATG GAA TTC CTG GAG TTC AAG
Cys Phe Ala Tyr Gln Val Ala Lys Gly Met Glu Phe Leu Glu Phe Lys
            795             800                 805

TCG TGT GTC CAC AGA GAC CTG GCA GCC AGG AAT GTG TTG GTC ACC CAC
Ser Cys Val His Arg Asp Leu Ala Ala Arg Asn Val Leu Val Thr His
    810             815                 820

GGG AAG GTG GTG AAG ATC TGT GAC TTT GGA CTG GCC CGA GAC ATC CTG
Gly Lys Val Val Lys Ile Cys Asp Phe Gly Leu Ala Arg Asp Ile Leu
825             830                 835                 840

AGC GAC TCC AGC TAC GTC GTC AGG GGC AAC GCA CGG CTG CCG GTG AAG
Ser Asp Ser Ser Tyr Val Val Arg Gly Asn Ala Arg Leu Pro Val Lys
            845             850                 855

TGG ATG GCA CCC GAG AGC TTA TTT GAA GGG ATC TAC ACA ATC AAG AGT
Trp Met Ala Pro Glu Ser Leu Phe Glu Gly Ile Tyr Thr Ile Lys Ser
            860             865                 870

GAC GTC TGG TCC TAC GGC ATC CTT CTC TGG GAG ATA TTT TCA CTG GGT
Asp Val Trp Ser Tyr Gly Ile Leu Leu Trp Glu Ile Phe Ser Leu Gly
            875             880                 885

GTG AAC CCT TAC CCT GGC ATT CCT GTC GAC GCT AAC TTC TAT AAA CTG
Val Asn Pro Tyr Pro Gly Ile Pro Val Asp Ala Asn Phe Tyr Lys Leu
            890             895                 900

ATT CAG AGT GGA TTT AAA ATG GAG CAG CCA TTC TAT GCC ACA GAA GGG
Ile Gln Ser Gly Phe Lys Met Glu Gln Pro Phe Tyr Ala Thr Glu Gly
905             910                 915                 920

ATA TAC TTT GTA ATG CAA TCC TGC TGG GCT TTT GAC TCA AGG AAG CGG
Ile Tyr Phe Val Met Gln Ser Cys Trp Ala Phe Asp Ser Arg Lys Arg
            925             930                 935

CCA TCC TTC CCC AAC CTG ACT TCA TTT TTA GGA TGT CAG CTG GCA GAG
Pro Ser Phe Pro Asn Leu Thr Ser Phe Leu Gly Cys Gln Leu Ala Glu
            940             945                 950
```

FIGURE 1A-6

```
GCA GAA GAA GCA TGT ATC AGA ACA TCC ATC CAT CTA CCA AAA CAG GCG
Ala Glu Glu Ala Cys Ile Arg Thr Ser Ile His Leu Pro Lys Gln Ala
        955                 960                 965

GCC CCT CAG CAG AGA GGC GGG CTC AGA GCC CAG TCG CCA CAG CGC CAG
Ala Pro Gln Gln Arg Gly Gly Leu Arg Ala Gln Ser Pro Gln Arg Gln
        970                 975                 980

GTG AAG ATT CAC AGA GAA AGA AGT TAGCGAGGAG GCCTTGGACC CCGCCACCCT
Val Lys Ile His Arg Glu Arg Ser
985                 990
```

AGCAGGCTGT AGACCGCAGA GCCAAGATTA GCCTCGCCTC TGAGGAAGCG CCCTACAGCG

CGTTGCTTCG CTGGACTTTT CTCTAGATGC TGTCTGCCAT TACTCCAAAG TGACTTCTAT

AAAATCAAAC CTCTCCTCGC ACAGGCCGCA GAGCCAATAA TGAGACTTGT TGGTGAGCCC

GCCTACCCTG GGGGCCTTTC CACGAGCTTG AGGGAAAGC CATGTATCTG AAATATAGTA

TATTCTTGTA AATACGTGAA ACAAACCAAA CCCGTTTTTT GCTAAGGGAA AGCTAAATAT

GATTTTTAAA AATCTATGTT TTAAAATACT ATGTAACTTT TTCATCTATT TAGTGATATA

TTTTATGGAT GGAAATAAAC TTTCTACTGT AAAAAAAAAA AAAAAAAAAA AAAAAA

FIGURE 1B-1

```
CGAGGCGGCA TCCGAGGGCT GGGCCGGCGC CCTGGGGGAC CCCGGGCTCC

GGAGGCC ATG CCG GCG TTG GCG CGC GAC GCG GGC ACC GTG CCG CTG
            Met Pro Ala Leu Ala Arg Asp Ala Gly Thr Val Pro Leu
            1                 5                   10

CTC GTT GTT TTT TCT GCA ATG ATA TTT GGG ACT ATT ACA AAT CAA GAT
Leu Val Val Phe Ser Ala Met Ile Phe Gly Thr Ile Thr Asn Gln Asp
    15                  20                  25

CTG CCT GTG ATC AAG TGT GTT TTA ATC AAT CAT AAG AAC AAT GAT TCA
Leu Pro Val Ile Lys Cys Val Leu Ile Asn His Lys Asn Asn Asp Ser
30              35                  40                      45

TCA GTG GGG AAG TCA TCA TCA TAT CCC ATG GTA TCA GAA TCC CCG GAA
Ser Val Gly Lys Ser Ser Ser Tyr Pro Met Val Ser Glu Ser Pro Glu
                50                  55                  60

GAC CTC GGG TGT GCG TTG AGA CCC CAG AGC TCA GGG ACA GTG TAC GAA
Asp Leu Gly Cys Ala Leu Arg Pro Gln Ser Ser Gly Thr Val Tyr Glu
                65                  70                  75

GCT GCC GCT GTG GAA GTG GAT GTA TCT GCT TCC ATC ACA CTG CAA GTG
Ala Ala Ala Val Glu Val Asp Val Ser Ala Ser Ile Thr Leu Gln Val
            80                  85                  90

CTG GTC GAT GCC CCA GGG AAC ATT TCC TGT CTC TGG GTC TTT AAG CAC
Leu Val Asp Ala Pro Gly Asn Ile Ser Cys Leu Trp Val Phe Lys His
    95                  100                 105

AGC TCC CTG AAT TGC CAG CCA CAT TTT GAT TTA CAA AAC AGA GGA GTT
Ser Ser Leu Asn Cys Gln Pro His Phe Asp Leu Gln Asn Arg Gly Val
110             115                 120                     125

GTT TCC ATG GTC ATT TTG AAA ATG ACA GAA ACC CAA GCT GGA GAA TAC
Val Ser Met Val Ile Leu Lys Met Thr Glu Thr Gln Ala Gly Glu Tyr
                130                 135                 140

CTA CTT TTT ATT CAG AGT GAA GCT ACC AAT TAC ACA ATA TTG TTT ACA
Leu Leu Phe Ile Gln Ser Glu Ala Thr Asn Tyr Thr Ile Leu Phe Thr
            145                     150                 155

GTG AGT ATA AGA AAT ACC CTG CTT TAC ACA TTA AGA AGA CCT TAC TTT
Val Ser Ile Arg Asn Thr Leu Leu Tyr Thr Leu Arg Arg Pro Tyr Phe
            160                 165                 170
```

FIGURE 1B-2

```
AGA AAA ATG GAA AAC CAG GAC GCC CTG GTC TGC ATA TCT GAG AGC GTT
Arg Lys Met Glu Asn Gln Asp Ala Leu Val Cys Ile Ser Glu Ser Val
    175             180                 185

CCA GAG CCG ATC GTG GAA TGG GTG CTT TGC GAT TCA CAG GGG GAA AGC
Pro Glu Pro Ile Val Glu Trp Val Leu Cys Asp Ser Gln Gly Glu Ser
190             195                 200                 205

TGT AAA GAA GAA AGT CCA GCT GTT GTT AAA AAG GAG GAA AAA GTG CTT
Cys Lys Glu Glu Ser Pro Ala Val Val Lys Lys Glu Glu Lys Val Leu
                210             215                 220

CAT GAA TTA TTT GGG ACG GAC ATA AGG TGC TGT GCC AGA AAT GAA CTG
His Glu Leu Phe Gly Thr Asp Ile Arg Cys Cys Ala Arg Asn Glu Leu
                225             230                 235

GGC AGG GAA TGC ACC AGG CTG TTC ACA ATA GAT CTA AAT CAA ACT CCT
Gly Arg Glu Cys Thr Arg Leu Phe Thr Ile Asp Leu Asn Gln Thr Pro
            240             245             250

CAG ACC ACA TTG CCA CAA TTA TTT CTT AAA GTA GGG GAA CCC TTA TGG
Gln Thr Thr Leu Pro Gln Leu Phe Leu Lys Val Gly Glu Pro Leu Trp
    255             260                 265

ATA AGG TGC AAA GCT GTT CAT GTG AAC CAT GGA TTC GGG CTC ACC TGG
Ile Arg Cys Lys Ala Val His Val Asn His Gly Phe Gly Leu Thr Trp
270             275                 280                 285

GAA TTA GAA AAC AAA GCA CTC GAG GAG GGC AAC TAC TTT GAG ATG AGT
Glu Leu Glu Asn Lys Ala Leu Glu Glu Gly Asn Tyr Phe Glu Met Ser
                290             295                 300

ACC TAT TCA ACA AAC AGA ACT ATG ATA CGG ATT CTG TTT GCT TTT GTA
Thr Tyr Ser Thr Asn Arg Thr Met Ile Arg Ile Leu Phe Ala Phe Val
            305             310                 315

TCA TCA GTG GCA AGA AAC GAC ACC GGA TAC TAC ACT TGT TCC TCT TCA
Ser Ser Val Ala Arg Asn Asp Thr Gly Tyr Tyr Thr Cys Ser Ser Ser
            320             325             330

AAG CAT CCC AGT CAA TCA GCT TTG GTT ACC ATC GTA GGA AAG GGA TTT
Lys His Pro Ser Gln Ser Ala Leu Val Thr Ile Val Gly Lys Gly Phe
    335             340                 345

ATA AAT GCT ACC AAT TCA AGT GAA CAT TAT GAA ATT GAC CAA TAT GAA
Ile Asn Ala Thr Asn Ser Ser Glu Asp Tyr Glu Ile Asp Gln Tyr Glu
350             355             360                 365
```

FIGURE 1B-3

```
GAG TTT TGT TTT TCT GTC AGG TTT AAA GCC TAC CCA CAA ATC AGA TGT
Glu Phe Cys Phe Ser Val Arg Phe Lys Ala Tyr Pro Gln Ile Arg Cys
            370             375                         380

ACG TGG ACC TTC TCT CGA AAA TCA TTT CCT TGT GAG CAA AAG GGT CTT
Thr Trp Thr Phe Ser Arg Lys Ser Phe Pro Cys Glu Gln Lys Gly Leu
            385             390                         395

GAT AAC GGA TAC AGC ATA TCC AAG TTT TGC AAT CAT AAG CAC CAG CCA
Asp Asn Gly Tyr Ser Ile Ser Lys Phe Cys Asn His Lys His Gln Pro
            400             405                         410

GGA GAA TAT ATA TTC CAT GCA GAA AAT GAT GAT GCC CAA TTT ACC AAA
Gly Glu Tyr Ile Phe His Ala Glu Asn Asp Asp Ala Gln Phe Thr Lys
    415                 420                     425

ATG TTC ACG CTG AAT ATA AGA AGG AAA CCT CAA GTG CTC GCA GAA GCA
Met Phe Thr Leu Asn Ile Arg Arg Lys Pro Gln Val Leu Ala Glu Ala
430                     435                 440                 445

TCG GCA AGT CAG GCG TCC TGT TTC TCG GAT GGA TAC CCA TTA CCA TCT
Ser Ala Ser Gln Ala Ser Cys Phe Ser Asp Gly Tyr Pro Leu Pro Ser
            450                 455                     460

TGG ACC TGG AAG AAG TGT TCA GAC AAG TCT CCC AAC TGC ACA GAA GAG
Trp Thr Trp Lys Lys Cys Ser Asp Lys Ser Pro Asn Cys Thr Glu Glu
            465                 470                     475

ATC ACA GAA GGA GTC TGG AAT AGA AAG GCT AAC AGA AAA GTG TTT GGA
Ile Thr Glu Gly Val Trp Asn Arg Lys Ala Asn Arg Lys Val Phe Gly
        480                 485                     490

CAG TGG GTG TCG AGC AGT ACT CTA AAC ATG AGT GAA GCC ATA AAA GGG
Gln Trp Val Ser Ser Ser Thr Leu Asn Met Ser Glu Ala Ile Lys Gly
    495                 500                     505

TTC CTG GTC AAG TGC TGT GCA TAC AAT TCC CTT GGC ACA TCT TGT GAG
Phe Leu Val Lys Cys Cys Ala Tyr Asn Ser Leu Gly Thr Ser Cys Glu
510                 515                 520                 525

ACG ATC CTT TTA AAC TCT CCA GGC CCC TTC CCT TTC ATC CAA GAC AAC
Thr Ile Leu Leu Asn Ser Pro Gly Pro Phe Pro Phe Ile Gln Asp Asn
            530                 535                     540

ATC TCA TTC TAT GCA ACA ATT GGT GTT TGT CTC CTC TTC ATT GTC GTT
Ile Ser Phe Tyr Ala Thr Ile Gly Val Cys Leu Leu Phe Ile Val Val
            545                 550                     555
```

FIGURE 1B-4

```
TTA ACC CTG CTA ATT TGT CAC AAG TAC AAA AAG CAA TTT AGG TAT GAA
Leu Thr Leu Leu Ile Cys His Lys Tyr Lys Lys Gln Phe Arg Tyr Glu
    560             565             570

AGC CAG CTA CAG ATG GTA CAG GTG ACC GGC TCC TCA GAT AAT GAG TAC
Ser Gln Leu Gln Met Val Gln Val Thr Gly Ser Ser Asp Asn Glu Tyr
575             580             585

TTC TAC GTT GAT TTC AGA GAA TAT GAA TAT GAT CTC AAA TGG GAG TTT
Phe Tyr Val Asp Phe Arg Glu Tyr Glu Tyr Asp Leu Lys Trp Glu Phe
590             595             600             605

CCA AGA GAA AAT TTA GAG TTT GGG AAG GTA CTA GGA TCA GGT GCT TTT
Pro Arg Glu Asn Leu Glu Phe Gly Lys Val Leu Gly Ser Gly Ala Phe
            610             615             620

GGA AAA GTG ATG AAC GCA ACA GCT TAT GGA ATT AGC AAA ACA GGA GTC
Gly Lys Val Met Asn Ala Thr Ala Tyr Gly Ile Ser Lys Thr Gly Val
            625             630             635

TCA ATC CAG GTT GCC GTC AAA ATG CTG AAA GAA AAA GCA GAC AGC TCT
Ser Ile Gln Val Ala Val Lys Met Leu Lys Glu Lys Ala Asp Ser Ser
            640             645             650

GAA AGA GAG GCA CTC ATG TCA GAA CTC AAG ATG ATG ACC CAG CTG GGA
Glu Arg Glu Ala Leu Met Ser Glu Leu Lys Met Met Thr Gln Leu Gly
    655             660             665

AGC CAC GAG AAT ATT GTG AAC CTG CTG GGG GCG TGC ACA CTG TCA GGA
Ser His Glu Asn Ile Val Asn Leu Leu Gly Ala Cys Thr Leu Ser Gly
670             675             680             685

CCA ATT TAC TTG ATT TTT GAA TAC TGT TGC TAT GGT GAT CTT CTC AAC
Pro Ile Tyr Leu Ile Phe Glu Tyr Cys Cys Tyr Gly Asp Leu Leu Asn
            690             695             700

TAT CTA AGA AGT AAA AGA GAA AAA TTT CAC AGG ACT TGG ACA GAG ATT
Tyr Leu Arg Ser Lys Arg Glu Lys Phe His Arg Thr Trp Thr Glu Ile
            705             710             715

TTC AAG GAA CAC AAT TTC AGT TTT TAC CCC ACT TTC CAA TCA CAT CCA
Phe Lys Glu His Asn Phe Ser Phe Tyr Pro Thr Phe Gln Ser His Pro
        720             725             730

AAT TCC AGC ATG CCT GGT TCA AGA GAA GTT CAG ATA CAC CCG GAC TCG
Asn Ser Ser Met Pro Gly Ser Arg Glu Val Gln Ile His Pro Asp Ser
    735             740             745
```

FIGURE 1B-5

```
GAT CAA ATC TCA GGG CTT CAT GGG AAT TCA TTT CAC TCT GAA GAT GAA
Asp Gln Ile Ser Gly Leu His Gly Asn Ser Phe His Ser Glu Asp Glu
750             755             760             765

ATT GAA TAT GAA AAC CAA AAA AGG CTG GAA GAA GAG GAG GAC TTG AAT
Ile Glu Tyr Glu Asn Gln Lys Arg Leu Glu Glu Glu Glu Asp Leu Asn
            770             775             780

GTG CTT ACA TTT GAA GAT CTT CTT TGC TTT GCA TAT CAA GTT GCC AAA
Val Leu Thr Phe Glu Asp Leu Leu Cys Phe Ala Tyr Gln Val Ala Lys
                785             790             795

GGA ATG GAA TTT CTG GAA TTT AAG TCG TGT GTT CAC AGA GAC CTG GCC
Gly Met Glu Phe Leu Glu Phe Lys Ser Cys Val His Arg Asp Leu Ala
            800             805             810

GCC AGG AAC GTG CTT GTC ACC CAC GGG AAA GTG GTG AAG ATA TGT GAC
Ala Arg Asn Val Leu Val Thr His Gly Lys Val Val Lys Ile Cys Asp
        815             820             825

TTT GGA TTG GCT CGA GAT ATC ATG AGT GAT TCC AAC TAT GTT GTC AGG
Phe Gly Leu Ala Arg Asp Ile Met Ser Asp Ser Asn Tyr Val Val Arg
830             835             840             845

GGC AAT GCC CGT CTG CCT GTA AAA TGG ATG GCC CCC GAA AGC CTG TTT
Gly Asn Ala Arg Leu Pro Val Lys Trp Met Ala Pro Glu Ser Leu Phe
            850             855             860

GAA GGC ATC TAC ACC ATT AAG AGT GAT GTC TGG TCA TAT GGA ATA TTA
Glu Gly Ile Tyr Thr Ile Lys Ser Asp Val Trp Ser Tyr Gly Ile Leu
            865             870             875

CTG TGG GAA ATC TTC TCA CTT GGT GTG AAT CCT TAC CCT GGC ATT CCG
Leu Trp Glu Ile Phe Ser Leu Gly Val Asn Pro Tyr Pro Gly Ile Pro
            880             885             890

GTT GAT GCT AAC TTC TAC AAA CTG ATT CAA AAT GGA TTT AAA ATG GAT
Val Asp Ala Asn Phe Tyr Lys Leu Ile Gln Asn Gly Phe Lys Met Asp
    895             900             905

CAG CCA TTT TAT GCT ACA GAA GAA ATA TAC ATT ATA ATG CAA TCC TGC
Gln Pro Phe Tyr Ala Thr Glu Glu Ile Tyr Ile Ile Met Gln Ser Cys
910             915             920             925

TGG GCT TTT GAC TCA AGG AAA CGG CCA TCC TTC CCT AAT TTG ACT TCG
Trp Ala Phe Asp Ser Arg Lys Arg Pro Ser Phe Pro Asn Leu Thr Ser
            930             935             940
```

FIGURE 1B-6

```
TTT TTA GGA TGT CAG CTG GCA GAT GCA GAA GAA GCG ATG TAT CAG AAT
Phe Leu Gly Cys Gln Leu Ala Asp Ala Glu Glu Ala Met Tyr Gln Asn
            945             950             955

GTG GAT GGC CGT GTT TCG GAA TGT CCT CAC ACC TAC CAA AAC AGG CGA
Val Asp Gly Arg Val Ser Glu Cys Pro His Thr Tyr Gln Asn Arg Arg
            960             965             970

CCT TTC AGC AGA GAG ATG GAT TTG GGG CTA CTC TCT CCG CAG GCT CAG
Pro Phe Ser Arg Glu Met Asp Leu Gly Leu Leu Ser Pro Gln Ala Gln
            975             980             985

GTC GAA GAT TCG TAG   AGGAACAATT TAGTTTTAAG GACTTCATCC CTCCACCTAT
Val Glu Asp Ser
990

CCCTAACAGG CTGTAGATTA CCAAAACAAG ATTAATTTCA TCACTAAAAG AAAATCTATT
ATCAACTGCT GCTTCACCAG ACTTTTCTCT AGAAGCCGTC TGCGTTTACT CTTGTTTTCA
AAGGGACTTT TGTAAAATCA AATCATCCTG TCACAAGGCA GGAGGAGCTG ATAATGAACT
TTATTGGAGC ATTGATCTGC ATCCAAGGCC TTCTCAGGCC GGCTTGAGTG AATTGTGTAC
CTGAAGTACA GTATATTCTT GTAAATACAT AAAACAAAAG CATTTTGCTA AGGAGAAGCT
AATATGATTT TTTAAGTCTA TGTTTTAAAA TAATATGTAA ATTTTTCAGC TATTTAGTGA
TATATTTTAT GGGTGGGAAT AAAATTTCTA CTACAGAAAA AAAAAAAAAA AAAAAAAAA
AA
```

FIGURE 2-1

CTGTGTCCCG CAGCCGGATA ACCTGGCTGA CCCGATTCCG CGGACACCCG TGCAGCCGCG

GCTGGAGCCA GGGCGCCGGT GCCCGCGCTC TCCCCGGTCT TGCGCTGCGG GGGCCGATAC

CGCCTCTGTG ACTTCTTTGC GGGCCAGGGA CGGAGAAGGA GTCTGTGCCT GAGAAACTGG

GCTCTGTGCC CAGGCGCGAG GTGCAGG ATG GAG AGC AAG GGC CTG CTA GCT
               Met Glu Ser Lys Gly Leu Leu Ala
                1        5

GTC GCT CTG TGG TTC TGC GTG GAG ACC CGA GCC GCC TCT GTG GGT TTG
Val Ala Leu Trp Phe Cys Val Glu Thr Arg Ala Ala Ser Val Gly Leu
   10        15         20

CCT GGC GAT TTT CTC CAT CCC CCC AAG CTC AGC ACA CAG AAA GAC ATA
Pro Gly Asp Phe Leu His Pro Pro Lys Leu Ser Thr Gln Lys Asp Ile
25        30         35        40

CTG ACA ATT TTG GCA AAT ACA ACC CTT CAG ATT ACT TGC AGG GGA CAG
Leu Thr Ile Leu Ala Asn Thr Thr Leu Gln Ile Thr Cys Arg Gly Gln
        45         50        55

CGG GAC CTG GAC TGG CTT TGG CCC AAT GCT CAG CGT GAT TCT GAG GAA
Arg Asp Leu Asp Trp Leu Trp Pro Asn Ala Gln Arg Asp Ser Glu Glu
      60         65        70

AGG GTA TTG GTG ACT GAA TGC GGC GGT GGT GAC AGT ATC TTC TGC AAA
Arg Val Leu Val Thr Glu Cys Gly Gly Gly Asp Ser Ile Phe Cys Lys
   75        80         85

ACA CTC ACC ATT CCC AGG GTG GTT GGA AAT GAT ACT GGA GCC TAC AAG
Thr Leu Thr Ile Pro Arg Val Val Gly Asn Asp Thr Gly Ala Tyr Lys
  90        95        100

TGC TCG TAC CGG GAC GTC GAC ATA GCC TCC ACT GTT TAT GTC TAT GTT
Cys Ser Tyr Arg Asp Val Asp Ile Ala Ser Thr Val Tyr Val Tyr Val
105       110        115       120

CGA GAT TAC AGA TCA CCA TTC ATC GCC TCT GTC AGT GAC CAG CAT GGC
Arg Asp Tyr Arg Ser Pro Phe Ile Ala Ser Val Ser Asp Gln His Gly
        125        130       135

ATC GTG TAC ATC ACC GAG AAC AAG AAC AAA ACT GTG GTG ATC CCC TGC
Ile Val Tyr Ile Thr Glu Asn Lys Asn Lys Thr Val Val Ile Pro Cys
       140        145       150

CGA GGG TCG ATT TCA AAC CTC AAT GTG TCT CTT TGC GCT AGG TAT CCA
Arg Gly Ser Ile Ser Asn Leu Asn Val Ser Leu Cys Ala Arg Tyr Pro
   155       160        165

FIGURE 2-2

```
GAA AAG AGA TTT GTT CCG GAT GGA AAC AGA ATT TCC TGG GAC AGC GAG
Glu Lys Arg Phe Val Pro Asp Gly Asn Arg Ile Ser Trp Asp Ser Glu
    170             175             180

ATA GGC TTT ACT CTC CCC AGT TAC ATG ATC AGC TAT GCC GGC ATG GTC
Ile Gly Phe Thr Leu Pro Ser Tyr Met Ile Ser Tyr Ala Gly Met Val
185             190             195             200

TTC TGT GAG GCA AAG ATC AAT GAT GAA ACC TAT CAG TCT ATC ATG TAC
Phe Cys Glu Ala Lys Ile Asn Asp Glu Thr Tyr Gln Ser Ile Met Tyr
            205             210             215

ATA GTT GTG GTT GTA GGA TAT AGG ATT TAT GAT GTG ATT CTG AGC CCC
Ile Val Val Val Val Gly Tyr Arg Ile Tyr Asp Val Ile Leu Ser Pro
        220             225             230

CCG CAT GAA ATT GAG CTA TCT GCC GGA GAA AAA CTT GTC TTA AAT TGT
Pro His Glu Ile Glu Leu Ser Ala Gly Glu Lys Leu Val Leu Asn Cys
    235             240             245

ACA GCG AGA ACA GAG CTC AAT GTG GGG CTT GAT TTC ACC TGG CAC TCT
Thr Ala Arg Thr Glu Leu Asn Val Gly Leu Asp Phe Thr Trp His Ser
    250             255             260

CCA CCT TCA AAG TCT CAT CAT AAG AAG ATT GTA AAC CGG GAT GTG AAA
Pro Pro Ser Lys Ser His His Lys Lys Ile Val Asn Arg Asp Val Lys
265             270             275             280

CCC TTT CCT GGG ACT GTG GCG AAG ATG TTT TTG AGC ACC TTG ACA ATA
Pro Phe Pro Gly Thr Val Ala Lys Met Phe Leu Ser Thr Leu Thr Ile
            285             290             295

GAA AGT GTG ACC AAG AGT GAC CAA GGG GAA TAC ACC TGT GTA GCG TCC
Glu Ser Val Thr Lys Ser Asp Gln Gly Glu Tyr Thr Cys Val Ala Ser
        300             305             310

AGT GGA CGG ATG ATC AAG AGA AAT AGA ACA TTT GTC CGA GTT CAC ACA
Ser Gly Arg Met Ile Lys Arg Asn Arg Thr Phe Val Arg Val His Thr
    315             320             325

AAG CCT TTT ATT GCT TTC GGT AGT GGG ATG AAA TCT TTG GTG GAA GCC
Lys Pro Phe Ile Ala Phe Gly Ser Gly Met Lys Ser Leu Val Glu Ala
    330             335             340

ACA GTG GGC AGT CAA GTC CGA ATC CCT GTG AAG TAT CTC AGT TAC CCA
Thr Val Gly Ser Gln Val Arg Ile Pro Val Lys Tyr Leu Ser Tyr Pro
345             350             355             360
```

FIGURE 2-3

```
GCT CCT GAT ATC AAA TGG TAC AGA AAT GGA AGG CCC ATT GAG TCC AAC
Ala Pro Asp Ile Lys Trp Tyr Arg Asn Gly Arg Pro Ile Glu Ser Asn
            365                 370                 375

TAC ACA ATG ATT GTT GGC GAT GAA CTC ACC ATC ATG GAA GTG ACT GAA
Tyr Thr Met Ile Val Gly Asp Glu Leu Thr Ile Met Glu Val Thr Glu
            380                 385                 390

AGA GAT GCA GGA AAC TAC ACG GTC ATC CTC ACC AAC CCC ATT TCA ATG
Arg Asp Ala Gly Asn Tyr Thr Val Ile Leu Thr Asn Pro Ile Ser Met
            395                 400                 405

GAG AAA CAG AGC CAC ATG GTC TCT CTG GTT GTG AAT GTC CCA CCC CAG
Glu Lys Gln Ser His Met Val Ser Leu Val Val Asn Val Pro Pro Gln
    410                 415                 420

ATC GGT GAG AAA GCC TTG ATC TCG CCT ATG GAT TCC TAC CAG TAT GGG
Ile Gly Glu Lys Ala Leu Ile Ser Pro Met Asp Ser Tyr Gln Tyr Gly
425                 430                 435                 440

ACC ATG CAG ACA TTG ACA TGC ACA GTC TAC GCC AAC CCT CCC CTG CAC
Thr Met Gln Thr Leu Thr Cys Thr Val Tyr Ala Asn Pro Pro Leu His
            445                 450                 455

CAC ATC CAG TGG TAC TGG CAG CTA GAA GAA GCC TGC TCC TAC AGA CCC
His Ile Gln Trp Tyr Trp Gln Leu Glu Glu Ala Cys Ser Tyr Arg Pro
            460                 465                 470

GGC CAA ACA AGC CCG TAT GCT TGT AAA GAA TGG AGA CAC GTG GAG GAT
Gly Gln Thr Ser Pro Tyr Ala Cys Lys Glu Trp Arg His Val Glu Asp
            475                 480                 485

TTC CAG GGG GGA AAC AAG ATC GAA GTC ACC AAA AAC CAA TAT GCC CTG
Phe Gln Gly Gly Asn Lys Ile Glu Val Thr Lys Asn Gln Tyr Ala Leu
            490                 495                 500

ATT GAA GGA AAA AAC AAA ACT GTA AGT ACG CTG GTC ATC CAA GCT GCC
Ile Glu Gly Lys Asn Lys Thr Val Ser Thr Leu Val Ile Gln Ala Ala
505                 510                 515                 520

AAC GTG TCA GCG TTG TAC AAA TGT GAA GCC ATC AAC AAA GCG GGA CGA
Asn Val Ser Ala Leu Tyr Lys Cys Glu Ala Ile Asn Lys Ala Gly Arg
            525                 530                 535

GGA GAG AGG GTC ATC TCC TTC CAT GTG ATC AGG GGT CCT GAA ATT ACT
Gly Glu Arg Val Ile Ser Phe His Val Ile Arg Gly Pro Glu Ile Thr
            540                 545                 550
```

FIGURE 2-4

```
GTG CAA CCT GCT GCC CAG CCA ACT GAG CAG GAG AGT GTG TCC CTG TTG
Val Gln Pro Ala Ala Gln Pro Thr Glu Gln Glu Ser Val Ser Leu Leu
        555             560                 565

TGC ACT GCA GAC AGA AAT ACG TTT GAG AAC CTC ACG TGG TAC AAG CTT
Cys Thr Ala Asp Arg Asn Thr Phe Glu Asn Leu Thr Trp Tyr Lys Leu
    570             575                 580

GGC TCA CAG GCA ACA TCG GTC CAC ATG GGC GAA TCA CTC ACA CCA GTT
Gly Ser Gln Ala Thr Ser Val His Met Gly Glu Ser Leu Thr Pro Val
585             590                 595                     600

TGC AAG AAC TTG GAT GCT CTT TGG AAA CTG AAT GGC ACC ATG TTT TCT
Cys Lys Asn Leu Asp Ala Leu Trp Lys Leu Asn Gly Thr Met Phe Ser
            605                 610                 615

AAC AGC ACA AAT GAC ATC TTG ATT GTG GCA TTT CAG AAT GCC TCT CTG
Asn Ser Thr Asn Asp Ile Leu Ile Val Ala Phe Gln Asn Ala Ser Leu
        620                 625                 630

CAG GAC CAA GGC GAC TAT GTT TGC TCT GCT CAA GAT AAG AAG ACC AAG
Gln Asp Gln Gly Asp Tyr Val Cys Ser Ala Gln Asp Lys Lys Thr Lys
        635                 640                 645

AAA AGA CAT TGC CTG GTC AAA CAG CTC ATC ATC CTA GAG CGC ATG GCA
Lys Arg His Cys Leu Val Lys Gln Leu Ile Ile Leu Glu Arg Met Ala
    650                 655                 660

CCC ATG ATC ACC GGA AAT CTG GAG AAT CAG ACA ACA ACC ATT GGC GAG
Pro Met Ile Thr Gly Asn Leu Glu Asn Gln Thr Thr Thr Ile Gly Glu
665             670                 675                     680

ACC ATT GAA GTG ACT TGC CCA GCA TCT GGA AAT CCT ACC CCA CAC ATT
Thr Ile Glu Val Thr Cys Pro Ala Ser Gly Asn Pro Thr Pro His Ile
                685                 690                 695

ACA TGG TTC AAA GAC AAC GAG ACC CTG GTA GAA GAT TCA GGC ATT GTA
Thr Trp Phe Lys Asp Asn Glu Thr Leu Val Glu Asp Ser Gly Ile Val
            700                 705                 710

CTG AGA GAT GGG AAC CGG AAC CTG ACT ATC CGC AGG GTG AGG AAG GAG
Leu Arg Asp Gly Asn Arg Asn Leu Thr Ile Arg Arg Val Arg Lys Glu
        715                 720                 725

GAT GGA GGC CTC TAC ACC TGC CAG GCC TGC AAT GTC CTT GGC TGT GCA
Asp Gly Gly Leu Tyr Thr Cys Gln Ala Cys Asn Val Leu Gly Cys Ala
730                 735                 740
```

FIGURE 2-5

```
AGA GCG GAG ACG CTC TTC ATA ATA GAA GGT GCC CAG GAA AAG ACC AAC
Arg Ala Glu Thr Leu Phe Ile Ile Glu Gly Ala Gln Glu Lys Thr Asn
745             750             755             760

TTG GAA GTC ATT ATC CTC GTC GGC ACT GCA GTG ATT GCC ATG TTC TTC
Leu Glu Val Ile Ile Leu Val Gly Thr Ala Val Ile Ala Met Phe Phe
                765             770             775

TGG CTC CTT CTT GTC ATT CTC GTA CGG ACC GTT AAG CGG GCC AAT GAA
Trp Leu Leu Leu Val Ile Leu Val Arg Thr Val Lys Arg Ala Asn Glu
            780             785             790

GGG GAA CTG AAG ACA GGC TAC TTG TCT ATT GTC ATG GAT CCA GAT GAA
Gly Glu Leu Lys Thr Gly Tyr Leu Ser Ile Val Met Asp Pro Asp Glu
        795             800             805

TTG CCC TTG GAT GAG CGC TGT GAA CGC TTG CCT TAT GAT GCC AGC AAG
Leu Pro Leu Asp Glu Arg Cys Glu Arg Leu Pro Tyr Asp Ala Ser Lys
    810             815             820

TGG GAA TTC CCC AGG GAC CGG CTG AAA CTA GGA AAA CCT CTT GGC CGC
Trp Glu Phe Pro Arg Asp Arg Leu Lys Leu Gly Lys Pro Leu Gly Arg
825             830             835             840

GGT GCC TTC GGC CAA GTG ATT GAG GCA GAC GCT TTT GGA ATT GAC AAG
Gly Ala Phe Gly Gln Val Ile Glu Ala Asp Ala Phe Gly Ile Asp Lys
                845             850             855

ACA GCG ACT TGC AAA ACA GTA GCC GTC AAG ATG TTG AAA GAA GGA GCA
Thr Ala Thr Cys Lys Thr Val Ala Val Lys Met Leu Lys Glu Gly Ala
            860             865             870

ACA CAC AGC GAG CAT CGA GCC CTC ATG TCT GAA CTC AAG ATC CTC ATC
Thr His Ser Glu His Arg Ala Leu Met Ser Glu Leu Lys Ile Leu Ile
        875             880             885

CAC ATT GGT CAC CAT CTC AAT GTG GTG AAC CTC CTA GGC GCC TGC ACC
His Ile Gly His His Leu Asn Val Val Asn Leu Leu Gly Ala Cys Thr
    890             895             900

AAG CCG GGA GGG CCT CTC ATG GTG ATT GTG GAA TTC TCG AAG TTT GGA
Lys Pro Gly Gly Pro Leu Met Val Ile Val Glu Phe Ser Lys Phe Gly
905             910             915             920

AAC CTA TCA ACT TAC TTA CGG GGC AAG AGA AAT GAA TTT GTT CCC TAT
Asn Leu Ser Thr Tyr Leu Arg Gly Lys Arg Asn Glu Phe Val Pro Tyr
                925             930             935
```

FIGURE 2-6

```
AAG AGC AAA GGG GCA CGC TTC CGC CAG GGC AAG GAC TAC GTT GGG GAG
Lys Ser Lys Gly Ala Arg Phe Arg Gln Gly Lys Asp Tyr Val Gly Glu
            940                 945                 950

CTC TCC GTG GAT CTG AAA AGA CGC TTG GAC AGC ATC ACC AGC AGC CAG
Leu Ser Val Asp Leu Lys Arg Arg Leu Asp Ser Ile Thr Ser Ser Gln
            955                 960                 965

AGC TCT GCC AGC TCA GGC TTT GTT GAG GAG AAA TCG CTC AGT GAT GTA
Ser Ser Ala Ser Ser Gly Phe Val Glu Glu Lys Ser Leu Ser Asp Val
            970                 975                 980

GAG GAA GAA GAA GCT TCT GAA GAA CTG TAC AAG GAC TTC CTG ACC TTG
Glu Glu Glu Glu Ala Ser Glu Glu Leu Tyr Lys Asp Phe Leu Thr Leu
985                 990                 995                 1000

GAG CAT CTC ATC TGT TAC AGC TTC CAA GTG GCT AAG GGC ATG GAG TTC
Glu His Leu Ile Cys Tyr Ser Phe Gln Val Ala Lys Gly Met Glu Phe
                1005                1010                1015

TTG GCA TCA AGG AAG TGT ATC CAC AGG GAC CTG GCA GCA CGA AAC ATT
Leu Ala Ser Arg Lys Cys Ile His Arg Asp Leu Ala Ala Arg Asn Ile
            1020                1025                1030

CTC CTA TCG GAG AAG AAT GTG GTT AAG ATC TGT GAC TTC GGC TTG GCC
Leu Leu Ser Glu Lys Asn Val Val Lys Ile Cys Asp Phe Gly Leu Ala
            1035                1040                1045

CGG GAC ATT TAT AAA GAC CCG GAT TAT GTC AGA AAA GGA GAT GCC CGA
Arg Asp Ile Tyr Lys Asp Pro Asp Tyr Val Arg Lys Gly Asp Ala Arg
            1050                1055                1060

CTC CCT TTG AAG TGG ATG GCC CCG GAA ACC ATT TTT GAC AGA GTA TAC
Leu Pro Leu Lys Trp Met Ala Pro Glu Thr Ile Phe Asp Arg Val Tyr
1065                1070                1075                1080

ACA ATT CAG AGC GAT GTG TGG TCT TTC GGT GTG TTG CTC TGG GAA ATA
Thr Ile Gln Ser Asp Val Trp Ser Phe Gly Val Leu Leu Trp Glu Ile
                1085                1090                1095

TTT TCC TTA GGT GCC TCC CCA TAC CCT GGG GTC AAG ATT GAT GAA GAA
Phe Ser Leu Gly Ala Ser Pro Tyr Pro Gly Val Lys Ile Asp Glu Glu
            1100                1105                1110

TTT TGT AGG AGA TTG AAA GAA GGA ACT AGA ATG CGG GCT CCT GAC TAC
Phe Cys Arg Arg Leu Lys Glu Gly Thr Arg Met Arg Ala Pro Asp Tyr
            1115                1120                1125
```

FIGURE 2-7

```
ACT ACC CCA GAA ATG TAC CAG ACC ATG CTG GAC TGC TGG CAT GAG GAC
Thr Thr Pro Glu Met Tyr Gln Thr Met Leu Asp Cys Trp His Glu Asp
        1130            1135            1140

CCC AAC CAG AGA CCC TCG TTT TCA GAG TTG GTG GAG CAT TTG GGA AAC
Pro Asn Gln Arg Pro Ser Phe Ser Glu Leu Val Glu His Leu Gly Asn
1145            1150            1155            1160

CTC CTG CAA GCA AAT GCG CAG CAG GAT GGC AAA GAC TAT ATT GTT CTT
Leu Leu Gln Ala Asn Ala Gln Gln Asp Gly Lys Asp Tyr Ile Val Leu
                1165            1170            1175

CCA ATG TCA GAG ACA CTG AGC ATG GAA GAG GAT TCT GGA CTC TCC CTG
Pro Met Ser Glu Thr Leu Ser Met Glu Glu Asp Ser Gly Leu Ser Leu
        1180            1185            1190

CCT ACC TCA CCT GTT TCC TGT ATG GAG GAA GAG GAA GTG TGC GAC CCC
Pro Thr Ser Pro Val Ser Cys Met Glu Glu Glu Glu Val Cys Asp Pro
        1195            1200            1205

AAA TTC CAT TAT GAC AAC ACA GCA GGA ATC AGT CAT TAT CTC CAG AAC
Lys Phe His Tyr Asp Asn Thr Ala Gly Ile Ser His Tyr Leu Gln Asn
    1210            1215            1220

AGT AAG CGA AAG AGC CGG CCA GTG AGT GTA AAA ACA TTT GAA GAT ATC
Ser Lys Arg Lys Ser Arg Pro Val Ser Val Lys Thr Phe Glu Asp Ile
1225            1230            1235            1240

CCA TTG GAG GAA CCA GAA GTA AAA GTG ATC CCA GAT GAC AGC CAG ACA
Pro Leu Glu Glu Pro Glu Val Lys Val Ile Pro Asp Asp Ser Gln Thr
            1245            1250            1255

GAC AGT GGG ATG GTC CTT GCA TCA GAA GAG CTG AAA ACT CTG GAA GAC
Asp Ser Gly Met Val Leu Ala Ser Glu Glu Leu Lys Thr Leu Glu Asp
                1260            1265            1270

AGG AAC AAA TTA TCT CCA TCT TTT GGT GGA ATG ATG CCC AGT AAA AGC
Arg Asn Lys Leu Ser Pro Ser Phe Gly Gly Met Met Pro Ser Lys Ser
            1275            1280            1285

AGG GAG TCT GTG GCC TCG GAA GGC TCC AAC CAG ACC AGT GGC TAC CAG
Arg Glu Ser Val Ala Ser Glu Gly Ser Asn Gln Thr Ser Gly Tyr Gln
        1290            1295            1300

TCT GGG TAT CAC TCA GAT GAC ACA GAC ACC ACC GTG TAC TCC AGC GAC
Ser Gly Tyr His Ser Asp Asp Thr Asp Thr Thr Val Tyr Ser Ser Asp
1305            1310            1315            1320
```

FIGURE 2-8

```
GAG GCA GGA CTT TTA AAG ATG GTG GAT GCT GCA GTT CAC GCT GAC TCA
Glu Ala Gly Leu Leu Lys Met Val Asp Ala Ala Val His Ala Asp Ser
            1325                1330                1335

GGG ACC ACA CTG CAG CTC ACC TCC TGT TTA AAT GGA AGT GGT CCT GTC
Gly Thr Thr Leu Gln Leu Thr Ser Cys Leu Asn Gly Ser Gly Pro Val
            1340                1345                1350

CCG GCT CCG CCC CCA ACT CCT GGA AAT CAC GAG AGA GGT GCT GCT TAG
Pro Ala Pro Pro Pro Thr Pro Gly Asn His Glu Arg Gly Ala Ala
            1355                1360                1365
```

```
ATTTTCAAGT GTTGTTCTTT CCACCACCCG GAAGTAGCCA CATTTGATTT TCATTTTTGG
AGGAGGGACC TCAGACTGCA AGGAGCTTGT CCTCAGGGCA TTTCCAGAGA AGATGCCCAT
GACCCAAGAA TGTGTTGACT CTACTCTCTT TTCCATTCAT TTAAAAGTCC TATATAATGT
GCCCTGCTGT GGTCTCACTA CCAGTTAAAG CAAAAGACTT TCAAACACGT GGACTCTGTC
CTCCAAGAAG TGGCAACGGC ACCTCTGTGA AACTGGATCG AATGGGCAAT GCTTTGTGTG
TTGAGGATGG GTGAGATGTC CCAGGGCCGA GTCTGTCTAC CTTGGAGGCT TTGTGGAGGA
TGCGGCTATG AGCCAAGTGT TAAGTGTGGG ATGTGGACTG GGAGGAAGGA AGGCGCAAGC
CGTCCGGAGA GCGGTTGGAG CCTGCAGATG CATTGTGCTG GCTCTGGTGG AGGTGGGCTT
GTGGCCTGTC AGGAAACGCA AAGGCGGCCG GCAGGGTTTG GTTTTGGAAG GTTTGCGTGC
TCTTCACAGT CGGGTTACAG GCGAGTTCCC TGTGGCGTTT CCTACTCCTA ATGAGAGTTC
CTTCCGGACT CTTACGTGTC TCCTGGCCTG GCCCCAGGAA GGAAATGATG CAGCTTGCTC
CTTCCTCATC TCTCAGGCTG TGCCTTAATT CAGAACACCA AAAGAGAGGA ACGTCGGCAG
AGGCTCCTGA CGGGGCCGAA GAATTGTGAG AACAGAACAG AAACTCAGGG TTTCTGCTGG
GTGGAGACCC ACGTGGCGCC CTGGTGGCAG GTCTGAGGGT TCTCTGTCAA GTGGCGGTAA
AGGCTCAGGC TGGTGTTCTT CCTCTATCTC CACTCCTGTC AGGCCCCCAA GTCCTCAGTA
TTTTAGCTTT GTGGCTTCCT GATGGCAGAA AAATCTTAAT TGGTTGGTTT GCTCTCCAGA
TAATCACTAG CCAGATTTCG AAATTACTTT TTAGCCGAGG TTATGATAAC ATCTACTGTA
TCCTTTAGAA TTTTAACCTA TAAAACTATG TCTACTGGTT TCTGCCTGTG TGCTTATGTT
AAAAAAAAAA AAAAA
```

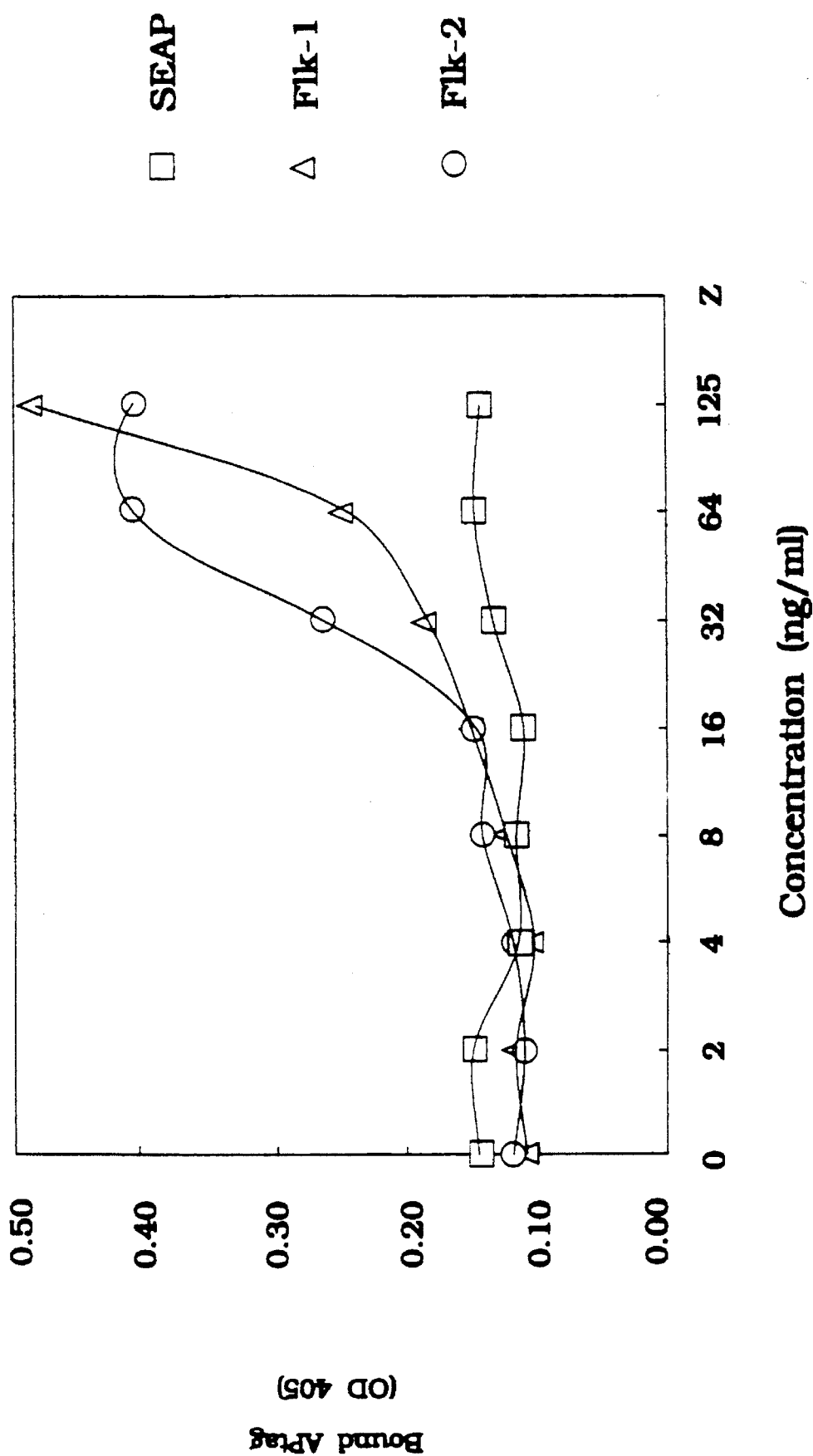

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 3453 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( i x ) FEATURE:
  ( A ) NAME/KEY: CDS
  ( B ) LOCATION: 31..3009

( i x ) FEATURE:
  ( A ) NAME/KEY: mat_peptide
  ( B ) LOCATION: 31..3006

( x i ) SEQUENCE DESCRIPTION: SEQ ID NO:1:

```
GCGGCCTGGC TACCGCGCGC TCCGGAGGCC ATG CGG GCG TTG GCG CAG CGC AGC        54
                                Met Arg Ala Leu Ala Gln Arg Ser
                                 1               5

GAC CGG CGG CTG CTG CTG CTT GTT GTT TTG TCA GTA ATG ATT CTT GAG        102
Asp Arg Arg Leu Leu Leu Leu Val Val Leu Ser Val Met Ile Leu Glu
     10              15                  20

ACC GTT ACA AAC CAA GAC CTG CCT GTG ATC AAG TGT GTT TTA ATC AGT        150
Thr Val Thr Asn Gln Asp Leu Pro Val Ile Lys Cys Val Leu Ile Ser
 25              30                  35                      40

CAT GAG AAC AAT GGC TCA TCA GCG GGA AAG CCA TCA TCG TAC CGA ATG        198
His Glu Asn Asn Gly Ser Ser Ala Gly Lys Pro Ser Ser Tyr Arg Met
                 45                  50                  55

GTG CGA GGA TCC CCA GAA GAC CTC CAG TGT ACC CCG AGG CGC CAG AGT        246
Val Arg Gly Ser Pro Glu Asp Leu Gln Cys Thr Pro Arg Arg Gln Ser
             60                  65                  70

GAA GGG ACG GTA TAT GAA GCG GCC ACC GTG GAG GTG GCC GAG TCT GGG        294
Glu Gly Thr Val Tyr Glu Ala Ala Thr Val Glu Val Ala Glu Ser Gly
             75                  80                  85

TCC ATC ACC CTG CAA GTG CAG CTC GCC ACC CCA GGG GAC CTT TCC TGC        342
Ser Ile Thr Leu Gln Val Gln Leu Ala Thr Pro Gly Asp Leu Ser Cys
         90                  95                 100

CTC TGG GTC TTT AAG CAC AGC TCC CTG GGC TGC CAG CCG CAC TTT GAT        390
Leu Trp Val Phe Lys His Ser Ser Leu Gly Cys Gln Pro His Phe Asp
105                 110                 115                 120

TTA CAA AAC AGA GGA ATC GTT TCC ATG GCC ATC TTG AAC GTG ACA GAG        438
Leu Gln Asn Arg Gly Ile Val Ser Met Ala Ile Leu Asn Val Thr Glu
                125                 130                 135

ACC CAG GCA GGA GAA TAC CTA CTC CAT ATT CAG AGC GAA CGC GCC AAC        486
Thr Gln Ala Gly Glu Tyr Leu Leu His Ile Gln Ser Glu Arg Ala Asn
            140                 145                 150

TAC ACA GTA CTG TTC ACA GTG AAT GTA AGA GAT ACA CAG CTG TAT GTG        534
Tyr Thr Val Leu Phe Thr Val Asn Val Arg Asp Thr Gln Leu Tyr Val
            155                 160                 165

CTA AGG AGA CCT TAC TTT AGG AAG ATG GAA AAC CAG GAT GCA CTG CTC        582
Leu Arg Arg Pro Tyr Phe Arg Lys Met Glu Asn Gln Asp Ala Leu Leu
170                 175                 180

TGC ATC TCC GAG GGT GTT CCG GAG CCC ACT GTG GAG TGG GTG CTC TGC        630
Cys Ile Ser Glu Gly Val Pro Glu Pro Thr Val Glu Trp Val Leu Cys
185                 190                 195                 200

AGC TCC CAC AGG GAA AGC TGT AAA GAA GAA GGC CCT GCT GTT GTC AGA        678
Ser Ser His Arg Glu Ser Cys Lys Glu Glu Gly Pro Ala Val Val Arg
                205                 210                 215

AAG GAG GAA AAG GTA CTT CAT GAG TTG TTC GGA ACA GAC ATC AGA TGC        726
Lys Glu Glu Lys Val Leu His Glu Leu Phe Gly Thr Asp Ile Arg Cys
            220                 225                 230

TGT GCT AGA AAT GCA CTG GGC CGC GAA TGC ACC AAG CTG TTC ACC ATA        774
```

-continued

| | | | | | | | | | | | | | | | |
|---|---|---|---|---|---|---|---|---|---|---|---|---|---|---|---|
| Cys | Ala | Arg | Asn | Ala | Leu | Gly | Arg | Glu | Cys | Thr | Lys | Leu | Phe | Thr | Ile |
| | | 235 | | | | 240 | | | | | 245 | | | | |

| GAT | CTA | AAC | CAG | GCT | CCT | CAG | AGC | ACA | CTG | CCC | CAG | TTA | TTC | CTG | AAA | 822 |
| Asp | Leu | Asn | Gln | Ala | Pro | Gln | Ser | Thr | Leu | Pro | Gln | Leu | Phe | Leu | Lys | |
| | 250 | | | | 255 | | | | | 260 | | | | | | |

| GTG | GGG | GAA | CCC | TTG | TGG | ATC | AGG | TGT | AAG | GCC | ATC | CAT | GTG | AAC | CAT | 870 |
| Val | Gly | Glu | Pro | Leu | Trp | Ile | Arg | Cys | Lys | Ala | Ile | His | Val | Asn | His | |
| 265 | | | | | 270 | | | | 275 | | | | | | 280 | |

| GGA | TTC | GGG | CTC | ACC | TGG | GAG | CTG | GAA | GAC | AAA | GCC | CTG | GAG | GAG | GGC | 918 |
| Gly | Phe | Gly | Leu | Thr | Trp | Glu | Leu | Glu | Asp | Lys | Ala | Leu | Glu | Glu | Gly | |
| | | | | 285 | | | | | 290 | | | | | 295 | | |

| AGC | TAC | TTT | GAG | ATG | AGT | ACC | TAC | TCC | ACA | AAC | AGG | ACC | ATG | ATT | CGG | 966 |
| Ser | Tyr | Phe | Glu | Met | Ser | Thr | Tyr | Ser | Thr | Asn | Arg | Thr | Met | Ile | Arg | |
| | | | 300 | | | | | 305 | | | | | 310 | | | |

| ATT | CTC | TTG | GCC | TTT | GTG | TCT | TCC | GTG | GGA | AGG | AAC | GAC | ACC | GGA | TAT | 1014 |
| Ile | Leu | Leu | Ala | Phe | Val | Ser | Ser | Val | Gly | Arg | Asn | Asp | Thr | Gly | Tyr | |
| | | | 315 | | | | | 320 | | | | | 325 | | | |

| TAC | ACC | TGC | TCT | TCC | TCA | AAG | CAC | CCC | AGC | CAG | TCA | GCG | TTG | GTG | ACC | 1062 |
| Tyr | Thr | Cys | Ser | Ser | Ser | Lys | His | Pro | Ser | Gln | Ser | Ala | Leu | Val | Thr | |
| | 330 | | | | | 335 | | | | | 340 | | | | | |

| ATC | CTA | GAA | AAA | GGG | TTT | ATA | AAC | GCT | ACC | AGC | TCG | CAA | GAA | GAG | TAT | 1110 |
| Ile | Leu | Glu | Lys | Gly | Phe | Ile | Asn | Ala | Thr | Ser | Ser | Gln | Glu | Glu | Tyr | |
| 345 | | | | | 350 | | | | | 355 | | | | | 360 | |

| GAA | ATT | GAC | CCG | TAC | GAA | AAG | TTC | TGC | TTC | TCA | GTC | AGG | TTT | AAA | GCG | 1158 |
| Glu | Ile | Asp | Pro | Tyr | Glu | Lys | Phe | Cys | Phe | Ser | Val | Arg | Phe | Lys | Ala | |
| | | | | 365 | | | | | 370 | | | | | 375 | | |

| TAC | CCA | CGA | ATC | CGA | TGC | ACG | TGG | ATC | TTC | TCT | CAA | GCC | TCA | TTT | CCT | 1206 |
| Tyr | Pro | Arg | Ile | Arg | Cys | Thr | Trp | Ile | Phe | Ser | Gln | Ala | Ser | Phe | Pro | |
| | | | 380 | | | | | 385 | | | | | 390 | | | |

| TGT | GAA | CAG | AGA | GGC | CTG | GAG | GAT | GGG | TAC | AGC | ATA | TCT | AAA | TTT | TGC | 1254 |
| Cys | Glu | Gln | Arg | Gly | Leu | Glu | Asp | Gly | Tyr | Ser | Ile | Ser | Lys | Phe | Cys | |
| | | 395 | | | | | 400 | | | | | 405 | | | | |

| GAT | CAT | AAG | AAC | AAG | CCA | GGA | GAG | TAC | ATA | TTC | TAT | GCA | GAA | AAT | GAT | 1302 |
| Asp | His | Lys | Asn | Lys | Pro | Gly | Glu | Tyr | Ile | Phe | Tyr | Ala | Glu | Asn | Asp | |
| | 410 | | | | | 415 | | | | | 420 | | | | | |

| GAC | GCC | CAG | TTC | ACC | AAA | ATG | TTC | ACG | CTG | AAT | ATA | AGA | AAG | AAA | CCT | 1350 |
| Asp | Ala | Gln | Phe | Thr | Lys | Met | Phe | Thr | Leu | Asn | Ile | Arg | Lys | Lys | Pro | |
| 425 | | | | | 430 | | | | | 435 | | | | | 440 | |

| CAA | GTG | CTA | GCA | AAT | GCC | TCA | GCC | AGC | CAG | GCG | TCC | TGT | TCC | TCT | GAT | 1398 |
| Gln | Val | Leu | Ala | Asn | Ala | Ser | Ala | Ser | Gln | Ala | Ser | Cys | Ser | Ser | Asp | |
| | | | | 445 | | | | | 450 | | | | | 455 | | |

| GGC | TAC | CCG | CTA | CCC | TCT | TGG | ACC | TGG | AAG | AAG | TGT | TCG | GAC | AAA | TCT | 1446 |
| Gly | Tyr | Pro | Leu | Pro | Ser | Trp | Thr | Trp | Lys | Lys | Cys | Ser | Asp | Lys | Ser | |
| | | | 460 | | | | | 465 | | | | | 470 | | | |

| CCC | AAT | TGC | ACG | GAG | GAA | ATC | CCA | GAA | GGA | GTT | TGG | AAT | AAA | AAG | GCT | 1494 |
| Pro | Asn | Cys | Thr | Glu | Glu | Ile | Pro | Glu | Gly | Val | Trp | Asn | Lys | Lys | Ala | |
| | | 475 | | | | | 480 | | | | | 485 | | | | |

| AAC | AGA | AAA | GTG | TTT | GGC | CAG | TGG | GTG | TCG | AGC | AGT | ACT | CTA | AAT | ATG | 1542 |
| Asn | Arg | Lys | Val | Phe | Gly | Gln | Trp | Val | Ser | Ser | Ser | Thr | Leu | Asn | Met | |
| | 490 | | | | | 495 | | | | | 500 | | | | | |

| AGT | GAG | GCC | GGG | AAA | GGG | CTT | CTG | GTC | AAA | TGT | TGT | GCG | TAC | AAT | TCT | 1590 |
| Ser | Glu | Ala | Gly | Lys | Gly | Leu | Leu | Val | Lys | Cys | Cys | Ala | Tyr | Asn | Ser | |
| 505 | | | | | 510 | | | | | 515 | | | | | 520 | |

| ATG | GGC | ACG | TCT | TGC | GAA | ACC | ATC | TTT | TTA | AAC | TCA | CCA | GGC | CCC | TTC | 1638 |
| Met | Gly | Thr | Ser | Cys | Glu | Thr | Ile | Phe | Leu | Asn | Ser | Pro | Gly | Pro | Phe | |
| | | | | 525 | | | | | 530 | | | | | 535 | | |

| CCT | TTC | ATC | CAA | GAC | AAC | ATC | TCC | TTC | TAT | GCG | ACC | ATT | GGG | CTC | TGT | 1686 |
| Pro | Phe | Ile | Gln | Asp | Asn | Ile | Ser | Phe | Tyr | Ala | Thr | Ile | Gly | Leu | Cys | |
| | | | 540 | | | | | 545 | | | | | 550 | | | |

| CTC | CCC | TTC | ATT | GTT | GTT | CTC | ATT | GTG | TTG | ATC | TGC | CAC | AAA | TAC | AAA | 1734 |

|  |  |  |  |  |  |  |  |  |  |  |  |  |  |  |  |
|---|---|---|---|---|---|---|---|---|---|---|---|---|---|---|---|
| Leu | Pro | Phe 555 | Ile | Val | Val | Leu | Ile 560 | Val | Leu | Ile | Cys | His 565 | Lys | Tyr | Lys |

| AAG | CAA | TTT | AGG | TAC | GAG | AGT | CAG | CTG | CAG | ATG | ATC | CAG | GTG | ACT | GGC | 1782 |
|---|---|---|---|---|---|---|---|---|---|---|---|---|---|---|---|---|
| Lys | Gln | Phe | Arg | Tyr | Glu | Ser | Gln | Leu | Gln | Met | Ile | Gln | Val | Thr | Gly |  |
|  | 570 |  |  |  | 575 |  |  |  |  | 580 |  |  |  |  |  |  |

| CCC | CTG | GAT | AAC | GAG | TAC | TTC | TAC | GTT | GAC | TTC | AGG | GAC | TAT | GAA | TAT | 1830 |
|---|---|---|---|---|---|---|---|---|---|---|---|---|---|---|---|---|
| Pro | Leu | Asp | Asn | Glu | Tyr | Phe | Tyr | Val | Asp | Phe | Arg | Asp | Tyr | Glu | Tyr |  |
| 585 |  |  |  |  | 590 |  |  |  |  | 595 |  |  |  |  | 600 |  |

| GAC | CTT | AAG | TGG | GAG | TTC | CCG | AGA | GAG | AAC | TTA | GAG | TTT | GGG | AAG | GTC | 1878 |
|---|---|---|---|---|---|---|---|---|---|---|---|---|---|---|---|---|
| Asp | Leu | Lys | Trp | Glu | Phe | Pro | Arg | Glu | Asn | Leu | Glu | Phe | Gly | Lys | Val |  |
|  |  |  |  | 605 |  |  |  |  | 610 |  |  |  |  | 615 |  |  |

| CTG | GGG | TCT | GGC | GCT | TTC | GGG | AGG | GTG | ATG | AAC | GCC | ACG | GCC | TAT | GGC | 1926 |
|---|---|---|---|---|---|---|---|---|---|---|---|---|---|---|---|---|
| Leu | Gly | Ser | Gly | Ala | Phe | Gly | Arg | Val | Met | Asn | Ala | Thr | Ala | Tyr | Gly |  |
|  |  |  | 620 |  |  |  |  | 625 |  |  |  |  | 630 |  |  |  |

| ATT | AGT | AAA | ACG | GGA | GTC | TCA | ATT | CAG | GTG | GCG | GTG | AAG | ATG | CTA | AAA | 1974 |
|---|---|---|---|---|---|---|---|---|---|---|---|---|---|---|---|---|
| Ile | Ser | Lys | Thr | Gly | Val | Ser | Ile | Gln | Val | Ala | Val | Lys | Met | Leu | Lys |  |
|  |  | 635 |  |  |  |  | 640 |  |  |  |  | 645 |  |  |  |  |

| GAG | AAA | GCT | GAC | AGC | TGT | GAA | AAA | GAA | GCT | CTC | ATG | TCG | GAG | CTC | AAA | 2022 |
|---|---|---|---|---|---|---|---|---|---|---|---|---|---|---|---|---|
| Glu | Lys | Ala | Asp | Ser | Cys | Glu | Lys | Glu | Ala | Leu | Met | Ser | Glu | Leu | Lys |  |
|  | 650 |  |  |  |  | 655 |  |  |  |  | 660 |  |  |  |  |  |

| ATG | ATG | ACC | CAC | CTG | GGA | CAC | CAT | GAC | AAC | ATC | GTG | AAT | CTG | CTG | GGG | 2070 |
|---|---|---|---|---|---|---|---|---|---|---|---|---|---|---|---|---|
| Met | Met | Thr | His | Leu | Gly | His | His | Asp | Asn | Ile | Val | Asn | Leu | Leu | Gly |  |
| 665 |  |  |  |  | 670 |  |  |  |  | 675 |  |  |  |  | 680 |  |

| GCA | TGC | ACA | CTG | TCA | GGG | CCA | GTG | TAC | TTG | ATT | TTT | GAA | TAT | TGT | TGC | 2118 |
|---|---|---|---|---|---|---|---|---|---|---|---|---|---|---|---|---|
| Ala | Cys | Thr | Leu | Ser | Gly | Pro | Val | Tyr | Leu | Ile | Phe | Glu | Tyr | Cys | Cys |  |
|  |  |  |  | 685 |  |  |  |  | 690 |  |  |  |  | 695 |  |  |

| TAT | GGT | GAC | CTC | CTC | AAC | TAC | CTA | AGA | AGT | AAA | AGA | GAG | AAG | TTT | CAC | 2166 |
|---|---|---|---|---|---|---|---|---|---|---|---|---|---|---|---|---|
| Tyr | Gly | Asp | Leu | Leu | Asn | Tyr | Leu | Arg | Ser | Lys | Arg | Glu | Lys | Phe | His |  |
|  |  |  | 700 |  |  |  |  | 705 |  |  |  |  | 710 |  |  |  |

| AGG | ACA | TGG | ACA | GAG | ATT | TTT | AAG | GAA | CAT | AAT | TTC | AGT | TCT | TAC | CCT | 2214 |
|---|---|---|---|---|---|---|---|---|---|---|---|---|---|---|---|---|
| Arg | Thr | Trp | Thr | Glu | Ile | Phe | Lys | Glu | His | Asn | Phe | Ser | Ser | Tyr | Pro |  |
|  |  | 715 |  |  |  |  | 720 |  |  |  |  | 725 |  |  |  |  |

| ACT | TTC | CAG | GCA | CAT | TCA | AAT | TCC | AGC | ATG | CCT | GGT | TCA | CGA | GAA | GTT | 2262 |
|---|---|---|---|---|---|---|---|---|---|---|---|---|---|---|---|---|
| Thr | Phe | Gln | Ala | His | Ser | Asn | Ser | Ser | Met | Pro | Gly | Ser | Arg | Glu | Val |  |
|  | 730 |  |  |  |  | 735 |  |  |  |  | 740 |  |  |  |  |  |

| CAG | TTA | CAC | CCG | CCC | TTG | GAT | CAG | CTC | TCA | GGG | TTC | AAT | GGG | AAT | TCA | 2310 |
|---|---|---|---|---|---|---|---|---|---|---|---|---|---|---|---|---|
| Gln | Leu | His | Pro | Pro | Leu | Asp | Gln | Leu | Ser | Gly | Phe | Asn | Gly | Asn | Ser |  |
| 745 |  |  |  |  | 750 |  |  |  |  | 755 |  |  |  |  | 760 |  |

| ATT | CAT | TCT | GAA | GAT | GAG | ATT | GAA | TAT | GAA | AAC | CAG | AAG | AGG | CTG | GCA | 2358 |
|---|---|---|---|---|---|---|---|---|---|---|---|---|---|---|---|---|
| Ile | His | Ser | Glu | Asp | Glu | Ile | Glu | Tyr | Glu | Asn | Gln | Lys | Arg | Leu | Ala |  |
|  |  |  |  | 765 |  |  |  |  | 770 |  |  |  |  | 775 |  |  |

| GAA | GAA | GAG | GAG | GAA | GAT | TTG | AAC | GTG | CTG | ACG | TTT | GAA | GAC | CTC | CTT | 2406 |
|---|---|---|---|---|---|---|---|---|---|---|---|---|---|---|---|---|
| Glu | Glu | Glu | Glu | Glu | Asp | Leu | Asn | Val | Leu | Thr | Phe | Glu | Asp | Leu | Leu |  |
|  |  |  | 780 |  |  |  |  | 785 |  |  |  |  | 790 |  |  |  |

| TGC | TTT | GCG | TAC | CAA | GTG | GCC | AAA | GGC | ATG | GAA | TTC | CTG | GAG | TTC | AAG | 2454 |
|---|---|---|---|---|---|---|---|---|---|---|---|---|---|---|---|---|
| Cys | Phe | Ala | Tyr | Gln | Val | Ala | Lys | Gly | Met | Glu | Phe | Leu | Glu | Phe | Lys |  |
|  |  | 795 |  |  |  |  | 800 |  |  |  |  | 805 |  |  |  |  |

| TCG | TGT | GTC | CAC | AGA | GAC | CTG | GCA | GCC | AGG | AAT | GTG | TTG | GTC | ACC | CAC | 2502 |
|---|---|---|---|---|---|---|---|---|---|---|---|---|---|---|---|---|
| Ser | Cys | Val | His | Arg | Asp | Leu | Ala | Ala | Arg | Asn | Val | Leu | Val | Thr | His |  |
|  | 810 |  |  |  |  | 815 |  |  |  |  | 820 |  |  |  |  |  |

| GGG | AAG | GTG | GTG | AAG | ATC | TGT | GAC | TTT | GGA | CTG | GCC | CGA | GAC | ATC | CTG | 2550 |
|---|---|---|---|---|---|---|---|---|---|---|---|---|---|---|---|---|
| Gly | Lys | Val | Val | Lys | Ile | Cys | Asp | Phe | Gly | Leu | Ala | Arg | Asp | Ile | Leu |  |
| 825 |  |  |  |  | 830 |  |  |  |  | 835 |  |  |  |  | 840 |  |

| AGC | GAC | TCC | AGC | TAC | GTC | GTC | AGG | GGC | AAC | GCA | CGG | CTG | CCG | GTG | AAG | 2598 |
|---|---|---|---|---|---|---|---|---|---|---|---|---|---|---|---|---|
| Ser | Asp | Ser | Ser | Tyr | Val | Val | Arg | Gly | Asn | Ala | Arg | Leu | Pro | Val | Lys |  |
|  |  |  |  | 845 |  |  |  |  | 850 |  |  |  |  | 855 |  |  |

| TGG | ATG | GCA | CCC | GAG | AGC | TTA | TTT | GAA | GGG | ATC | TAC | ACA | ATC | AAG | AGT | 2646 |
|---|---|---|---|---|---|---|---|---|---|---|---|---|---|---|---|---|
| Trp | Met | Ala | Pro | Glu | Ser | Leu | Phe | Glu | Gly | Ile | Tyr | Thr | Ile | Lys | Ser |  |
|  |  |  | 860 |  |  |  |  | 865 |  |  |  |  | 870 |  |  |  |

| GAC | GTC | TGG | TCC | TAC | GGC | ATC | CTT | CTC | TGG | GAG | ATA | TTT | TCA | CTG | GGT | 2694 |
|---|---|---|---|---|---|---|---|---|---|---|---|---|---|---|---|---|

```
              Asp  Val  Trp  Ser  Tyr  Gly  Ile  Leu  Leu  Trp  Glu  Ile  Phe  Ser  Leu  Gly
                   875                      880                     885

GTG  AAC  CCT  TAC  CCT  GGC  ATT  CCT  GTC  GAC  GCT  AAC  TTC  TAT  AAA  CTG            2742
Val  Asn  Pro  Tyr  Pro  Gly  Ile  Pro  Val  Asp  Ala  Asn  Phe  Tyr  Lys  Leu
     890                      895                     900

ATT  CAG  AGT  GGA  TTT  AAA  ATG  GAG  CAG  CCA  TTC  TAT  GCC  ACA  GAA  GGG            2790
Ile  Gln  Ser  Gly  Phe  Lys  Met  Glu  Gln  Pro  Phe  Tyr  Ala  Thr  Glu  Gly
905                      910                     915                      920

ATA  TAC  TTT  GTA  ATG  CAA  TCC  TGC  TGG  GCT  TTT  GAC  TCA  AGG  AAG  CGG            2838
Ile  Tyr  Phe  Val  Met  Gln  Ser  Cys  Trp  Ala  Phe  Asp  Ser  Arg  Lys  Arg
                    925                      930                     935

CCA  TCC  TTC  CCC  AAC  CTG  ACT  TCA  TTT  TTA  GGA  TGT  CAG  CTG  GCA  GAG            2886
Pro  Ser  Phe  Pro  Asn  Leu  Thr  Ser  Phe  Leu  Gly  Cys  Gln  Leu  Ala  Glu
               940                      945                     950

GCA  GAA  GAA  GCA  TGT  ATC  AGA  ACA  TCC  ATC  CAT  CTA  CCA  AAA  CAG  GCG            2934
Ala  Glu  Glu  Ala  Cys  Ile  Arg  Thr  Ser  Ile  His  Leu  Pro  Lys  Gln  Ala
          955                      960                     965

GCC  CCT  CAG  CAG  AGA  GGC  GGG  CTC  AGA  GCC  CAG  TCG  CCA  CAG  CGC  CAG            2982
Ala  Pro  Gln  Gln  Arg  Gly  Gly  Leu  Arg  Ala  Gln  Ser  Pro  Gln  Arg  Gln
     970                      975                     980

GTG  AAG  ATT  CAC  AGA  GAA  AGA  AGT  TAGCGAGGAG GCCTTGGACC CCGCCACCCT                   3036
Val  Lys  Ile  His  Arg  Glu  Arg  Ser
985                      990

AGCAGGCTGT AGACCGCAGA GCCAAGATTA GCCTCGCCTC TGAGGAAGCG CCCTACAGCG                         3096

CGTTGCTTCG CTGGACTTTT CTCTAGATGC TGTCTGCCAT TACTCCAAAG TGACTTCTAT                         3156

AAAATCAAAC CTCTCCTCGC ACAGGCGGGA GAGCCAATAA TGAGACTTGT TGGTGAGCCC                         3216

GCCTACCCTG GGGGCCTTTC CACGAGCTTG AGGGGAAAGC CATGTATCTG AAATATAGTA                         3276

TATTCTTGTA AATACGTGAA ACAAACCAAA CCCGTTTTTT GCTAAGGGAA AGCTAAATAT                         3336

GATTTTTAAA AATCTATGTT TTAAAATACT ATGTAACTTT TTCATCTATT TAGTGATATA                         3396

TTTTATGGAT GGAAATAAAC TTTCTACTGT AAAAAAAAAA AAAAAAAAA AAAAAA                              3453
```

( 2 ) INFORMATION FOR SEQ ID NO:2:

( i ) SEQUENCE CHARACTERISTICS:
        ( A ) LENGTH: 992 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Arg  Ala  Leu  Ala  Gln  Arg  Ser  Asp  Arg  Arg  Leu  Leu  Leu  Leu  Val
 1                  5                      10                      15

Val  Leu  Ser  Val  Met  Ile  Leu  Glu  Thr  Val  Thr  Asn  Gln  Asp  Leu  Pro
               20                      25                      30

Val  Ile  Lys  Cys  Val  Leu  Ile  Ser  His  Glu  Asn  Asn  Gly  Ser  Ser  Ala
          35                      40                      45

Gly  Lys  Pro  Ser  Ser  Tyr  Arg  Met  Val  Arg  Gly  Ser  Pro  Glu  Asp  Leu
     50                      55                      60

Gln  Cys  Thr  Pro  Arg  Arg  Gln  Ser  Glu  Gly  Thr  Val  Tyr  Glu  Ala  Ala
65                       70                      75                       80

Thr  Val  Glu  Val  Ala  Glu  Ser  Gly  Ser  Ile  Thr  Leu  Gln  Val  Gln  Leu
                    85                      90                      95

Ala  Thr  Pro  Gly  Asp  Leu  Ser  Cys  Leu  Trp  Val  Phe  Lys  His  Ser  Ser
               100                      105                     110

Leu  Gly  Cys  Gln  Pro  His  Phe  Asp  Leu  Gln  Asn  Arg  Gly  Ile  Val  Ser
               115                      120                     125
```

```
Met Ala Ile Leu Asn Val Thr Glu Thr Gln Ala Gly Glu Tyr Leu Leu
    130                 135                 140

His Ile Gln Ser Glu Arg Ala Asn Tyr Thr Val Leu Phe Thr Val Asn
145                 150                 155                 160

Val Arg Asp Thr Gln Leu Tyr Val Leu Arg Arg Pro Tyr Phe Arg Lys
                165                 170                 175

Met Glu Asn Gln Asp Ala Leu Leu Cys Ile Ser Glu Gly Val Pro Glu
            180                 185                 190

Pro Thr Val Glu Trp Val Leu Cys Ser Ser His Arg Glu Ser Cys Lys
        195                 200                 205

Glu Glu Gly Pro Ala Val Val Arg Lys Glu Glu Lys Val Leu His Glu
    210                 215                 220

Leu Phe Gly Thr Asp Ile Arg Cys Cys Ala Arg Asn Ala Leu Gly Arg
225                 230                 235                 240

Glu Cys Thr Lys Leu Phe Thr Ile Asp Leu Asn Gln Ala Pro Gln Ser
                245                 250                 255

Thr Leu Pro Gln Leu Phe Leu Lys Val Gly Glu Pro Leu Trp Ile Arg
            260                 265                 270

Cys Lys Ala Ile His Val Asn His Gly Phe Gly Leu Thr Trp Glu Leu
        275                 280                 285

Glu Asp Lys Ala Leu Glu Glu Gly Ser Tyr Phe Glu Met Ser Thr Tyr
    290                 295                 300

Ser Thr Asn Arg Thr Met Ile Arg Ile Leu Leu Ala Phe Val Ser Ser
305                 310                 315                 320

Val Gly Arg Asn Asp Thr Gly Tyr Tyr Thr Cys Ser Ser Ser Lys His
                325                 330                 335

Pro Ser Gln Ser Ala Leu Val Thr Ile Leu Glu Lys Gly Phe Ile Asn
            340                 345                 350

Ala Thr Ser Ser Gln Glu Glu Tyr Glu Ile Asp Pro Tyr Glu Lys Phe
        355                 360                 365

Cys Phe Ser Val Arg Phe Lys Ala Tyr Pro Arg Ile Arg Cys Thr Trp
    370                 375                 380

Ile Phe Ser Gln Ala Ser Phe Pro Cys Glu Gln Arg Gly Leu Glu Asp
385                 390                 395                 400

Gly Tyr Ser Ile Ser Lys Phe Cys Asp His Lys Asn Lys Pro Gly Glu
                405                 410                 415

Tyr Ile Phe Tyr Ala Glu Asn Asp Asp Ala Gln Phe Thr Lys Met Phe
            420                 425                 430

Thr Leu Asn Ile Arg Lys Lys Pro Gln Val Leu Ala Asn Ala Ser Ala
        435                 440                 445

Ser Gln Ala Ser Cys Ser Ser Asp Gly Tyr Pro Leu Pro Ser Trp Thr
    450                 455                 460

Trp Lys Lys Cys Ser Asp Lys Ser Pro Asn Cys Thr Glu Glu Ile Pro
465                 470                 475                 480

Glu Gly Val Trp Asn Lys Lys Ala Asn Arg Lys Val Phe Gly Gln Trp
                485                 490                 495

Val Ser Ser Ser Thr Leu Asn Met Ser Glu Ala Gly Lys Gly Leu Leu
            500                 505                 510

Val Lys Cys Cys Ala Tyr Asn Ser Met Gly Thr Ser Cys Glu Thr Ile
        515                 520                 525

Phe Leu Asn Ser Pro Gly Pro Phe Pro Phe Ile Gln Asp Asn Ile Ser
    530                 535                 540

Phe Tyr Ala Thr Ile Gly Leu Cys Leu Pro Phe Ile Val Val Leu Ile
```

```
545                     550                     555                     560
Val  Leu  Ile  Cys  His  Lys  Tyr  Lys  Lys  Gln  Phe  Arg  Tyr  Glu  Ser  Gln
                    565                     570                     575

Leu  Gln  Met  Ile  Gln  Val  Thr  Gly  Pro  Leu  Asp  Asn  Glu  Tyr  Phe  Tyr
               580                     585                     590

Val  Asp  Phe  Arg  Asp  Tyr  Glu  Tyr  Asp  Leu  Lys  Trp  Glu  Phe  Pro  Arg
               595                     600                     605

Glu  Asn  Leu  Glu  Phe  Gly  Lys  Val  Leu  Gly  Ser  Gly  Ala  Phe  Gly  Arg
          610                     615                     620

Val  Met  Asn  Ala  Thr  Ala  Tyr  Gly  Ile  Ser  Lys  Thr  Gly  Val  Ser  Ile
625                     630                     635                          640

Gln  Val  Ala  Val  Lys  Met  Leu  Lys  Glu  Lys  Ala  Asp  Ser  Cys  Glu  Lys
                    645                     650                     655

Glu  Ala  Leu  Met  Ser  Glu  Leu  Lys  Met  Met  Thr  His  Leu  Gly  His  His
               660                     665                     670

Asp  Asn  Ile  Val  Asn  Leu  Leu  Gly  Ala  Cys  Thr  Leu  Ser  Gly  Pro  Val
          675                     680                     685

Tyr  Leu  Ile  Phe  Glu  Tyr  Cys  Cys  Tyr  Gly  Asp  Leu  Leu  Asn  Tyr  Leu
     690                     695                     700

Arg  Ser  Lys  Arg  Glu  Lys  Phe  His  Arg  Thr  Trp  Thr  Glu  Ile  Phe  Lys
705                     710                     715                          720

Glu  His  Asn  Phe  Ser  Ser  Tyr  Pro  Thr  Phe  Gln  Ala  His  Ser  Asn  Ser
                    725                     730                     735

Ser  Met  Pro  Gly  Ser  Arg  Glu  Val  Gln  Leu  His  Pro  Pro  Leu  Asp  Gln
               740                     745                     750

Leu  Ser  Gly  Phe  Asn  Gly  Asn  Ser  Ile  His  Ser  Glu  Asp  Glu  Ile  Glu
          755                     760                     765

Tyr  Glu  Asn  Gln  Lys  Arg  Leu  Ala  Glu  Glu  Glu  Glu  Asp  Leu  Asn
     770                     775                     780

Val  Leu  Thr  Phe  Glu  Asp  Leu  Leu  Cys  Phe  Ala  Tyr  Gln  Val  Ala  Lys
785                     790                     795                          800

Gly  Met  Glu  Phe  Leu  Glu  Phe  Lys  Ser  Cys  Val  His  Arg  Asp  Leu  Ala
               805                     810                     815

Ala  Arg  Asn  Val  Leu  Val  Thr  His  Gly  Lys  Val  Val  Lys  Ile  Cys  Asp
               820                     825                     830

Phe  Gly  Leu  Ala  Arg  Asp  Ile  Leu  Ser  Asp  Ser  Ser  Tyr  Val  Val  Arg
               835                     840                     845

Gly  Asn  Ala  Arg  Leu  Pro  Val  Lys  Trp  Met  Ala  Pro  Glu  Ser  Leu  Phe
     850                     855                     860

Glu  Gly  Ile  Tyr  Thr  Ile  Lys  Ser  Asp  Val  Trp  Ser  Tyr  Gly  Ile  Leu
865                     870                     875                          880

Leu  Trp  Glu  Ile  Phe  Ser  Leu  Gly  Val  Asn  Pro  Tyr  Pro  Gly  Ile  Pro
               885                     890                     895

Val  Asp  Ala  Asn  Phe  Tyr  Lys  Leu  Ile  Gln  Ser  Gly  Phe  Lys  Met  Glu
               900                     905                     910

Gln  Pro  Phe  Tyr  Ala  Thr  Glu  Gly  Ile  Tyr  Phe  Val  Met  Gln  Ser  Cys
          915                     920                     925

Trp  Ala  Phe  Asp  Ser  Arg  Lys  Arg  Pro  Ser  Phe  Pro  Asn  Leu  Thr  Ser
          930                     935                     940

Phe  Leu  Gly  Cys  Gln  Leu  Ala  Glu  Ala  Glu  Glu  Ala  Cys  Ile  Arg  Thr
945                     950                     955                          960

Ser  Ile  His  Leu  Pro  Lys  Gln  Ala  Ala  Pro  Gln  Gln  Arg  Gly  Gly  Leu
               965                     970                     975
```

| | | | | | | | | | | | | | | |
|---|---|---|---|---|---|---|---|---|---|---|---|---|---|---|
| Arg | Ala | Gln | Ser | Pro | Gln | Arg | Gln | Val | Lys | Ile | His | Arg | Glu | Arg | Ser |
| | | | 980 | | | | | 985 | | | | | 990 | | |

( 2 ) INFORMATION FOR SEQ ID NO:3:

( i ) SEQUENCE CHARACTERISTICS:
        ( A ) LENGTH: 3501 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 58..3039

( x i ) SEQUENCE DESCRIPTION: SEQ ID NO:3:

CGAGGCGGCA TCCGAGGGCT GGGCCGGCGC CCTGGGGGAC CCCGGGCTCC GGAGGCC     57

| | | | | | | | | | | | | | | | |
|---|---|---|---|---|---|---|---|---|---|---|---|---|---|---|---|
| ATG | CCG | GCG | TTG | GCG | CGC | GAC | GCG | GGC | ACC | GTG | CCG | CTG | CTC | GTT | GTT | 105 |
| Met | Pro | Ala | Leu | Ala | Arg | Asp | Ala | Gly | Thr | Val | Pro | Leu | Leu | Val | Val | |
| 1 | | | | 5 | | | | | 10 | | | | | 15 | | |
| TTT | TCT | GCA | ATG | ATA | TTT | GGG | ACT | ATT | ACA | AAT | CAA | GAT | CTG | CCT | GTG | 153 |
| Phe | Ser | Ala | Met | Ile | Phe | Gly | Thr | Ile | Thr | Asn | Gln | Asp | Leu | Pro | Val | |
| | | | 20 | | | | | 25 | | | | | 30 | | | |
| ATC | AAG | TGT | GTT | TTA | ATC | AAT | CAT | AAG | AAC | AAT | GAT | TCA | TCA | GTG | GGG | 201 |
| Ile | Lys | Cys | Val | Leu | Ile | Asn | His | Lys | Asn | Asn | Asp | Ser | Ser | Val | Gly | |
| | | 35 | | | | | 40 | | | | | 45 | | | | |
| AAG | TCA | TCA | TCA | TAT | CCC | ATG | GTA | TCA | GAA | TCC | CCG | GAA | GAC | CTC | GGG | 249 |
| Lys | Ser | Ser | Ser | Tyr | Pro | Met | Val | Ser | Glu | Ser | Pro | Glu | Asp | Leu | Gly | |
| 50 | | | | | 55 | | | | | 60 | | | | | | |
| TGT | GCG | TTG | AGA | CCC | CAG | AGC | TCA | GGG | ACA | GTG | TAC | GAA | GCT | GCC | GCT | 297 |
| Cys | Ala | Leu | Arg | Pro | Gln | Ser | Ser | Gly | Thr | Val | Tyr | Glu | Ala | Ala | Ala | |
| 65 | | | | | 70 | | | | | 75 | | | | | 80 | |
| GTG | GAA | GTG | GAT | GTA | TCT | GCT | TCC | ATC | ACA | CTG | CAA | GTG | CTG | GTC | GAT | 345 |
| Val | Glu | Val | Asp | Val | Ser | Ala | Ser | Ile | Thr | Leu | Gln | Val | Leu | Val | Asp | |
| | | | | 85 | | | | | 90 | | | | | 95 | | |
| GCC | CCA | GGG | AAC | ATT | TCC | TGT | CTC | TGG | GTC | TTT | AAG | CAC | AGC | TCC | CTG | 393 |
| Ala | Pro | Gly | Asn | Ile | Ser | Cys | Leu | Trp | Val | Phe | Lys | His | Ser | Ser | Leu | |
| | | | 100 | | | | | 105 | | | | | 110 | | | |
| AAT | TGC | CAG | CCA | CAT | TTT | GAT | TTA | CAA | AAC | AGA | GGA | GTT | GTT | TCC | ATG | 441 |
| Asn | Cys | Gln | Pro | His | Phe | Asp | Leu | Gln | Asn | Arg | Gly | Val | Val | Ser | Met | |
| | | | 115 | | | | | 120 | | | | | 125 | | | |
| GTC | ATT | TTG | AAA | ATG | ACA | GAA | ACC | CAA | GCT | GGA | GAA | TAC | CTA | CTT | TTT | 489 |
| Val | Ile | Leu | Lys | Met | Thr | Glu | Thr | Gln | Ala | Gly | Glu | Tyr | Leu | Leu | Phe | |
| | | 130 | | | | | 135 | | | | | 140 | | | | |
| ATT | CAG | AGT | GAA | GCT | ACC | AAT | TAC | ACA | ATA | TTG | TTT | ACA | GTG | AGT | ATA | 537 |
| Ile | Gln | Ser | Glu | Ala | Thr | Asn | Tyr | Thr | Ile | Leu | Phe | Thr | Val | Ser | Ile | |
| 145 | | | | | 150 | | | | | 155 | | | | | 160 | |
| AGA | AAT | ACC | CTG | CTT | TAC | ACA | TTA | AGA | AGA | CCT | TAC | TTT | AGA | AAA | ATG | 585 |
| Arg | Asn | Thr | Leu | Leu | Tyr | Thr | Leu | Arg | Arg | Pro | Tyr | Phe | Arg | Lys | Met | |
| | | | | 165 | | | | | 170 | | | | | 175 | | |
| GAA | AAC | CAG | GAC | GCC | CTG | GTC | TGC | ATA | TCT | GAG | AGC | GTT | CCA | GAG | CCG | 633 |
| Glu | Asn | Gln | Asp | Ala | Leu | Val | Cys | Ile | Ser | Glu | Ser | Val | Pro | Glu | Pro | |
| | | | 180 | | | | | 185 | | | | | 190 | | | |
| ATC | GTG | GAA | TGG | GTG | CTT | TGC | GAT | TCA | CAG | GGG | GAA | AGC | TGT | AAA | GAA | 681 |
| Ile | Val | Glu | Trp | Val | Leu | Cys | Asp | Ser | Gln | Gly | Glu | Ser | Cys | Lys | Glu | |
| | | | 195 | | | | | 200 | | | | | 205 | | | |
| GAA | AGT | CCA | GCT | GTT | GTT | AAA | AAG | GAG | GAA | AAA | GTG | CTT | CAT | GAA | TTA | 729 |
| Glu | Ser | Pro | Ala | Val | Val | Lys | Lys | Glu | Glu | Lys | Val | Leu | His | Glu | Leu | |

```
              210                         215                         220
TTT GGG ACG GAC ATA AGG TGC TGT GCC AGA AAT GAA CTG GGC AGG GAA         777
Phe Gly Thr Asp Ile Arg Cys Cys Ala Arg Asn Glu Leu Gly Arg Glu
225                 230                 235                 240

TGC ACC AGG CTG TTC ACA ATA GAT CTA AAT CAA ACT CCT CAG ACC ACA         825
Cys Thr Arg Leu Phe Thr Ile Asp Leu Asn Gln Thr Pro Gln Thr Thr
                245                 250                 255

TTG CCA CAA TTA TTT CTT AAA GTA GGG GAA CCC TTA TGG ATA AGG TGC         873
Leu Pro Gln Leu Phe Leu Lys Val Gly Glu Pro Leu Trp Ile Arg Cys
            260                 265                 270

AAA GCT GTT CAT GTG AAC CAT GGA TTC GGG CTC ACC TGG GAA TTA GAA         921
Lys Ala Val His Val Asn His Gly Phe Gly Leu Thr Trp Glu Leu Glu
        275                 280                 285

AAC AAA GCA CTC GAG GAG GGC AAC TAC TTT GAG ATG AGT ACC TAT TCA         969
Asn Lys Ala Leu Glu Glu Gly Asn Tyr Phe Glu Met Ser Thr Tyr Ser
290                 295                 300

ACA AAC AGA ACT ATG ATA CGG ATT CTG TTT GCT TTT GTA TCA TCA GTG        1017
Thr Asn Arg Thr Met Ile Arg Ile Leu Phe Ala Phe Val Ser Ser Val
305                 310                 315                 320

GCA AGA AAC GAC ACC GGA TAC TAC ACT TGT TCC TCT TCA AAG CAT CCC        1065
Ala Arg Asn Asp Thr Gly Tyr Tyr Thr Cys Ser Ser Ser Lys His Pro
                325                 330                 335

AGT CAA TCA GCT TTG GTT ACC ATC GTA GGA AAG GGA TTT ATA AAT GCT        1113
Ser Gln Ser Ala Leu Val Thr Ile Val Gly Lys Gly Phe Ile Asn Ala
            340                 345                 350

ACC AAT TCA AGT GAA GAT TAT GAA ATT GAC CAA TAT GAA GAG TTT TGT        1161
Thr Asn Ser Ser Glu Asp Tyr Glu Ile Asp Gln Tyr Glu Glu Phe Cys
        355                 360                 365

TTT TCT GTC AGG TTT AAA GCC TAC CCA CAA ATC AGA TGT ACG TGG ACC        1209
Phe Ser Val Arg Phe Lys Ala Tyr Pro Gln Ile Arg Cys Thr Trp Thr
370                 375                 380

TTC TCT CGA AAA TCA TTT CCT TGT GAG CAA AAG GGT CTT GAT AAC GGA        1257
Phe Ser Arg Lys Ser Phe Pro Cys Glu Gln Lys Gly Leu Asp Asn Gly
385                 390                 395                 400

TAC AGC ATA TCC AAG TTT TGC AAT CAT AAG CAC CAG CCA GGA GAA TAT        1305
Tyr Ser Ile Ser Lys Phe Cys Asn His Lys His Gln Pro Gly Glu Tyr
                405                 410                 415

ATA TTC CAT GCA GAA AAT GAT GAT GCC CAA TTT ACC AAA ATG TTC ACG        1353
Ile Phe His Ala Glu Asn Asp Asp Ala Gln Phe Thr Lys Met Phe Thr
            420                 425                 430

CTG AAT ATA AGA AGG AAA CCT CAA GTG CTC GCA GAA GCA TCG GCA AGT        1401
Leu Asn Ile Arg Arg Lys Pro Gln Val Leu Ala Glu Ala Ser Ala Ser
        435                 440                 445

CAG GCG TCC TGT TTC TCG GAT GGA TAC CCA TTA CCA TCT TGG ACC TGG        1449
Gln Ala Ser Cys Phe Ser Asp Gly Tyr Pro Leu Pro Ser Trp Thr Trp
450                 455                 460

AAG AAG TGT TCA GAC AAG TCT CCC AAC TGC ACA GAA GAG ATC ACA GAA        1497
Lys Lys Cys Ser Asp Lys Ser Pro Asn Cys Thr Glu Glu Ile Thr Glu
465                 470                 475                 480

GGA GTC TGG AAT AGA AAG GCT AAC AGA AAA GTG TTT GGA CAG TGG GTG        1545
Gly Val Trp Asn Arg Lys Ala Asn Arg Lys Val Phe Gly Gln Trp Val
                485                 490                 495

TCG AGC AGT ACT CTA AAC ATG AGT GAA GCC ATA AAA GGG TTC CTG GTC        1593
Ser Ser Ser Thr Leu Asn Met Ser Glu Ala Ile Lys Gly Phe Leu Val
            500                 505                 510

AAG TGC TGT GCA TAC AAT TCC CTT GGC ACA TCT TGT GAG ACG ATC CTT        1641
Lys Cys Cys Ala Tyr Asn Ser Leu Gly Thr Ser Cys Glu Thr Ile Leu
        515                 520                 525

TTA AAC TCT CCA GGC CCC TTC CCT TTC ATC CAA GAC AAC ATC TCA TTC        1689
Leu Asn Ser Pro Gly Pro Phe Pro Phe Ile Gln Asp Asn Ile Ser Phe
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 530 |     |     |     |     | 535 |     |     |     |     | 540 |     |     |     |      |
| TAT | GCA | ACA | ATT | GGT | GTT | TGT | CTC | CTC | TTC | ATT | GTC | GTT | TTA | ACC | CTG | 1737 |
| Tyr | Ala | Thr | Ile | Gly | Val | Cys | Leu | Leu | Phe | Ile | Val | Val | Leu | Thr | Leu |      |
| 545 |     |     |     | 550 |     |     |     |     | 555 |     |     |     |     |     | 560 |      |
| CTA | ATT | TGT | CAC | AAG | TAC | AAA | AAG | CAA | TTT | AGG | TAT | GAA | AGC | CAG | CTA | 1785 |
| Leu | Ile | Cys | His | Lys | Tyr | Lys | Lys | Gln | Phe | Arg | Tyr | Glu | Ser | Gln | Leu |      |
|     |     |     |     | 565 |     |     |     |     | 570 |     |     |     |     | 575 |     |      |
| CAG | ATG | GTA | CAG | GTG | ACC | GGC | TCC | TCA | GAT | AAT | GAG | TAC | TTC | TAC | GTT | 1833 |
| Gln | Met | Val | Gln | Val | Thr | Gly | Ser | Ser | Asp | Asn | Glu | Tyr | Phe | Tyr | Val |      |
|     |     |     | 580 |     |     |     |     | 585 |     |     |     |     | 590 |     |     |      |
| GAT | TTC | AGA | GAA | TAT | GAA | TAT | GAT | CTC | AAA | TGG | GAG | TTT | CCA | AGA | GAA | 1881 |
| Asp | Phe | Arg | Glu | Tyr | Glu | Tyr | Asp | Leu | Lys | Trp | Glu | Phe | Pro | Arg | Glu |      |
|     |     | 595 |     |     |     |     | 600 |     |     |     |     | 605 |     |     |     |      |
| AAT | TTA | GAG | TTT | GGG | AAG | GTA | CTA | GGA | TCA | GGT | GCT | TTT | GGA | AAA | GTG | 1929 |
| Asn | Leu | Glu | Phe | Gly | Lys | Val | Leu | Gly | Ser | Gly | Ala | Phe | Gly | Lys | Val |      |
|     | 610 |     |     |     |     | 615 |     |     |     |     | 620 |     |     |     |     |      |
| ATG | AAC | GCA | ACA | GCT | TAT | GGA | ATT | AGC | AAA | ACA | GGA | GTC | TCA | ATC | CAG | 1977 |
| Met | Asn | Ala | Thr | Ala | Tyr | Gly | Ile | Ser | Lys | Thr | Gly | Val | Ser | Ile | Gln |      |
| 625 |     |     |     |     | 630 |     |     |     |     | 635 |     |     |     |     | 640 |      |
| GTT | GCC | GTC | AAA | ATG | CTG | AAA | GAA | AAA | GCA | GAC | AGC | TCT | GAA | AGA | GAG | 2025 |
| Val | Ala | Val | Lys | Met | Leu | Lys | Glu | Lys | Ala | Asp | Ser | Ser | Glu | Arg | Glu |      |
|     |     |     |     | 645 |     |     |     |     | 650 |     |     |     |     | 655 |     |      |
| GCA | CTC | ATG | TCA | GAA | CTC | AAG | ATG | ATG | ACC | CAG | CTG | GGA | AGC | CAC | GAG | 2073 |
| Ala | Leu | Met | Ser | Glu | Leu | Lys | Met | Met | Thr | Gln | Leu | Gly | Ser | His | Glu |      |
|     |     |     | 660 |     |     |     |     | 665 |     |     |     |     | 670 |     |     |      |
| AAT | ATT | GTG | AAC | CTG | CTG | GGG | GCG | TGC | ACA | CTG | TCA | GGA | CCA | ATT | TAC | 2121 |
| Asn | Ile | Val | Asn | Leu | Leu | Gly | Ala | Cys | Thr | Leu | Ser | Gly | Pro | Ile | Tyr |      |
|     |     | 675 |     |     |     |     | 680 |     |     |     |     | 685 |     |     |     |      |
| TTG | ATT | TTT | GAA | TAC | TGT | TGC | TAT | GGT | GAT | CTT | CTC | AAC | TAT | CTA | AGA | 2169 |
| Leu | Ile | Phe | Glu | Tyr | Cys | Cys | Tyr | Gly | Asp | Leu | Leu | Asn | Tyr | Leu | Arg |      |
|     | 690 |     |     |     |     | 695 |     |     |     |     | 700 |     |     |     |     |      |
| AGT | AAA | AGA | GAA | AAA | TTT | CAC | AGG | ACT | TGG | ACA | GAG | ATT | TTC | AAG | GAA | 2217 |
| Ser | Lys | Arg | Glu | Lys | Phe | His | Arg | Thr | Trp | Thr | Glu | Ile | Phe | Lys | Glu |      |
| 705 |     |     |     |     | 710 |     |     |     |     | 715 |     |     |     |     | 720 |      |
| CAC | AAT | TTC | AGT | TTT | TAC | CCC | ACT | TTC | CAA | TCA | CAT | CCA | AAT | TCC | AGC | 2265 |
| His | Asn | Phe | Ser | Phe | Tyr | Pro | Thr | Phe | Gln | Ser | His | Pro | Asn | Ser | Ser |      |
|     |     |     |     | 725 |     |     |     |     | 730 |     |     |     |     | 735 |     |      |
| ATG | CCT | GGT | TCA | AGA | GAA | GTT | CAG | ATA | CAC | CCG | GAC | TCG | GAT | CAA | ATC | 2313 |
| Met | Pro | Gly | Ser | Arg | Glu | Val | Gln | Ile | His | Pro | Asp | Ser | Asp | Gln | Ile |      |
|     |     |     | 740 |     |     |     |     | 745 |     |     |     |     | 750 |     |     |      |
| TCA | GGG | CTT | CAT | GGG | AAT | TCA | TTT | CAC | TCT | GAA | GAT | GAA | ATT | GAA | TAT | 2361 |
| Ser | Gly | Leu | His | Gly | Asn | Ser | Phe | His | Ser | Glu | Asp | Glu | Ile | Glu | Tyr |      |
|     |     | 755 |     |     |     |     | 760 |     |     |     |     | 765 |     |     |     |      |
| GAA | AAC | CAA | AAA | AGG | CTG | GAA | GAA | GAG | GAG | GAC | TTG | AAT | GTG | CTT | ACA | 2409 |
| Glu | Asn | Gln | Lys | Arg | Leu | Glu | Glu | Glu | Glu | Asp | Leu | Asn | Val | Leu | Thr |      |
| 770 |     |     |     |     | 775 |     |     |     |     | 780 |     |     |     |     |     |      |
| TTT | GAA | GAT | CTT | CTT | TGC | TTT | GCA | TAT | CAA | GTT | GCC | AAA | GGA | ATG | GAA | 2457 |
| Phe | Glu | Asp | Leu | Leu | Cys | Phe | Ala | Tyr | Gln | Val | Ala | Lys | Gly | Met | Glu |      |
| 785 |     |     |     |     | 790 |     |     |     |     | 795 |     |     |     |     | 800 |      |
| TTT | CTG | GAA | TTT | AAG | TCG | TGT | GTT | CAC | AGA | GAC | CTG | GCC | GCC | AGG | AAC | 2505 |
| Phe | Leu | Glu | Phe | Lys | Ser | Cys | Val | His | Arg | Asp | Leu | Ala | Ala | Arg | Asn |      |
|     |     |     |     | 805 |     |     |     |     | 810 |     |     |     |     | 815 |     |      |
| GTG | CTT | GTC | ACC | CAC | GGG | AAA | GTG | GTG | AAG | ATA | TGT | GAC | TTT | GGA | TTG | 2553 |
| Val | Leu | Val | Thr | His | Gly | Lys | Val | Val | Lys | Ile | Cys | Asp | Phe | Gly | Leu |      |
|     |     |     | 820 |     |     |     |     | 825 |     |     |     |     | 830 |     |     |      |
| GCT | CGA | GAT | ATC | ATG | AGT | GAT | TCC | AAC | TAT | GTT | GTC | AGG | GGC | AAT | GCC | 2601 |
| Ala | Arg | Asp | Ile | Met | Ser | Asp | Ser | Asn | Tyr | Val | Val | Arg | Gly | Asn | Ala |      |
|     |     | 835 |     |     |     |     | 840 |     |     |     |     | 845 |     |     |     |      |
| CGT | CTG | CCT | GTA | AAA | TGG | ATG | GCC | CCC | GAA | AGC | CTG | TTT | GAA | GGC | ATC | 2649 |
| Arg | Leu | Pro | Val | Lys | Trp | Met | Ala | Pro | Glu | Ser | Leu | Phe | Glu | Gly | Ile |      |

|  |  |  |  |  |  |  |  |  |  |  |  |  |  |  |  |  |
|---|---|---|---|---|---|---|---|---|---|---|---|---|---|---|---|---|
|  | 850 |  |  |  |  | 855 |  |  |  |  | 860 |  |  |  |  |  |
| TAC | ACC | ATT | AAG | AGT | GAT | GTC | TGG | TCA | TAT | GGA | ATA | TTA | CTG | TGG | GAA | 2697 |
| Tyr | Thr | Ile | Lys | Ser | Asp | Val | Trp | Ser | Tyr | Gly | Ile | Leu | Leu | Trp | Glu |  |
| 865 |  |  |  |  | 870 |  |  |  |  | 875 |  |  |  |  | 880 |  |
| ATC | TTC | TCA | CTT | GGT | GTG | AAT | CCT | TAC | CCT | GGC | ATT | CCG | GTT | GAT | GCT | 2745 |
| Ile | Phe | Ser | Leu | Gly | Val | Asn | Pro | Tyr | Pro | Gly | Ile | Pro | Val | Asp | Ala |  |
|  |  |  |  | 885 |  |  |  |  | 890 |  |  |  |  | 895 |  |  |
| AAC | TTC | TAC | AAA | CTG | ATT | CAA | AAT | GGA | TTT | AAA | ATG | GAT | CAG | CCA | TTT | 2793 |
| Asn | Phe | Tyr | Lys | Leu | Ile | Gln | Asn | Gly | Phe | Lys | Met | Asp | Gln | Pro | Phe |  |
|  |  |  | 900 |  |  |  |  | 905 |  |  |  |  | 910 |  |  |  |
| TAT | GCT | ACA | GAA | GAA | ATA | TAC | ATT | ATA | ATG | CAA | TCC | TGC | TGG | GCT | TTT | 2841 |
| Tyr | Ala | Thr | Glu | Glu | Ile | Tyr | Ile | Ile | Met | Gln | Ser | Cys | Trp | Ala | Phe |  |
|  |  | 915 |  |  |  |  | 920 |  |  |  |  | 925 |  |  |  |  |
| GAC | TCA | AGG | AAA | CGG | CCA | TCC | TTC | CCT | AAT | TTG | ACT | TCG | TTT | TTA | GGA | 2889 |
| Asp | Ser | Arg | Lys | Arg | Pro | Ser | Phe | Pro | Asn | Leu | Thr | Ser | Phe | Leu | Gly |  |
|  | 930 |  |  |  |  | 935 |  |  |  |  | 940 |  |  |  |  |  |
| TGT | CAG | CTG | GCA | GAT | GCA | GAA | GAA | GCG | ATG | TAT | CAG | AAT | GTG | GAT | GGC | 2937 |
| Cys | Gln | Leu | Ala | Asp | Ala | Glu | Glu | Ala | Met | Tyr | Gln | Asn | Val | Asp | Gly |  |
| 945 |  |  |  |  | 950 |  |  |  |  | 955 |  |  |  |  | 960 |  |
| CGT | GTT | TCG | GAA | TGT | CCT | CAC | ACC | TAC | CAA | AAC | AGG | CGA | CCT | TTC | AGC | 2985 |
| Arg | Val | Ser | Glu | Cys | Pro | His | Thr | Tyr | Gln | Asn | Arg | Arg | Pro | Phe | Ser |  |
|  |  |  |  | 965 |  |  |  |  | 970 |  |  |  |  | 975 |  |  |
| AGA | GAG | ATG | GAT | TTG | GGG | CTA | CTC | TCT | CCG | CAG | GCT | CAG | GTC | GAA | GAT | 3033 |
| Arg | Glu | Met | Asp | Leu | Gly | Leu | Leu | Ser | Pro | Gln | Ala | Gln | Val | Glu | Asp |  |
|  |  |  | 980 |  |  |  |  | 985 |  |  |  |  | 990 |  |  |  |
| TCG | TAGAGGAACA | ATTTAGTTTT | AAGGACTTCA | TCCCTCCACC | TATCCCTAAC |  |  |  |  |  |  |  |  |  |  | 3086 |
| Ser |  |  |  |  |  |  |  |  |  |  |  |  |  |  |  |  |
| AGGCTGTAGA | TTACCAAAAC | AAGATTAATT | TCATCACTAA | AAGAAAATCT | ATTATCAACT |  |  |  |  |  |  |  |  |  |  | 3146 |
| GCTGCTTCAC | CAGACTTTTC | TCTAGAAGCC | GTCTGCGTTT | ACTCTTGTTT | TCAAAGGGAC |  |  |  |  |  |  |  |  |  |  | 3206 |
| TTTTGTAAAA | TCAAATCATC | CTGTCACAAG | GCAGGAGGAG | CTGATAATGA | ACTTTATTGG |  |  |  |  |  |  |  |  |  |  | 3266 |
| AGCATTGATC | TGCATCCAAG | GCCTTCTCAG | GCCGGCTTGA | GTGAATTGTG | TACCTGAAGT |  |  |  |  |  |  |  |  |  |  | 3326 |
| ACAGTATATT | CTTGTAAATA | CATAAAACAA | AAGCATTTTG | CTAAGGAGAA | GCTAATATGA |  |  |  |  |  |  |  |  |  |  | 3386 |
| TTTTTTAAGT | CTATGTTTTA | AAATAATATG | TAAATTTTTC | AGCTATTTAG | TGATATATTT |  |  |  |  |  |  |  |  |  |  | 3446 |
| TATGGGTGGG | AATAAAATTT | CTACTACAGA | AAAAAAAAAA | AAAAAAAAAA | AAAAA |  |  |  |  |  |  |  |  |  |  | 3501 |

( 2 ) INFORMATION FOR SEQ ID NO:4:

( i ) SEQUENCE CHARACTERISTICS:
        ( A ) LENGTH: 993 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Pro | Ala | Leu | Ala | Arg | Asp | Ala | Gly | Thr | Val | Pro | Leu | Leu | Val | Val |
|---|---|---|---|---|---|---|---|---|---|---|---|---|---|---|---|
| 1 |  |  |  | 5 |  |  |  |  | 10 |  |  |  |  | 15 |  |
| Phe | Ser | Ala | Met | Ile | Phe | Gly | Thr | Ile | Thr | Asn | Gln | Asp | Leu | Pro | Val |
|  |  |  | 20 |  |  |  |  | 25 |  |  |  |  | 30 |  |  |
| Ile | Lys | Cys | Val | Leu | Ile | Asn | His | Lys | Asn | Asn | Asp | Ser | Ser | Val | Gly |
|  |  | 35 |  |  |  |  | 40 |  |  |  |  | 45 |  |  |  |
| Lys | Ser | Ser | Ser | Tyr | Pro | Met | Val | Ser | Glu | Ser | Pro | Glu | Asp | Leu | Gly |
|  | 50 |  |  |  |  | 55 |  |  |  |  | 60 |  |  |  |  |
| Cys | Ala | Leu | Arg | Pro | Gln | Ser | Ser | Gly | Thr | Val | Tyr | Glu | Ala | Ala | Ala |
| 65 |  |  |  |  | 70 |  |  |  |  | 75 |  |  |  |  | 80 |
| Val | Glu | Val | Asp | Val | Ser | Ala | Ser | Ile | Thr | Leu | Gln | Val | Leu | Val | Asp |
|  |  |  |  | 85 |  |  |  |  | 90 |  |  |  |  | 95 |  |

```
Ala Pro Gly Asn Ile Ser Cys Leu Trp Val Phe Lys His Ser Ser Leu
            100                 105                 110
Asn Cys Gln Pro His Phe Asp Leu Gln Asn Arg Gly Val Val Ser Met
        115                 120                 125
Val Ile Leu Lys Met Thr Glu Thr Gln Ala Gly Glu Tyr Leu Leu Phe
    130                 135                 140
Ile Gln Ser Glu Ala Thr Asn Tyr Thr Ile Leu Phe Thr Val Ser Ile
145                 150                 155                 160
Arg Asn Thr Leu Leu Tyr Thr Leu Arg Arg Pro Tyr Phe Arg Lys Met
                165                 170                 175
Glu Asn Gln Asp Ala Leu Val Cys Ile Ser Glu Ser Val Pro Glu Pro
            180                 185                 190
Ile Val Glu Trp Val Leu Cys Asp Ser Gln Gly Glu Ser Cys Lys Glu
        195                 200                 205
Glu Ser Pro Ala Val Val Lys Lys Glu Glu Lys Val Leu His Glu Leu
    210                 215                 220
Phe Gly Thr Asp Ile Arg Cys Cys Ala Arg Asn Glu Leu Gly Arg Glu
225                 230                 235                 240
Cys Thr Arg Leu Phe Thr Ile Asp Leu Asn Gln Thr Pro Gln Thr Thr
                245                 250                 255
Leu Pro Gln Leu Phe Leu Lys Val Gly Glu Pro Leu Trp Ile Arg Cys
            260                 265                 270
Lys Ala Val His Val Asn His Gly Phe Gly Leu Thr Trp Glu Leu Glu
        275                 280                 285
Asn Lys Ala Leu Glu Glu Gly Asn Tyr Phe Glu Met Ser Thr Tyr Ser
    290                 295                 300
Thr Asn Arg Thr Met Ile Arg Ile Leu Phe Ala Phe Val Ser Ser Val
305                 310                 315                 320
Ala Arg Asn Asp Thr Gly Tyr Tyr Thr Cys Ser Ser Ser Lys His Pro
                325                 330                 335
Ser Gln Ser Ala Leu Val Thr Ile Val Gly Lys Gly Phe Ile Asn Ala
            340                 345                 350
Thr Asn Ser Ser Glu Asp Tyr Glu Ile Asp Gln Tyr Glu Glu Phe Cys
        355                 360                 365
Phe Ser Val Arg Phe Lys Ala Tyr Pro Gln Ile Arg Cys Thr Trp Thr
    370                 375                 380
Phe Ser Arg Lys Ser Phe Pro Cys Glu Gln Lys Gly Leu Asp Asn Gly
385                 390                 395                 400
Tyr Ser Ile Ser Lys Phe Cys Asn His Lys His Gln Pro Gly Glu Tyr
                405                 410                 415
Ile Phe His Ala Glu Asn Asp Asp Ala Gln Phe Thr Lys Met Phe Thr
            420                 425                 430
Leu Asn Ile Arg Arg Lys Pro Gln Val Leu Ala Glu Ala Ser Ala Ser
        435                 440                 445
Gln Ala Ser Cys Phe Ser Asp Gly Tyr Pro Leu Pro Ser Trp Thr Trp
    450                 455                 460
Lys Lys Cys Ser Asp Lys Ser Pro Asn Cys Thr Glu Glu Ile Thr Glu
465                 470                 475                 480
Gly Val Trp Asn Arg Lys Ala Asn Arg Lys Val Phe Gly Gln Trp Val
                485                 490                 495
Ser Ser Ser Thr Leu Asn Met Ser Glu Ala Ile Lys Gly Phe Leu Val
            500                 505                 510
Lys Cys Cys Ala Tyr Asn Ser Leu Gly Thr Ser Cys Glu Thr Ile Leu
```

-continued

|  |  | 515 |  |  |  | 520 |  |  |  | 525 |  |  |  |
|---|---|---|---|---|---|---|---|---|---|---|---|---|---|
| Leu | Asn | Ser | Pro | Gly | Pro | Phe | Pro | Phe | Ile | Gln | Asp | Asn | Ile | Ser | Phe |
|  |  | 530 |  |  |  | 535 |  |  |  | 540 |  |  |  |
| Tyr | Ala | Thr | Ile | Gly | Val | Cys | Leu | Leu | Phe | Ile | Val | Val | Leu | Thr | Leu |
| 545 |  |  |  |  | 550 |  |  |  | 555 |  |  |  |  |  | 560 |
| Leu | Ile | Cys | His | Lys | Tyr | Lys | Lys | Gln | Phe | Arg | Tyr | Glu | Ser | Gln | Leu |
|  |  |  |  | 565 |  |  |  | 570 |  |  |  |  |  | 575 |  |
| Gln | Met | Val | Gln | Val | Thr | Gly | Ser | Ser | Asp | Asn | Glu | Tyr | Phe | Tyr | Val |
|  |  |  | 580 |  |  |  |  | 585 |  |  |  |  | 590 |  |  |
| Asp | Phe | Arg | Glu | Tyr | Glu | Tyr | Asp | Leu | Lys | Trp | Glu | Phe | Pro | Arg | Glu |
|  |  | 595 |  |  |  |  | 600 |  |  |  |  | 605 |  |  |  |
| Asn | Leu | Glu | Phe | Gly | Lys | Val | Leu | Gly | Ser | Gly | Ala | Phe | Gly | Lys | Val |
|  | 610 |  |  |  |  | 615 |  |  |  |  | 620 |  |  |  |  |
| Met | Asn | Ala | Thr | Ala | Tyr | Gly | Ile | Ser | Lys | Thr | Gly | Val | Ser | Ile | Gln |
| 625 |  |  |  |  | 630 |  |  |  |  | 635 |  |  |  |  | 640 |
| Val | Ala | Val | Lys | Met | Leu | Lys | Glu | Lys | Ala | Asp | Ser | Ser | Glu | Arg | Glu |
|  |  |  |  | 645 |  |  |  |  | 650 |  |  |  |  | 655 |  |
| Ala | Leu | Met | Ser | Glu | Leu | Lys | Met | Met | Thr | Gln | Leu | Gly | Ser | His | Glu |
|  |  |  | 660 |  |  |  |  | 665 |  |  |  |  | 670 |  |  |
| Asn | Ile | Val | Asn | Leu | Leu | Gly | Ala | Cys | Thr | Leu | Ser | Gly | Pro | Ile | Tyr |
|  |  | 675 |  |  |  |  | 680 |  |  |  |  | 685 |  |  |  |
| Leu | Ile | Phe | Glu | Tyr | Cys | Cys | Tyr | Gly | Asp | Leu | Leu | Asn | Tyr | Leu | Arg |
|  | 690 |  |  |  |  | 695 |  |  |  |  | 700 |  |  |  |  |
| Ser | Lys | Arg | Glu | Lys | Phe | His | Arg | Thr | Trp | Thr | Glu | Ile | Phe | Lys | Glu |
| 705 |  |  |  |  | 710 |  |  |  |  | 715 |  |  |  |  | 720 |
| His | Asn | Phe | Ser | Phe | Tyr | Pro | Thr | Phe | Gln | Ser | His | Pro | Asn | Ser | Ser |
|  |  |  |  | 725 |  |  |  |  | 730 |  |  |  |  | 735 |  |
| Met | Pro | Gly | Ser | Arg | Glu | Val | Gln | Ile | His | Pro | Asp | Ser | Asp | Gln | Ile |
|  |  |  | 740 |  |  |  |  | 745 |  |  |  |  | 750 |  |  |
| Ser | Gly | Leu | His | Gly | Asn | Ser | Phe | His | Ser | Glu | Asp | Glu | Ile | Glu | Tyr |
|  |  | 755 |  |  |  |  | 760 |  |  |  |  | 765 |  |  |  |
| Glu | Asn | Gln | Lys | Arg | Leu | Glu | Glu | Glu | Glu | Asp | Leu | Asn | Val | Leu | Thr |
|  | 770 |  |  |  |  | 775 |  |  |  |  | 780 |  |  |  |  |
| Phe | Glu | Asp | Leu | Leu | Cys | Phe | Ala | Tyr | Gln | Val | Ala | Lys | Gly | Met | Glu |
| 785 |  |  |  |  | 790 |  |  |  |  | 795 |  |  |  |  | 800 |
| Phe | Leu | Glu | Phe | Lys | Ser | Cys | Val | His | Arg | Asp | Leu | Ala | Ala | Arg | Asn |
|  |  |  |  | 805 |  |  |  |  | 810 |  |  |  |  | 815 |  |
| Val | Leu | Val | Thr | His | Gly | Lys | Val | Val | Lys | Ile | Cys | Asp | Phe | Gly | Leu |
|  |  |  | 820 |  |  |  |  | 825 |  |  |  |  | 830 |  |  |
| Ala | Arg | Asp | Ile | Met | Ser | Asp | Ser | Asn | Tyr | Val | Val | Arg | Gly | Asn | Ala |
|  |  | 835 |  |  |  |  | 840 |  |  |  |  | 845 |  |  |  |
| Arg | Leu | Pro | Val | Lys | Trp | Met | Ala | Pro | Glu | Ser | Leu | Phe | Glu | Gly | Ile |
|  | 850 |  |  |  |  | 855 |  |  |  |  | 860 |  |  |  |  |
| Tyr | Thr | Ile | Lys | Ser | Asp | Val | Trp | Ser | Tyr | Gly | Ile | Leu | Leu | Trp | Glu |
| 865 |  |  |  |  | 870 |  |  |  |  | 875 |  |  |  |  | 880 |
| Ile | Phe | Ser | Leu | Gly | Val | Asn | Pro | Tyr | Pro | Gly | Ile | Pro | Val | Asp | Ala |
|  |  |  |  | 885 |  |  |  |  | 890 |  |  |  |  | 895 |  |
| Asn | Phe | Tyr | Lys | Leu | Ile | Gln | Asn | Gly | Phe | Lys | Met | Asp | Gln | Pro | Phe |
|  |  |  | 900 |  |  |  |  | 905 |  |  |  |  | 910 |  |  |
| Tyr | Ala | Thr | Glu | Glu | Ile | Tyr | Ile | Ile | Met | Gln | Ser | Cys | Trp | Ala | Phe |
|  |  |  | 915 |  |  |  |  | 920 |  |  |  |  | 925 |  |  |
| Asp | Ser | Arg | Lys | Arg | Pro | Ser | Phe | Pro | Asn | Leu | Thr | Ser | Phe | Leu | Gly |
|  |  | 930 |  |  |  |  | 935 |  |  |  |  | 940 |  |  |  |

| | | | | | | | | | | | | | | | |
|---|---|---|---|---|---|---|---|---|---|---|---|---|---|---|---|
| Cys | Gln | Leu | Ala | Asp | Ala | Glu | Glu | Ala | Met | Tyr | Gln | Asn | Val | Asp | Gly |
| 945 | | | | | 950 | | | | | 955 | | | | | 960 |
| Arg | Val | Ser | Glu | Cys | Pro | His | Thr | Tyr | Gln | Asn | Arg | Arg | Pro | Phe | Ser |
| | | | | 965 | | | | | 970 | | | | | 975 | |
| Arg | Glu | Met | Asp | Leu | Gly | Leu | Leu | Ser | Pro | Gln | Ala | Gln | Val | Glu | Asp |
| | | | 980 | | | | | 985 | | | | | 990 | | |
| Ser | | | | | | | | | | | | | | | |

( 2 ) INFORMATION FOR SEQ ID NO:5:

( i ) SEQUENCE CHARACTERISTICS:
        ( A ) LENGTH: 5406 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( i x ) FEATURE:
        ( A ) NAME/KEY: CDS
        ( B ) LOCATION: 208..4311

( i x ) FEATURE:
        ( A ) NAME/KEY: mat_peptide
        ( B ) LOCATION: 208..4308

( x i ) SEQUENCE DESCRIPTION: SEQ ID NO:5:

```
CTGTGTCCCG CAGCCGGATA ACCTGGCTGA CCCGATTCCG CGGACACCCG TGCAGCCGCG      60

GCTGGAGCCA GGGCGCCGGT GCCCGCGCTC TCCCCGGTCT TGCGCTGCGG GGGCCGATAC     120

CGCCTCTGTG ACTTCTTTGC GGGCCAGGGA CGGAGAAGGA GTCTGTGCCT GAGAAACTGG     180

GCTCTGTGCC CAGGCGCGAG GTGCAGG ATG GAG AGC AAG GGC CTG CTA GCT         231
                              Met Glu Ser Lys Gly Leu Leu Ala
                                1               5
```

| CTG | GCT | CTG | TGG | TTC | TGC | GTG | GAG | ACC | CGA | GCC | GCC | TCT | GTG | GGT | TTG | 279 |
|---|---|---|---|---|---|---|---|---|---|---|---|---|---|---|---|---|
| Val | Ala | Leu | Trp | Phe | Cys | Val | Glu | Thr | Arg | Ala | Ala | Ser | Val | Gly | Leu | |
| | 10 | | | | 15 | | | | | 20 | | | | | | |

| CCT | GGC | GAT | TTT | CTC | CAT | CCC | CCC | AAG | CTC | AGC | ACA | CAG | AAA | GAC | ATA | 327 |
|---|---|---|---|---|---|---|---|---|---|---|---|---|---|---|---|---|
| Pro | Gly | Asp | Phe | Leu | His | Pro | Pro | Lys | Leu | Ser | Thr | Gln | Lys | Asp | Ile | |
| 25 | | | | | 30 | | | | 35 | | | | | | 40 | |

| CTG | ACA | ATT | TTG | GCA | AAT | ACA | ACC | CTT | CAG | ATT | ACT | TGC | AGG | GGA | CAG | 375 |
|---|---|---|---|---|---|---|---|---|---|---|---|---|---|---|---|---|
| Leu | Thr | Ile | Leu | Ala | Asn | Thr | Thr | Leu | Gln | Ile | Thr | Cys | Arg | Gly | Gln | |
| | | | | 45 | | | | | 50 | | | | | 55 | | |

| CGG | GAC | CTG | GAC | TGG | CTT | TGG | CCC | AAT | GCT | CAG | CGT | GAT | TCT | GAG | GAA | 423 |
|---|---|---|---|---|---|---|---|---|---|---|---|---|---|---|---|---|
| Arg | Asp | Leu | Asp | Trp | Leu | Trp | Pro | Asn | Ala | Gln | Arg | Asp | Ser | Glu | Glu | |
| | | | 60 | | | | | 65 | | | | | 70 | | | |

| AGG | GTA | TTG | GTG | ACT | GAA | TGC | GGC | GGT | GGT | GAC | AGT | ATC | TTC | TGC | AAA | 471 |
|---|---|---|---|---|---|---|---|---|---|---|---|---|---|---|---|---|
| Arg | Val | Leu | Val | Thr | Glu | Cys | Gly | Gly | Gly | Asp | Ser | Ile | Phe | Cys | Lys | |
| | | 75 | | | | | 80 | | | | | 85 | | | | |

| ACA | CTC | ACC | ATT | CCC | AGG | GTG | GTT | GGA | AAT | GAT | ACT | GGA | GCC | TAC | AAG | 519 |
|---|---|---|---|---|---|---|---|---|---|---|---|---|---|---|---|---|
| Thr | Leu | Thr | Ile | Pro | Arg | Val | Val | Gly | Asn | Asp | Thr | Gly | Ala | Tyr | Lys | |
| | 90 | | | | | 95 | | | | | 100 | | | | | |

| TGC | TCG | TAC | CGG | GAC | GTC | GAC | ATA | GCC | TCC | ACT | GTT | TAT | GTC | TAT | GTT | 567 |
|---|---|---|---|---|---|---|---|---|---|---|---|---|---|---|---|---|
| Cys | Ser | Tyr | Arg | Asp | Val | Asp | Ile | Ala | Ser | Thr | Val | Tyr | Val | Tyr | Val | |
| 105 | | | | | 110 | | | | 115 | | | | | | 120 | |

| CGA | GAT | TAC | AGA | TCA | CCA | TTC | ATC | GCC | TCT | GTC | AGT | GAC | CAG | CAT | GGC | 615 |
|---|---|---|---|---|---|---|---|---|---|---|---|---|---|---|---|---|
| Arg | Asp | Tyr | Arg | Ser | Pro | Phe | Ile | Ala | Ser | Val | Ser | Asp | Gln | His | Gly | |
| | | | | 125 | | | | | 130 | | | | | 135 | | |

| | | | | | | | | | | | | | | | | |
|---|---|---|---|---|---|---|---|---|---|---|---|---|---|---|---|---|
| ATC | GTG | TAC | ATC | ACC | GAG | AAC | AAG | AAC | AAA | ACT | GTG | GTG | ATC | CCC | TGC | 663 |
| Ile | Val | Tyr | Ile 140 | Thr | Glu | Asn | Lys | Asn 145 | Lys | Thr | Val | Val | Ile 150 | Pro | Cys | |
| CGA | GGG | TCG | ATT | TCA | AAC | CTC | AAT | GTG | TCT | CTT | TGC | GCT | AGG | TAT | CCA | 711 |
| Arg | Gly | Ser 155 | Ile | Ser | Asn | Leu | Asn 160 | Val | Ser | Leu | Cys | Ala | Arg 165 | Tyr | Pro | |
| GAA | AAG | AGA | TTT | GTT | CCG | GAT | GGA | AAC | AGA | ATT | TCC | TGG | GAC | AGC | GAG | 759 |
| Glu | Lys 170 | Arg | Phe | Val | Pro | Asp 175 | Gly | Asn | Arg | Ile | Ser 180 | Trp | Asp | Ser | Glu | |
| ATA | GGC | TTT | ACT | CTC | CCC | AGT | TAC | ATG | ATC | AGC | TAT | GCC | GGC | ATG | GTC | 807 |
| Ile 185 | Gly | Phe | Thr | Leu | Pro 190 | Ser | Tyr | Met | Ile | Ser 195 | Tyr | Ala | Gly | Met | Val 200 | |
| TTC | TGT | GAG | GCA | AAG | ATC | AAT | GAT | GAA | ACC | TAT | CAG | TCT | ATC | ATG | TAC | 855 |
| Phe | Cys | Glu | Ala | Lys 205 | Ile | Asn | Asp | Glu | Thr 210 | Tyr | Gln | Ser | Ile | Met 215 | Tyr | |
| ATA | GTT | GTG | GTT | GTA | GGA | TAT | AGG | ATT | TAT | GAT | GTG | ATT | CTG | AGC | CCC | 903 |
| Ile | Val | Val | Val 220 | Val | Gly | Tyr | Arg | Ile 225 | Tyr | Asp | Val | Ile | Leu 230 | Ser | Pro | |
| CCG | CAT | GAA | ATT | GAG | CTA | TCT | GCC | GGA | GAA | AAA | CTT | GTC | TTA | AAT | TGT | 951 |
| Pro | His | Glu 235 | Ile | Glu | Leu | Ser | Ala 240 | Gly | Glu | Lys | Leu | Val 245 | Leu | Asn | Cys | |
| ACA | GCG | AGA | ACA | GAG | CTC | AAT | GTG | GGG | CTT | GAT | TTC | ACC | TGG | CAC | TCT | 999 |
| Thr | Ala 250 | Arg | Thr | Glu | Leu | Asn 255 | Val | Gly | Leu | Asp | Phe 260 | Thr | Trp | His | Ser | |
| CCA | CCT | TCA | AAG | TCT | CAT | CAT | AAG | AAG | ATT | GTA | AAC | CGG | GAT | GTG | AAA | 1047 |
| Pro 265 | Pro | Ser | Lys | Ser | His 270 | His | Lys | Lys | Ile | Val 275 | Asn | Arg | Asp | Val | Lys 280 | |
| CCC | TTT | CCT | GGG | ACT | GTG | GCG | AAG | ATG | TTT | TTG | AGC | ACC | TTG | ACA | ATA | 1095 |
| Pro | Phe | Pro | Gly | Thr 285 | Val | Ala | Lys | Met | Phe 290 | Leu | Ser | Thr | Leu | Thr 295 | Ile | |
| GAA | AGT | GTG | ACC | AAG | AGT | GAC | CAA | GGG | GAA | TAC | ACC | TGT | GTA | GCG | TCC | 1143 |
| Glu | Ser | Val | Thr 300 | Lys | Ser | Asp | Gln | Gly 305 | Glu | Tyr | Thr | Cys | Val 310 | Ala | Ser | |
| AGT | GGA | CGG | ATG | ATC | AAG | AGA | AAT | AGA | ACA | TTT | GTC | CGA | GTT | CAC | ACA | 1191 |
| Ser | Gly | Arg 315 | Met | Ile | Lys | Arg | Asn 320 | Arg | Thr | Phe | Val | Arg 325 | Val | His | Thr | |
| AAG | CCT | TTT | ATT | GCT | TTC | GGT | AGT | GGG | ATG | AAA | TCT | TTG | GTG | GAA | GCC | 1239 |
| Lys | Pro 330 | Phe | Ile | Ala | Phe | Gly 335 | Ser | Gly | Met | Lys | Ser 340 | Leu | Val | Glu | Ala | |
| ACA | GTG | GGC | AGT | CAA | GTC | CGA | ATC | CCT | GTG | AAG | TAT | CTC | AGT | TAC | CCA | 1287 |
| Thr 345 | Val | Gly | Ser | Gln | Val 350 | Arg | Ile | Pro | Val | Lys 355 | Tyr | Leu | Ser | Tyr | Pro 360 | |
| GCT | CCT | GAT | ATC | AAA | TGG | TAC | AGA | AAT | GGA | AGG | CCC | ATT | GAG | TCC | AAC | 1335 |
| Ala | Pro | Asp | Ile | Lys 365 | Trp | Tyr | Arg | Asn | Gly 370 | Arg | Pro | Ile | Glu | Ser 375 | Asn | |
| TAC | ACA | ATG | ATT | GTT | GGC | GAT | GAA | CTC | ACC | ATC | ATG | GAA | GTG | ACT | GAA | 1383 |
| Tyr | Thr | Met | Ile 380 | Val | Gly | Asp | Glu | Leu 385 | Thr | Ile | Met | Glu | Val 390 | Thr | Glu | |
| AGA | GAT | GCA | GGA | AAC | TAC | ACG | GTC | ATC | CTC | ACC | AAC | CCC | ATT | TCA | ATG | 1431 |
| Arg | Asp | Ala 395 | Gly | Asn | Tyr | Thr | Val 400 | Ile | Leu | Thr | Asn | Pro 405 | Ile | Ser | Met | |
| GAG | AAA | CAG | AGC | CAC | ATG | GTC | TCT | CTG | GTT | GTG | AAT | GTC | CCA | CCC | CAG | 1479 |
| Glu | Lys 410 | Gln | Ser | His | Met | Val 415 | Ser | Leu | Val | Val | Asn 420 | Val | Pro | Pro | Gln | |
| ATC | GGT | GAG | AAA | GCC | TTG | ATC | TCG | CCT | ATG | GAT | TCC | TAC | CAG | TAT | GGG | 1527 |
| Ile | Gly | Glu | Lys 425 | Ala | Leu | Ile | Ser | Pro 430 | Met | Asp | Ser | Tyr | Gln 435 | Tyr | Gly | Gly 440 |
| ACC | ATG | CAG | ACA | TTG | ACA | TGC | ACA | GTC | TAC | GCC | AAC | CCT | CCC | CTG | CAC | 1575 |
| Thr | Met | Gln | Thr | Leu 445 | Thr | Cys | Thr | Val | Tyr 450 | Ala | Asn | Pro | Pro | Leu 455 | His | |

| | | | | | | | | | | | | | | | | |
|---|---|---|---|---|---|---|---|---|---|---|---|---|---|---|---|---|
| CAC | ATC | CAG | TGG | TAC | TGG | CAG | CTA | GAA | GAA | GCC | TGC | TCC | TAC | AGA | CCC | 1623 |
| His | Ile | Gln | Trp | Tyr | Trp | Gln | Leu | Glu | Glu | Ala | Cys | Ser | Tyr | Arg | Pro | |
| | | 460 | | | | | 465 | | | | | 470 | | | | |
| GGC | CAA | ACA | AGC | CCG | TAT | GCT | TGT | AAA | GAA | TGG | AGA | CAC | GTG | GAG | GAT | 1671 |
| Gly | Gln | Thr | Ser | Pro | Tyr | Ala | Cys | Lys | Glu | Trp | Arg | His | Val | Glu | Asp | |
| | | 475 | | | | 480 | | | | | | 485 | | | | |
| TTC | CAG | GGG | GGA | AAC | AAG | ATC | GAA | GTC | ACC | AAA | AAC | CAA | TAT | GCC | CTG | 1719 |
| Phe | Gln | Gly | Gly | Asn | Lys | Ile | Glu | Val | Thr | Lys | Asn | Gln | Tyr | Ala | Leu | |
| | | 490 | | | | 495 | | | | | 500 | | | | | |
| ATT | GAA | GGA | AAA | AAC | AAA | ACT | GTA | AGT | ACG | CTG | GTC | ATC | CAA | GCT | GCC | 1767 |
| Ile | Glu | Gly | Lys | Asn | Lys | Thr | Val | Ser | Thr | Leu | Val | Ile | Gln | Ala | Ala | |
| 505 | | | | | 510 | | | | | 515 | | | | | 520 | |
| AAC | GTG | TCA | GCG | TTG | TAC | AAA | TGT | GAA | GCC | ATC | AAC | AAA | GCG | GGA | CGA | 1815 |
| Asn | Val | Ser | Ala | Leu | Tyr | Lys | Cys | Glu | Ala | Ile | Asn | Lys | Ala | Gly | Arg | |
| | | | | 525 | | | | 530 | | | | | 535 | | | |
| GGA | GAG | AGG | GTC | ATC | TCC | TTC | CAT | GTG | ATC | AGG | GGT | CCT | GAA | ATT | ACT | 1863 |
| Gly | Glu | Arg | Val | Ile | Ser | Phe | His | Val | Ile | Arg | Gly | Pro | Glu | Ile | Thr | |
| | | | 540 | | | | | 545 | | | | | 550 | | | |
| GTG | CAA | CCT | GCT | GCC | CAG | CCA | ACT | GAG | CAG | GAG | AGT | GTG | TCC | CTG | TTG | 1911 |
| Val | Gln | Pro | Ala | Ala | Gln | Pro | Thr | Glu | Gln | Glu | Ser | Val | Ser | Leu | Leu | |
| | | 555 | | | | | 560 | | | | | 565 | | | | |
| TGC | ACT | GCA | GAC | AGA | AAT | ACG | TTT | GAG | AAC | CTC | ACG | TGG | TAC | AAG | CTT | 1959 |
| Cys | Thr | Ala | Asp | Arg | Asn | Thr | Phe | Glu | Asn | Leu | Thr | Trp | Tyr | Lys | Leu | |
| | 570 | | | | | 575 | | | | | 580 | | | | | |
| GGC | TCA | CAG | GCA | ACA | TCG | GTC | CAC | ATG | GGC | GAA | TCA | CTC | ACA | CCA | GTT | 2007 |
| Gly | Ser | Gln | Ala | Thr | Ser | Val | His | Met | Gly | Glu | Ser | Leu | Thr | Pro | Val | |
| 585 | | | | | 590 | | | | | 595 | | | | | 600 | |
| TGC | AAG | AAC | TTG | GAT | GCT | CTT | TGG | AAA | CTG | AAT | GGC | ACC | ATG | TTT | TCT | 2055 |
| Cys | Lys | Asn | Leu | Asp | Ala | Leu | Trp | Lys | Leu | Asn | Gly | Thr | Met | Phe | Ser | |
| | | | | 605 | | | | 610 | | | | | 615 | | | |
| AAC | AGC | ACA | AAT | GAC | ATC | TTG | ATT | GTG | GCA | TTT | CAG | AAT | GCC | TCT | CTG | 2103 |
| Asn | Ser | Thr | Asn | Asp | Ile | Leu | Ile | Val | Ala | Phe | Gln | Asn | Ala | Ser | Leu | |
| | | | 620 | | | | | 625 | | | | | 630 | | | |
| CAG | GAC | CAA | GGC | GAC | TAT | GTT | TGC | TCT | GCT | CAA | GAT | AAG | AAG | ACC | AAG | 2151 |
| Gln | Asp | Gln | Gly | Asp | Tyr | Val | Cys | Ser | Ala | Gln | Asp | Lys | Lys | Thr | Lys | |
| | | 635 | | | | | 640 | | | | | 645 | | | | |
| AAA | AGA | CAT | TGC | CTG | GTC | AAA | CAG | CTC | ATC | ATC | CTA | GAG | CGC | ATG | GCA | 2199 |
| Lys | Arg | His | Cys | Leu | Val | Lys | Gln | Leu | Ile | Ile | Leu | Glu | Arg | Met | Ala | |
| | 650 | | | | | 655 | | | | | 660 | | | | | |
| CCC | ATG | ATC | ACC | GGA | AAT | CTG | GAG | AAT | CAG | ACA | ACA | ACC | ATT | GGC | GAG | 2247 |
| Pro | Met | Ile | Thr | Gly | Asn | Leu | Glu | Asn | Gln | Thr | Thr | Thr | Ile | Gly | Glu | |
| 665 | | | | | 670 | | | | | 675 | | | | | 680 | |
| ACC | ATT | GAA | GTG | ACT | TGC | CCA | GCA | TCT | GGA | AAT | CCT | ACC | CCA | CAC | ATT | 2295 |
| Thr | Ile | Glu | Val | Thr | Cys | Pro | Ala | Ser | Gly | Asn | Pro | Thr | Pro | His | Ile | |
| | | | | 685 | | | | | 690 | | | | | 695 | | |
| ACA | TGG | TTC | AAA | GAC | AAC | GAG | ACC | CTG | GTA | GAA | GAT | TCA | GGC | ATT | GTA | 2343 |
| Thr | Trp | Phe | Lys | Asp | Asn | Glu | Thr | Leu | Val | Glu | Asp | Ser | Gly | Ile | Val | |
| | | | 700 | | | | | 705 | | | | | 710 | | | |
| CTG | AGA | GAT | GGG | AAC | CGG | AAC | CTG | ACT | ATC | CGC | AGG | GTG | AGG | AAG | GAG | 2391 |
| Leu | Arg | Asp | Gly | Asn | Arg | Asn | Leu | Thr | Ile | Arg | Arg | Val | Arg | Lys | Glu | |
| | | | 715 | | | | | 720 | | | | | 725 | | | |
| GAT | GGA | GGC | CTC | TAC | ACC | TGC | CAG | GCC | TGC | AAT | GTC | CTT | GGC | TGT | GCA | 2439 |
| Asp | Gly | Gly | Leu | Tyr | Thr | Cys | Gln | Ala | Cys | Asn | Val | Leu | Gly | Cys | Ala | |
| | | 730 | | | | | 735 | | | | | 740 | | | | |
| AGA | GCG | GAG | ACG | CTC | TTC | ATA | ATA | GAA | GGT | GCC | CAG | GAA | AAG | ACC | AAC | 2487 |
| Arg | Ala | Glu | Thr | Leu | Phe | Ile | Ile | Glu | Gly | Ala | Gln | Glu | Lys | Thr | Asn | |
| 745 | | | | | 750 | | | | | 755 | | | | | 760 | |
| TTG | GAA | GTC | ATT | ATC | CTC | GTC | GGC | ACT | GCA | GTG | ATT | GCC | ATG | TTC | TTC | 2535 |
| Leu | Glu | Val | Ile | Ile | Leu | Val | Gly | Thr | Ala | Val | Ile | Ala | Met | Phe | Phe | |
| | | | | 765 | | | | | 770 | | | | | 775 | | |

| | | | | | | | | | | | | | | | | |
|---|---|---|---|---|---|---|---|---|---|---|---|---|---|---|---|---|
| TGG | CTC | CTT | CTT | GTC | ATT | CTC | GTA | CGG | ACC | GTT | AAG | CGG | GCC | AAT | GAA | 2583 |
| Trp | Leu | Leu | Leu 780 | Val | Ile | Leu | Val | Arg 785 | Thr | Val | Lys | Arg | Ala 790 | Asn | Glu | |
| GGG | GAA | CTG | AAG | ACA | GGC | TAC | TTG | TCT | ATT | GTC | ATG | GAT | CCA | GAT | GAA | 2631 |
| Gly | Glu | Leu 795 | Lys | Thr | Gly | Tyr | Leu | Ser 800 | Ile | Val | Met | Asp 805 | Pro | Asp | Glu | |
| TTG | CCC | TTG | GAT | GAG | CGC | TGT | GAA | CGC | TTG | CCT | TAT | GAT | GCC | AGC | AAG | 2679 |
| Leu | Pro 810 | Leu | Asp | Glu | Arg | Cys 815 | Glu | Arg | Leu | Pro | Tyr 820 | Asp | Ala | Ser | Lys | |
| TGG | GAA | TTC | CCC | AGG | GAC | CGG | CTG | AAA | CTA | GGA | AAA | CCT | CTT | GGC | CGC | 2727 |
| Trp 825 | Glu | Phe | Pro | Arg 830 | Asp | Arg | Leu | Lys | Leu 835 | Gly | Lys | Pro | Leu | Gly | Arg 840 | |
| GGT | GCC | TTC | GGC | CAA | GTG | ATT | GAG | GCA | GAC | GCT | TTT | GGA | ATT | GAC | AAG | 2775 |
| Gly | Ala | Phe | Gly | Gln 845 | Val | Ile | Glu | Ala | Asp 850 | Ala | Phe | Gly | Ile | Asp 855 | Lys | |
| ACA | GCG | ACT | TGC | AAA | ACA | GTA | GCC | GTC | AAG | ATG | TTG | AAA | GAA | GGA | GCA | 2823 |
| Thr | Ala | Thr | Cys 860 | Lys | Thr | Val | Ala | Val 865 | Lys | Met | Leu | Lys | Glu 870 | Gly | Ala | |
| ACA | CAC | AGC | GAG | CAT | CGA | GCC | CTC | ATG | TCT | GAA | CTC | AAG | ATC | CTC | ATC | 2871 |
| Thr | His | Ser 875 | Glu | His | Arg | Ala | Leu 880 | Met | Ser | Glu | Leu | Lys 885 | Ile | Leu | Ile | |
| CAC | ATT | GGT | CAC | CAT | CTC | AAT | GTG | GTG | AAC | CTC | CTA | GGC | GCC | TGC | ACC | 2919 |
| His | Ile | Gly | His 890 | His | Leu | Asn | Val | Val 895 | Asn | Leu | Leu | Gly | Ala 900 | Cys | Thr | |
| AAG | CCG | GGA | GGG | CCT | CTC | ATG | GTG | ATT | GTG | GAA | TTC | TCG | AAG | TTT | GGA | 2967 |
| Lys 905 | Pro | Gly | Gly | Pro | Leu 910 | Met | Val | Ile | Val | Glu 915 | Phe | Ser | Lys | Phe | Gly 920 | |
| AAC | CTA | TCA | ACT | TAC | TTA | CGG | GGC | AAG | AGA | AAT | GAA | TTT | GTT | CCC | TAT | 3015 |
| Asn | Leu | Ser | Thr | Tyr 925 | Leu | Arg | Gly | Lys | Arg 930 | Asn | Glu | Phe | Val | Pro 935 | Tyr | |
| AAG | AGC | AAA | GGG | GCA | CGC | TTC | CGC | CAG | GGC | AAG | GAC | TAC | GTT | GGG | GAG | 3063 |
| Lys | Ser | Lys | Gly 940 | Ala | Arg | Phe | Arg | Gln 945 | Gly | Lys | Asp | Tyr | Val 950 | Gly | Glu | |
| CTC | TCC | GTG | GAT | CTG | AAA | AGA | CGC | TTG | GAC | AGC | ATC | ACC | AGC | AGC | CAG | 3111 |
| Leu | Ser | Val 955 | Asp | Leu | Lys | Arg | Arg 960 | Leu | Asp | Ser | Ile | Thr 965 | Ser | Ser | Gln | |
| AGC | TCT | GCC | AGC | TCA | GGC | TTT | GTT | GAG | GAG | AAA | TCG | CTC | AGT | GAT | GTA | 3159 |
| Ser | Ser 970 | Ala | Ser | Ser | Gly | Phe 975 | Val | Glu | Glu | Lys | Ser 980 | Leu | Ser | Asp | Val | |
| GAG | GAA | GAA | GAA | GCT | TCT | GAA | GAA | CTG | TAC | AAG | GAC | TTC | CTG | ACC | TTG | 3207 |
| Glu 985 | Glu | Glu | Glu | Ala | Ser 990 | Glu | Glu | Leu | Tyr | Lys 995 | Asp | Phe | Leu | Thr | Leu 1000 | |
| GAG | CAT | CTC | ATC | TGT | TAC | AGC | TTC | CAA | GTG | GCT | AAG | GGC | ATG | GAG | TTC | 3255 |
| Glu | His | Leu | Ile | Cys 1005 | Tyr | Ser | Phe | Gln | Val 1010 | Ala | Lys | Gly | Met | Glu 1015 | Phe | |
| TTG | GCA | TCA | AGG | AAG | TGT | ATC | CAC | AGG | GAC | CTG | GCA | GCA | CGA | AAC | ATT | 3303 |
| Leu | Ala | Ser | Arg 1020 | Lys | Cys | Ile | His | Arg 1025 | Asp | Leu | Ala | Ala | Arg 1030 | Asn | Ile | |
| CTC | CTA | TCG | GAG | AAG | AAT | GTG | GTT | AAG | ATC | TGT | GAC | TTC | GGC | TTG | GCC | 3351 |
| Leu | Leu | Ser | Glu 1035 | Lys | Asn | Val | Val | Lys 1040 | Ile | Cys | Asp | Phe | Gly 1045 | Leu | Ala | |
| CGG | GAC | ATT | TAT | AAA | GAC | CCG | GAT | TAT | GTC | AGA | AAA | GGA | GAT | GCC | CGA | 3399 |
| Arg | Asp | Ile 1050 | Tyr | Lys | Asp | Pro | Asp 1055 | Tyr | Val | Arg | Lys | Gly 1060 | Asp | Ala | Arg | |
| CTC | CCT | TTG | AAG | TGG | ATG | GCC | CCG | GAA | ACC | ATT | TTT | GAC | AGA | GTA | TAC | 3447 |
| Leu | Pro 1065 | Leu | Lys | Trp | Met | Ala 1070 | Pro | Glu | Thr | Ile | Phe 1075 | Asp | Arg | Val | Tyr 1080 | |
| ACA | ATT | CAG | AGC | GAT | GTG | TGG | TCT | TTC | GGT | GTG | TTG | CTC | TGG | GAA | ATA | 3495 |
| Thr | Ile | Gln | Ser | Asp 1085 | Val | Trp | Ser | Phe | Gly 1090 | Val | Leu | Leu | Trp | Glu 1095 | Ile | |

| | | | | | | | | | | | | | | | | |
|---|---|---|---|---|---|---|---|---|---|---|---|---|---|---|---|---|
| TTT | TCC | TTA | GGT | GCC | TCC | CCA | TAC | CCT | GGG | GTC | AAG | ATT | GAT | GAA | GAA | 3543 |
| Phe | Ser | Leu | Gly 1100 | Ala | Ser | Pro | Tyr | Pro 1105 | Gly | Val | Lys | Ile | Asp 1110 | Glu | Glu | |
| TTT | TGT | AGG | AGA | TTG | AAA | GAA | GGA | ACT | AGA | ATG | CGG | GCT | CCT | GAC | TAC | 3591 |
| Phe | Cys | Arg 1115 | Arg | Leu | Lys | Glu | Gly | Thr 1120 | Arg | Met | Arg | Ala | Pro 1125 | Asp | Tyr | |
| ACT | ACC | CCA | GAA | ATG | TAC | CAG | ACC | ATG | CTG | GAC | TGC | TGG | CAT | GAG | GAC | 3639 |
| Thr | Thr | Pro 1130 | Glu | Met | Tyr | Gln | Thr | Met 1135 | Leu | Asp | Cys | Trp | His 1140 | Glu | Asp | |
| CCC | AAC | CAG | AGA | CCC | TCG | TTT | TCA | GAG | TTG | GTG | GAG | CAT | TTG | GGA | AAC | 3687 |
| Pro | Asn | Gln | Arg | Pro 1145 | Ser | Phe | Ser 1150 | Glu | Leu | Val | Glu 1155 | His | Leu | Gly | Asn 1160 | |
| CTC | CTG | CAA | GCA | AAT | GCG | CAG | CAG | GAT | GGC | AAA | GAC | TAT | ATT | GTT | CTT | 3735 |
| Leu | Leu | Gln | Ala | Asn 1165 | Ala | Gln | Gln | Asp | Gly 1170 | Lys | Asp | Tyr | Ile | Val 1175 | Leu | |
| CCA | ATG | TCA | GAG | ACA | CTG | AGC | ATG | GAA | GAG | GAT | TCT | GGA | CTC | TCC | CTG | 3783 |
| Pro | Met | Ser | Glu | Thr 1180 | Leu | Ser | Met | Glu | Glu 1185 | Asp | Ser | Gly | Leu | Ser 1190 | Leu | |
| CCT | ACC | TCA | CCT | GTT | TCC | TGT | ATG | GAG | GAA | GAG | GAA | GTG | TGC | GAC | CCC | 3831 |
| Pro | Thr | Ser | Pro 1195 | Val | Ser | Cys | Met | Glu 1200 | Glu | Glu | Glu | Val | Cys 1205 | Asp | Pro | |
| AAA | TTC | CAT | TAT | GAC | AAC | ACA | GCA | GGA | ATC | AGT | CAT | TAT | CTC | CAG | AAC | 3879 |
| Lys | Phe 1210 | His | Tyr | Asp | Asn | Thr 1215 | Ala | Gly | Ile | Ser | His 1220 | Tyr | Leu | Gln | Asn | |
| AGT | AAG | CGA | AAG | AGC | CGG | CCA | GTG | AGT | GTA | AAA | ACA | TTT | GAA | GAT | ATC | 3927 |
| Ser 1225 | Lys | Arg | Lys | Ser | Arg 1230 | Pro | Val | Ser | Val | Lys 1235 | Thr | Phe | Glu | Asp | Ile 1240 | |
| CCA | TTG | GAG | GAA | CCA | GAA | GTA | AAA | GTG | ATC | CCA | GAT | GAC | AGC | CAG | ACA | 3975 |
| Pro | Leu | Glu | Glu | Pro 1245 | Glu | Val | Lys | Val | Ile 1250 | Pro | Asp | Asp | Ser | Gln 1255 | Thr | |
| GAC | AGT | GGG | ATG | GTC | CTT | GCA | TCA | GAA | GAG | CTG | AAA | ACT | CTG | GAA | GAC | 4023 |
| Asp | Ser | Gly | Met 1260 | Val | Leu | Ala | Ser | Glu 1265 | Glu | Leu | Lys | Thr | Leu 1270 | Glu | Asp | |
| AGG | AAC | AAA | TTA | TCT | CCA | TCT | TTT | GGT | GGA | ATG | ATG | CCC | AGT | AAA | AGC | 4071 |
| Arg | Asn | Lys | Leu | Ser 1275 | Pro | Ser | Phe | Gly | Gly 1280 | Met | Met | Pro | Ser | Lys 1285 | Ser | |
| AGG | GAG | TCT | GTG | GCC | TCG | GAA | GGC | TCC | AAC | CAG | ACC | AGT | GGC | TAC | CAG | 4119 |
| Arg | Glu | Ser 1290 | Val | Ala | Ser | Glu | Gly 1295 | Ser | Asn | Gln | Thr | Ser 1300 | Gly | Tyr | Gln | |
| TCT | GGG | TAT | CAC | TCA | GAT | GAC | ACA | GAC | ACC | ACC | GTG | TAC | TCC | AGC | GAC | 4167 |
| Ser | Gly 1305 | Tyr | His | Ser | Asp | Asp 1310 | Thr | Asp | Thr | Thr | Val 1315 | Tyr | Ser | Ser | Asp 1320 | |
| GAG | GCA | GGA | CTT | TTA | AAG | ATG | GTG | GAT | GCT | GCA | GTT | CAC | GCT | GAC | TCA | 4215 |
| Glu | Ala | Gly | Leu | Leu 1325 | Lys | Met | Val | Asp | Ala 1330 | Ala | Val | His | Ala | Asp 1335 | Ser | |
| GGG | ACC | ACA | CTG | CAG | CTC | ACC | TCC | TGT | TTA | AAT | GGA | AGT | GGT | CCT | GTC | 4263 |
| Gly | Thr | Thr | Leu 1340 | Gln | Leu | Thr | Ser | Cys 1345 | Leu | Asn | Gly | Ser | Gly 1350 | Pro | Val | |
| CCG | GCT | CCG | CCC | CCA | ACT | CCT | GGA | AAT | CAC | GAG | AGA | GGT | GCT | GCT | TAGATTTT | 4318 |
| Pro | Ala | Pro | Pro | Pro 1355 | Thr | Pro | Gly | Asn | His 1360 | Glu | Arg | Gly | Ala | Ala 1365 | | |

| | | | | | |
|---|---|---|---|---|---|
| AGTGTTGTTC | TTTCCACCAC | CCGGAAGTAG | CCACATTTGA | TTTTCATTTT | TGGAGGAGGG | 4378 |
| ACCTCAGACT | GCAAGGAGCT | TGTCCTCAGG | GCATTTCCAG | AGAAGATGCC | CATGACCCAA | 4438 |
| GAATGTGTTG | ACTCTACTCT | CTTTTCCATT | CATTTAAAAG | TCCTATATAA | TGTGCCCTGC | 4498 |
| TGTGGTCTCA | CTACCAGTTA | AAGCAAAAGA | CTTTCAAACA | CGTGGACTCT | GTCCTCCAAG | 4558 |
| AAGTGGCAAC | GGCACCTCTG | TGAAACTGGA | TCGAATGGGC | AATGCTTTGT | GTGTTGAGGA | 4618 |
| TGGGTGAGAT | GTCCCAGGGC | CGAGTCTGTC | TACCTTGGAG | GCTTTGTGGA | GGATGCGGCT | 4678 |

-continued

```
ATGAGCCAAG TGTTAAGTGT GGGATGTGGA CTGGGAGGAA GGAAGGCGCA AGCCGTCCGG    4738
AGAGCGGTTG GAGCCTGCAG ATGCATTGTG CTGGCTCTGG TGGAGGTGGG CTTGTGGCCT    4798
GTCAGGAAAC GCAAAGGCGG CCGGCAGGGT TTGGTTTTGG AAGGTTTGCG TGCTCTTCAC    4858
AGTCGGGTTA CAGGCGAGTT CCCTGTGGCG TTTCCTACTC CTAATGAGAG TTCCTTCCGG    4918
ACTCTTACGT GTCTCCTGGC CTGGCCCAG  GAAGGAAATG ATGCAGCTTG CTCCTTCCTC    4978
ATCTCTCAGG CTGTGCCTTA ATTCAGAACA CCAAAAGAGA GGAACGTCGG CAGAGGCTCC    5038
TGACGGGGCC GAAGAATTGT GAGAACAGAA CAGAAACTCA GGGTTTCTGC TGGGTGGAGA    5098
CCCACGTGGC GCCCTGGTGG CAGGTCTGAG GGTTCTCTGT CAAGTGGCGG TAAAGGCTCA    5158
GGCTGGTGTT CTTCCTCTAT CTCCACTCCT GTCAGGCCCC CAAGTCCTCA GTATTTTAGC    5218
TTTGTGGCTT CCTGATGGCA GAAAAATCTT AATTGGTTGG TTTGCTCTCC AGATAATCAC    5278
TAGCCAGATT TCGAAATTAC TTTTTAGCCG AGGTTATGAT AACATCTACT GTATCCTTTA    5338
GAATTTTAAC CTATAAAACT ATGTCTACTG GTTTCTGCCT GTGTGCTTAT GTTAAAAAAA    5398
AAAAAAA                                                              5406
```

( 2 ) INFORMATION FOR SEQ ID NO:6:

( i ) SEQUENCE CHARACTERISTICS:
         ( A ) LENGTH: 1367 amino acids
         ( B ) TYPE: amino acid
         ( D ) TOPOLOGY: linear ( i i ) MOLECULE TYPE: protein ( x i ) SEQUENCE DESCRIPTION: SEQ ID NO:6:

```
Met Glu Ser Lys Gly Leu Leu Ala Val Ala Leu Trp Phe Cys Val Glu
 1               5                  10                  15

Thr Arg Ala Ala Ser Val Gly Leu Pro Gly Asp Phe Leu His Pro Pro
            20                  25                  30

Lys Leu Ser Thr Gln Lys Asp Ile Leu Thr Ile Leu Ala Asn Thr Thr
        35                  40                  45

Leu Gln Ile Thr Cys Arg Gly Gln Arg Asp Leu Asp Trp Leu Trp Pro
    50                  55                  60

Asn Ala Gln Arg Asp Ser Glu Glu Arg Val Leu Val Thr Glu Cys Gly
65                  70                  75                  80

Gly Gly Asp Ser Ile Phe Cys Lys Thr Leu Thr Ile Pro Arg Val Val
                85                  90                  95

Gly Asn Asp Thr Gly Ala Tyr Lys Cys Ser Tyr Arg Asp Val Asp Ile
            100                 105                 110

Ala Ser Thr Val Tyr Val Tyr Val Arg Asp Tyr Arg Ser Pro Phe Ile
        115                 120                 125

Ala Ser Val Ser Asp Gln His Gly Ile Val Tyr Ile Thr Glu Asn Lys
    130                 135                 140

Asn Lys Thr Val Val Ile Pro Cys Arg Gly Ser Ile Ser Asn Leu Asn
145                 150                 155                 160

Val Ser Leu Cys Ala Arg Tyr Pro Glu Lys Arg Phe Val Pro Asp Gly
                165                 170                 175

Asn Arg Ile Ser Trp Asp Ser Glu Ile Gly Phe Thr Leu Pro Ser Tyr
            180                 185                 190

Met Ile Ser Tyr Ala Gly Met Val Phe Cys Glu Ala Lys Ile Asn Asp
        195                 200                 205

Glu Thr Tyr Gln Ser Ile Met Tyr Ile Val Val Val Gly Tyr Arg
    210                 215                 220
```

```
Ile Tyr Asp Val Ile Leu Ser Pro Pro His Glu Ile Glu Leu Ser Ala
225                 230                 235                 240

Gly Glu Lys Leu Val Leu Asn Cys Thr Ala Arg Thr Glu Leu Asn Val
                245                 250                 255

Gly Leu Asp Phe Thr Trp His Ser Pro Pro Ser Lys Ser His His Lys
            260                 265                 270

Lys Ile Val Asn Arg Asp Val Lys Pro Phe Pro Gly Thr Val Ala Lys
        275                 280                 285

Met Phe Leu Ser Thr Leu Thr Ile Glu Ser Val Thr Lys Ser Asp Gln
    290                 295                 300

Gly Glu Tyr Thr Cys Val Ala Ser Ser Gly Arg Met Ile Lys Arg Asn
305                 310                 315                 320

Arg Thr Phe Val Arg Val His Thr Lys Pro Phe Ile Ala Phe Gly Ser
            325                 330                 335

Gly Met Lys Ser Leu Val Glu Ala Thr Val Gly Ser Gln Val Arg Ile
        340                 345                 350

Pro Val Lys Tyr Leu Ser Tyr Pro Ala Pro Asp Ile Lys Trp Tyr Arg
        355                 360                 365

Asn Gly Arg Pro Ile Glu Ser Asn Tyr Thr Met Ile Val Gly Asp Glu
    370                 375                 380

Leu Thr Ile Met Glu Val Thr Glu Arg Asp Ala Gly Asn Tyr Thr Val
385                 390                 395                 400

Ile Leu Thr Asn Pro Ile Ser Met Glu Lys Gln Ser His Met Val Ser
            405                 410                 415

Leu Val Val Asn Val Pro Pro Gln Ile Gly Glu Lys Ala Leu Ile Ser
            420                 425                 430

Pro Met Asp Ser Tyr Gln Tyr Gly Thr Met Gln Thr Leu Thr Cys Thr
        435                 440                 445

Val Tyr Ala Asn Pro Pro Leu His His Ile Gln Trp Tyr Trp Gln Leu
    450                 455                 460

Glu Glu Ala Cys Ser Tyr Arg Pro Gly Gln Thr Ser Pro Tyr Ala Cys
465                 470                 475                 480

Lys Glu Trp Arg His Val Glu Asp Phe Gln Gly Gly Asn Lys Ile Glu
            485                 490                 495

Val Thr Lys Asn Gln Tyr Ala Leu Ile Glu Gly Lys Asn Lys Thr Val
        500                 505                 510

Ser Thr Leu Val Ile Gln Ala Ala Asn Val Ser Ala Leu Tyr Lys Cys
        515                 520                 525

Glu Ala Ile Asn Lys Ala Gly Arg Gly Glu Arg Val Ile Ser Phe His
530                 535                 540

Val Ile Arg Gly Pro Glu Ile Thr Val Gln Pro Ala Ala Gln Pro Thr
545                 550                 555                 560

Glu Gln Glu Ser Val Ser Leu Leu Cys Thr Ala Asp Arg Asn Thr Phe
                565                 570                 575

Glu Asn Leu Thr Trp Tyr Lys Leu Gly Ser Gln Ala Thr Ser Val His
            580                 585                 590

Met Gly Glu Ser Leu Thr Pro Val Cys Lys Asn Leu Asp Ala Leu Trp
        595                 600                 605

Lys Leu Asn Gly Thr Met Phe Ser Asn Ser Thr Asn Asp Ile Leu Ile
610                 615                 620

Val Ala Phe Gln Asn Ala Ser Leu Gln Asp Gln Gly Asp Tyr Val Cys
625                 630                 635                 640

Ser Ala Gln Asp Lys Lys Thr Lys Lys Arg His Cys Leu Val Lys Gln
            645                 650                 655
```

```
Leu Ile Ile Leu Glu Arg Met Ala Pro Met Ile Thr Gly Asn Leu Glu
            660                 665                 670

Asn Gln Thr Thr Thr Ile Gly Glu Thr Ile Glu Val Thr Cys Pro Ala
        675                 680                 685

Ser Gly Asn Pro Thr Pro His Ile Thr Trp Phe Lys Asp Asn Glu Thr
    690                 695                 700

Leu Val Glu Asp Ser Gly Ile Val Leu Arg Asp Gly Asn Arg Asn Leu
705                 710                 715                 720

Thr Ile Arg Arg Val Arg Lys Glu Asp Gly Gly Leu Tyr Thr Cys Gln
                725                 730                 735

Ala Cys Asn Val Leu Gly Cys Ala Arg Ala Glu Thr Leu Phe Ile Ile
            740                 745                 750

Glu Gly Ala Gln Glu Lys Thr Asn Leu Glu Val Ile Ile Leu Val Gly
        755                 760                 765

Thr Ala Val Ile Ala Met Phe Phe Trp Leu Leu Leu Val Ile Leu Val
    770                 775                 780

Arg Thr Val Lys Arg Ala Asn Glu Gly Glu Leu Lys Thr Gly Tyr Leu
785                 790                 795                 800

Ser Ile Val Met Asp Pro Asp Glu Leu Pro Leu Asp Glu Arg Cys Glu
                805                 810                 815

Arg Leu Pro Tyr Asp Ala Ser Lys Trp Glu Phe Pro Arg Asp Arg Leu
            820                 825                 830

Lys Leu Gly Lys Pro Leu Gly Arg Gly Ala Phe Gly Gln Val Ile Glu
        835                 840                 845

Ala Asp Ala Phe Gly Ile Asp Lys Thr Ala Thr Cys Lys Thr Val Ala
    850                 855                 860

Val Lys Met Leu Lys Glu Gly Ala Thr His Ser Glu His Arg Ala Leu
865                 870                 875                 880

Met Ser Glu Leu Lys Ile Leu Ile His Ile Gly His His Leu Asn Val
                885                 890                 895

Val Asn Leu Leu Gly Ala Cys Thr Lys Pro Gly Gly Pro Leu Met Val
            900                 905                 910

Ile Val Glu Phe Ser Lys Phe Gly Asn Leu Ser Thr Tyr Leu Arg Gly
        915                 920                 925

Lys Arg Asn Glu Phe Val Pro Tyr Lys Ser Lys Gly Ala Arg Phe Arg
    930                 935                 940

Gln Gly Lys Asp Tyr Val Gly Glu Leu Ser Val Asp Leu Lys Arg Arg
945                 950                 955                 960

Leu Asp Ser Ile Thr Ser Ser Gln Ser Ser Ala Ser Ser Gly Phe Val
                965                 970                 975

Glu Glu Lys Ser Leu Ser Asp Val Glu Glu Glu Ala Ser Glu Glu
            980                 985                 990

Leu Tyr Lys Asp Phe Leu Thr Leu Glu His Leu Ile Cys Tyr Ser Phe
        995                 1000                1005

Gln Val Ala Lys Gly Met Glu Phe Leu Ala Ser Arg Lys Cys Ile His
    1010                1015                1020

Arg Asp Leu Ala Ala Arg Asn Ile Leu Leu Ser Glu Lys Asn Val Val
1025                1030                1035                1040

Lys Ile Cys Asp Phe Gly Leu Ala Arg Asp Ile Tyr Lys Asp Pro Asp
                1045                1050                1055

Tyr Val Arg Lys Gly Asp Ala Arg Leu Pro Leu Lys Trp Met Ala Pro
            1060                1065                1070

Glu Thr Ile Phe Asp Arg Val Tyr Thr Ile Gln Ser Asp Val Trp Ser
```

|      | 1075 |      |      |      | 1080 |      |      |      |      | 1085 |      |      |      |
|------|------|------|------|------|------|------|------|------|------|------|------|------|------|
| Phe  | Gly  | Val  | Leu  | Leu  | Trp  | Glu  | Ile  | Phe  | Ser  | Leu  | Gly  | Ala  | Ser  | Pro  | Tyr  |
|      | 1090 |      |      |      |      | 1095 |      |      |      |      | 1100 |      |      |

| Pro  | Gly  | Val  | Lys  | Ile  | Asp  | Glu  | Glu  | Phe  | Cys  | Arg  | Arg  | Leu  | Lys  | Glu  | Gly  |
| 1105 |      |      |      |      | 1110 |      |      |      |      | 1115 |      |      |      |      | 1120 |

| Thr  | Arg  | Met  | Arg  | Ala  | Pro  | Asp  | Tyr  | Thr  | Thr  | Pro  | Glu  | Met  | Tyr  | Gln  | Thr  |
|      |      |      |      |      | 1125 |      |      |      | 1130 |      |      |      |      | 1135 |      |

| Met  | Leu  | Asp  | Cys  | Trp  | His  | Glu  | Asp  | Pro  | Asn  | Gln  | Arg  | Pro  | Ser  | Phe  | Ser  |
|      |      |      |      | 1140 |      |      |      |      | 1145 |      |      |      | 1150 |      |      |

| Glu  | Leu  | Val  | Glu  | His  | Leu  | Gly  | Asn  | Leu  | Leu  | Gln  | Ala  | Asn  | Ala  | Gln  | Gln  |
|      |      |      | 1155 |      |      |      |      | 1160 |      |      |      |      | 1165 |      |      |

| Asp  | Gly  | Lys  | Asp  | Tyr  | Ile  | Val  | Leu  | Pro  | Met  | Ser  | Glu  | Thr  | Leu  | Ser  | Met  |
|      | 1170 |      |      |      |      | 1175 |      |      |      |      | 1180 |      |      |      |      |

| Glu  | Glu  | Asp  | Ser  | Gly  | Leu  | Ser  | Leu  | Pro  | Thr  | Ser  | Pro  | Val  | Ser  | Cys  | Met  |
| 1185 |      |      |      |      | 1190 |      |      |      |      | 1195 |      |      |      |      | 1200 |

| Glu  | Glu  | Glu  | Glu  | Val  | Cys  | Asp  | Pro  | Lys  | Phe  | His  | Tyr  | Asp  | Asn  | Thr  | Ala  |
|      |      |      |      | 1205 |      |      |      |      | 1210 |      |      |      |      | 1215 |      |

| Gly  | Ile  | Ser  | His  | Tyr  | Leu  | Gln  | Asn  | Ser  | Lys  | Arg  | Lys  | Ser  | Arg  | Pro  | Val  |
|      |      |      | 1220 |      |      |      |      | 1225 |      |      |      |      | 1230 |      |      |

| Ser  | Val  | Lys  | Thr  | Phe  | Glu  | Asp  | Ile  | Pro  | Leu  | Glu  | Glu  | Pro  | Glu  | Val  | Lys  |
|      |      | 1235 |      |      |      |      | 1240 |      |      |      |      | 1245 |      |      |      |

| Val  | Ile  | Pro  | Asp  | Asp  | Ser  | Gln  | Thr  | Asp  | Ser  | Gly  | Met  | Val  | Leu  | Ala  | Ser  |
|      | 1250 |      |      |      |      | 1255 |      |      |      |      | 1260 |      |      |      |      |

| Glu  | Glu  | Leu  | Lys  | Thr  | Leu  | Glu  | Asp  | Arg  | Asn  | Lys  | Leu  | Ser  | Pro  | Ser  | Phe  |
| 1265 |      |      |      |      | 1270 |      |      |      |      | 1275 |      |      |      |      | 1280 |

| Gly  | Gly  | Met  | Met  | Pro  | Ser  | Lys  | Ser  | Arg  | Glu  | Ser  | Val  | Ala  | Ser  | Glu  | Gly  |
|      |      |      |      | 1285 |      |      |      |      | 1290 |      |      |      |      | 1295 |      |

| Ser  | Asn  | Gln  | Thr  | Ser  | Gly  | Tyr  | Gln  | Ser  | Gly  | Tyr  | His  | Ser  | Asp  | Asp  | Thr  |
|      |      |      | 1300 |      |      |      |      | 1305 |      |      |      |      | 1310 |      |      |

| Asp  | Thr  | Thr  | Val  | Tyr  | Ser  | Ser  | Asp  | Glu  | Ala  | Gly  | Leu  | Leu  | Lys  | Met  | Val  |
|      |      |      | 1315 |      |      |      | 1320 |      |      |      |      | 1325 |      |      |      |

| Asp  | Ala  | Ala  | Val  | His  | Ala  | Asp  | Ser  | Gly  | Thr  | Thr  | Leu  | Gln  | Leu  | Thr  | Ser  |
|      | 1330 |      |      |      |      | 1335 |      |      |      |      | 1340 |      |      |      |      |

| Cys  | Leu  | Asn  | Gly  | Ser  | Gly  | Pro  | Val  | Pro  | Ala  | Pro  | Pro  | Pro  | Thr  | Pro  | Gly  |
| 1345 |      |      |      |      | 1350 |      |      |      |      | 1355 |      |      |      |      | 1360 |

| Asn  | His  | Glu  | Arg  | Gly  | Ala  | Ala  |
|      |      |      |      | 1365 |      |      |

NUCLEIC ACIDS ENCODING SOLUBLE HUMAN FLK-2 EXTRACELLULAR DOMAIN

The invention described in this application was made with U.S. government support from Grant Numbers R01-CA45339 and R01-DK42989 awarded by the National Institutes of Health. The government has certain rights in this invention.

This application is a continuation-in-part of Ser. No. 813,593 filed Dec. 24, 1991, now U.S. Pat. No. 5,185,438, which is a continuation-in-part of Ser. No. 793,065 filed Nov. 15, 1991, abandoned, which is a continuation-in-part of Ser. No. 728,913 filed Jun. 28, 1991, abandoned, which is a continuation-in-part of Ser. No. 679,666 filed Apr. 2, 1991, abandoned, all of which are incorporated herein by reference.

FIELD OF THE INVENTION

The present invention relates to hematopoietic stem cell receptors, ligands for such receptors, and nucleic acid molecules encoding such receptors and ligands.

BACKGROUND OF THE INVENTION

The mammalian hematopoietic system comprises red and white blood cells. These cells are the mature cells that result from more primitive lineage-restricted cells. The cells of the hematopoietic system have been reviewed by Dexter and Spooncer in the Annual Review of Cell Biology 3, 423–441 (1987).

The red blood cells, or erythrocytes, result from primitive cells referred to by Dexter and Spooncer as erythroid burst-forming units (BFU-E). The immediate progeny of the erythroid burst-forming units are called erythroid colony-forming units (CFU-E).

The white blood cells contain the mature cells of the lymphoid and myeloid systems. The lymphoid cells include B lymphocytes and T lymphocytes. The B and T lymphocytes result from earlier progenitor cells referred to by Dexter and Spooncer as preT and preB cells.

The myeloid system comprises a number of cells including granulocytes, platelets, monocytes, macrophages, and megakaryocytes. The granulocytes are further divided into neutrophils, eosinophils, basophils and mast cells.

Each of the mature hematopoietic cells are specialized for specific functions. For example, erythrocytes are responsible for oxygen and carbon dioxide transport. T and B lymphocytes are responsible for cell- and antibody-mediated immune responses, respectively. Platelets are involved in blood clotting. Granulocytes and macrophages act generally as scavengers and accessory cells in the immune response against invading organisms and their by-products.

At the center of the hematopoietic system lie one or more totipotent hematopoietic stem cells, which undergo a series of differentiation steps leading to increasingly lineage-restricted progenitor cells. The more mature progenitor cells are restricted to producing one or two lineages. Some examples of lineage-restricted progenitor cells mentioned by Dexter and Spooncer include granulocyte/macrophage colony-forming cells (GM-CFC), megakaryocyte colony-forming cells (Meg-CFC), eosinophil colony-forming cells (Eos-CFC), and basophil colony-forming cells (Bas-CFC). Other examples of progenitor cells are discussed above.

The hematopoietic system functions by means of a precisely controlled production of the various mature lineages. The totipotent stem cell possesses the ability both to self renew and to differentiate into committed progenitors for all hematopoietic lineages. These most primitive of hematopoietic cells are both necessary and sufficient for the complete and permanent hematopoietic reconstitution of a radiation-ablated hematopoietic system in mammals. The ability of stem cells to reconstitute the entire hematopoietic system is the basis of bone marrow transplant therapy.

It is known that growth factors play an important role in the development and operation of the mammalian hematopoietic system. The role of growth factors is complex, however, and not well understood at the present time. One reason for the uncertainty is that much of what is known about hematopoietic growth factors results from in vitro experiments. Such experiments do not necessarily reflect in vivo realities.

In addition, in vitro hematopoiesis can be established in the absence of added growth factors, provided that marrow stromal cells are added to the medium. The relationship between stromal cells and hematopoietic growth factors in vivo is not understood. Nevertheless, hematopoietic growth factors have been shown to be highly active in vivo.

From what is known about them, hematopoietic growth factors appear to exhibit a spectrum of activities. At one end of the spectrum are growth factors such as erythropoietin, which is believed to promote proliferation only of mature erythroid progenitor cells. In the middle of the spectrum are growth factors such as IL-3, which is believed to facilitate the growth and development of early stem cells as well as of numerous progenitor cells. Some examples of progenitor cells induced by IL-3 include those restricted to the granulocyte/macrophage, eosinophil, megakaryocyte, erythroid and mast cell lineages.

At the other end of the spectrum is the hematopoietic growth factor that, along with the corresponding receptor, was discussed in a series of articles in the Oct. 5, 1990 edition of *Cell*. The receptor is the product of the W locus, c-kit, which is a member of the class of receptor protein tyrosine kinases. The ligand for c-kit, which is referred to by various names such as stem cell factor (SCF) and mast cell growth factor (MGF), is believed to be essential for the development of early hematopoietic stem cells and cells restricted to the erythroid and mast cell lineages in mice; see, for example, Copeland et al., Cell 63, 175–183 (1990).

It appears, therefore, that there are growth factors that exclusively affect mature cells. There also appear to be growth factors that affect both mature cells and stem cells. The growth factors that affect both types of cells may affect a small number or a large number of mature cells.

There further appears to be an inverse relationship between the ability of a growth factor to affect mature cells and the ability of the growth factor to affect stem cells. For example, the c-kit ligand, which stimulates a small number of mature cells, is believed to be more important in the renewal and development of stem cells then is IL-3, which is reported to stimulate proliferation of many mature cells (see above).

Prior to the present specification, there have been no reports of growth factors that exclusively stimulate stem cells in the absence of an effect on mature cells. The discovery of such growth factors would be of particular significance.

As mentioned above, c-kit is a protein tyrosine kinase (pTK). It is becoming increasingly apparent that the protein tyrosine kinases play an important role as cellular receptors for hematopoietic growth factors. Other receptor pTKs include the receptors of colony stimulating factor 1 (CSF-1) and PDGF.

The pTK family can be recognized by the presence of several conserved amino acid regions in the catalytic domain. These conserved regions are summarized by Hanks et al. in Science 241, 42–52 (1988), see FIG. 1 starting on page 46 and by Wilks in Proc. Natl. Acad. Sci. U.S.A. 86, 1603–1607 (1989), see FIG. 2 on page 1605.

Additional protein tyrosine kinases that represent hematopoietic growth factor receptors are needed in order more effectively to stimulate the self-renewal of the totipotent hematopoietic stem cell and to stimulate the development of all cells of the hematopoietic system both in vitro and in vivo. Novel hematopoietic growth factor receptors that are present only on primitive stem cells, but are not present on mature progenitor cells, are particularly desired. Ligands for the novel receptors are also desirable to act as hematopoietic growth factors. Nucleic acid sequences encoding the receptors and ligands are needed to produce recombinant receptors and ligands.

SUMMARY OF THE INVENTION

These and other objectives as will be apparent to those with ordinary skill in the art have been met by providing isolated mammalian nucleic acid molecules encoding receptor protein tyrosine kinases expressed in primitive hematopoietic cells and not expressed in mature hematopoietic cells. Also included are the receptors encoded by such nucleic acid molecules; the nucleic acid molecules encoding receptor protein tyrosine kinases having the sequences shown in FIG. 1A (murine flk-2), FIG. 1B (human flk-2) and FIG. 2 (murine flk-1) (see SEQ ID. NOS. 1, 3, and 5, respectively); the receptor protein tyrosine kinases having the amino acid sequences shown in FIG. 1A, FIG. 1B, and FIG. 2 (see SEQ ID. NOS. 2, 4 and 6, respectively); ligands for the receptors; nucleic acid sequences that encode the ligands; and methods of stimulating the proliferation of primitive mammalian hematopoietic stem cells comprising contacting the stem cells with a ligand that binds to a receptor protein tyrosine kinase expressed in primitive mammalian hematopoietic cells and not expressed in mature hematopoietic cells.

DESCRIPTION OF THE FIGURES

FIGS. 1A-1 through FIG. 1A-6 shows the cDNA and amino acid sequences of murine flk-2. All references herein to FIG. 1A are intended to refer to FIGS. 1A-1 through 1A-6. The amino acid residues occur directly below the nucleotides in the open reading frame. Amino acids 1–27 constitute the hydrophobic leader sequence. Amino acids 28–544 constitute the extracellular receptor domain. Amino acids 545–564 constitute the transmembrane region. The remainder of the amino acids constitute the intracellular catalytic domain. The following amino acid residues in the intracellular domain are catalytic sub-domains identified by Hanks (see above): 618–623, 811–819, 832–834, 857–862, 872–878. The sequence at residues 709–785 is a signature sequence characteristic of flk-2. The protein tyrosine kinases generally have a signature sequence in this region. (See SEQ. ID. NOS. 1–2)

FIGS. 1B-1 through 1B-6 shows the complete cDNA and amino acid sequences of human flk-2 receptor. (See SEQ. ID. NOS. 3–4) All references herein to FIG. 1B are intended to refer to FIGS. 1B-1 through 1B-6.

FIGS. 2-1 through 2-8 shows the cDNA and amino acid sequences of murine flk-1. All references herein to FIG. 2 are intended to refer to FIGS. 2-1 through 2-6. Amino acid residues 763–784 constitute the transmembrane region of flk-1. (See SEQ. ID. NOS. 5–6)

FIG. 3 shows the time response of binding between a murine stromal cell line (2018) and APtag-flk-2 as well as APtag-flk-1. APtag without receptor (SEAP) is used as a control. See Example 8.

FIG. 4 shows the dose response of binding between stromal cells (2018) and APtag-flk-2 as well as APtag-flk-1. APtag without receptor (SEAP) is used as a control. See Example 8.

DETAILED DESCRIPTION OF THE INVENTION

Receptors

Figure 3:
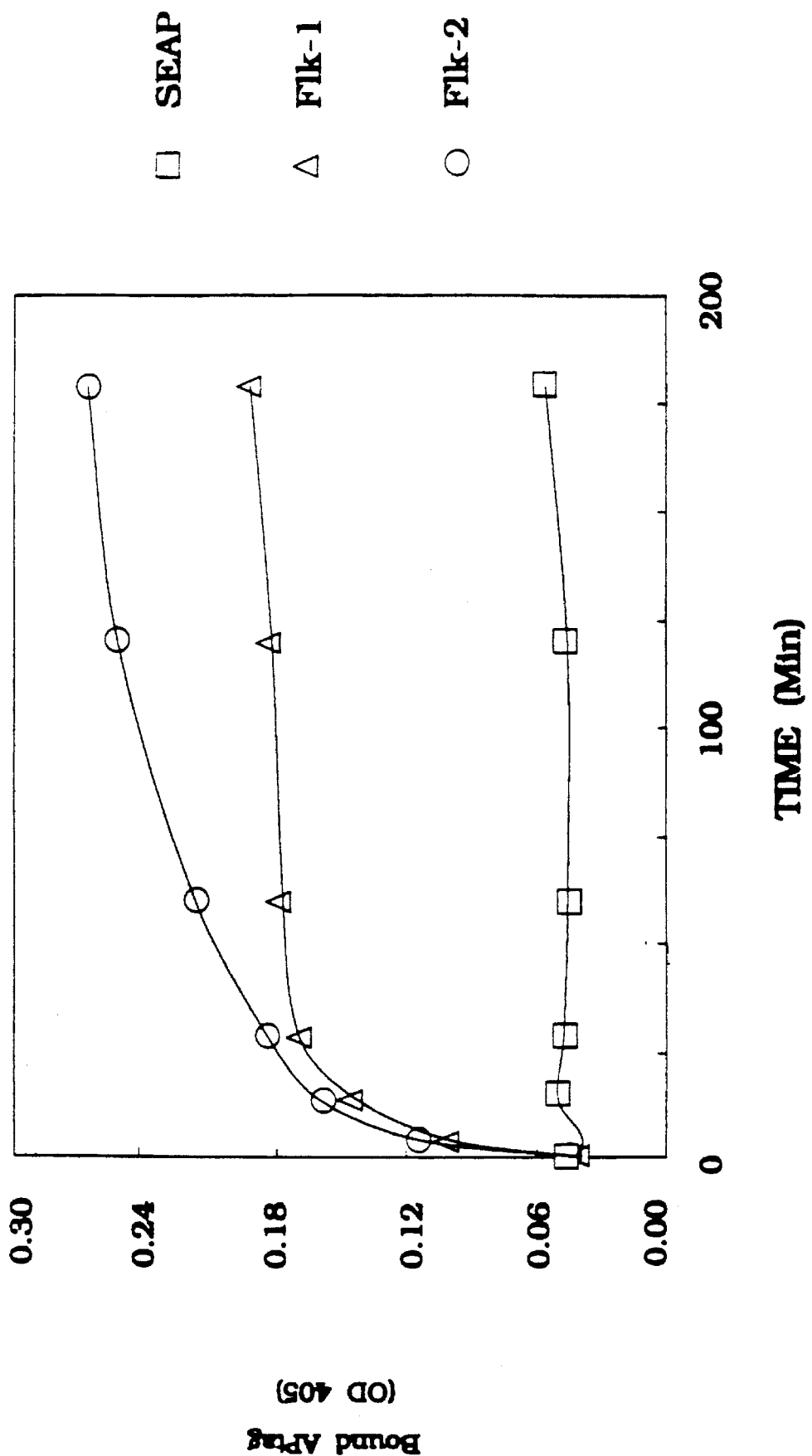

In one embodiment, the invention relates to an isolated mammalian nucleic acid molecule encoding a receptor protein tyrosine kinase expressed in primitive mammalian hematopoietic cells and not expressed in mature hematopoietic cells.

The nucleic acid molecule may be a DNA, cDNA, or RNA molecule. The mammal in which the nucleic acid molecule exists may be any mammal, such as a mouse, rat, rabbit, or human.

The nucleic acid molecule encodes a protein tyrosine kinase (pTK). Members of the pTK family can be recognized by the conserved amino acid regions in the catalytic domains. Examples of pTK consensus sequences have been provided by Hanks et al. in Science 241, 42–52 (1988); see especially FIG. 1 starting on page 46 and by Wilks in Proc. Natl. Acad. Sci. U.S.A. 86, 1603–1607 (1989); see especially FIG. 2 on page 1605. A methionine residue at position 205 in the conserved sequence WMAPES is characteristic of pTK's that are receptors.

The Hanks et al article identifies eleven catalytic sub-domains containing pTK consensus residues and sequences. The pTKs of the present invention will have most or all of these consensus residues and sequences.

Some particularly strongly conserved residues and sequences are shown in Table 1.

TABLE 1

| Conserved Residues and Sequences in pTKs[1] | | |
|---|---|---|
| Position[2] | Residue or Sequence | Catalytic Domain |
| 50 | G | I |
| 52 | G | I |
| 57 | V | I |
| 70 | A | II |
| 72 | K | II |
| 91 | E | III |
| 166 | D | VI |
| 171 | N | VI |
| 184–186 | DFG | VII |
| 208 | E | VIII |
| 220 | D | IX |
| 225 | G | IX |
| 280 | R | XI |

1. See Hanks et al., Science 241, 42–52 (1988)
2. Adjusted in accordance with Hanks et al., Id.

A pTK of the invention may contain all thirteen of these highly conserved residues and sequences. As a result of natural or synthetic mutations, the pTKs of the invention may contain fewer than all thirteen strongly conserved residues and sequences, such as 11, 9, or 7 such sequences.

The receptors of the invention generally belong to the same class of pTK sequences that c-kit belongs to. It has surprisingly been discovered, however, that a new functional class of receptor pTKs exists. The new functional class of receptor pTKs is expressed in primitive hematopoietic cells, but not expressed in mature hematopoietic cells.

For the purpose of this specification, a primitive hematopoietic cell is totipotent, i.e. capable of reconstituting all hematopoietic blood cells in vivo. A mature hematopoietic cell is non-self-renewing, and has limited proliferative capacity—i.e., a limited ability to give rise to multiple lineages. Mature hematopoietic cells, for the purposes of this specification, are generally capable of giving rise to only one or two lineages in vitro or in vivo.

It should be understood that the hematopoietic system is complex, and contains many intermediate cells between the primitive totipotent hematopoietic stem cell and the totally committed mature hematopoietic cells defined above. As the stem cell develops into increasingly mature, lineage-restricted cells, it gradually loses its capacity for self-renewal.

The receptors of the present invention may and may not be expressed in these intermediate cells. The necessary and sufficient condition that defines members of the new class of receptors is that they are present in the primitive, totipotent stem cell or cells, and not in mature cells restricted only to one or, at most, two lineages.

An example of a member of the new class of receptor pTKs is called fetal liver kinase 2 (flk-2) after the organ in which it was found. There is approximately 1 totipotent stem cell per $10^4$ cells in mid-gestation (day 14) fetal liver in mice. In addition to fetal liver, flk-2 is also expressed in fetal spleen, fetal thymus, adult brain, and adult marrow.

For example, flk-2 is expressed in individual multipotential CFU-Blast colonies capable of generating numerous multilineage colonies upon replating. It is likely, therefore, that flk-2 is expressed in the entire primitive (i.e. self-renewing) portion of the hematopoietic hierarchy. This discovery is consistent with flk-2 being important in transducing putative self-renewal signals from the environment.

It is particularly relevant that the expression of flk-2 mRNA occurs in the most primitive thymocyte subset. Even in two closely linked immature subsets that differ in expression of the IL-2 receptor, flk-2 expression segregates to the more primitive subset lacking an IL-2 receptor. The earliest thymocyte subset is believed to be uncommitted. Therefore, the thymocytes expressing flk-2 may be multipotential. flk-2 is the first receptor tyrosine kinase known to be expressed in the T-lymphoid lineage.

The fetal liver mRNA migrates relative to 28S and 18S ribosomal bands on formaldehyde agarose gels at approximately 3.5 kb, while the brain message is considerably larger. In adult tissues, flk-2 m-RNA from both brain and bone marrow migrated at approximately 3.5 kb.

A second pTK receptor is also included in the present invention. This second receptor, which is called fetal liver kinase 1 (flk-1), is not a member of the same class of receptors as flk-2, since flk-1 may be found in some more mature hematopoietic cells. The amino acid sequence of flk-1 is given in FIG. 2. (See SEQ. ID. NO. 6)

The present invention includes the flk-1 receptor as well as DNA, cDNA and RNA encoding flk-1. The DNA sequence of flk-1 is also given in FIG. 2. (See SEQ. ID. NO. 5) Flk-1 may be found in the same organs as flk-2, as well as in fetal brain, stomach, kidney, lung, heart and intestine; and in adult kidney, heart, spleen, lung, muscle, and lymph nodes.

The receptor protein tyrosine kinases of the invention are known to be divided into easily found domains. The DNA sequence corresponding to the pTKs encode, starting at their 5'-ends, a hydrophobic leader sequence followed by a hydrophilic extracellular domain, which binds to, and is activated by, a specific ligand. Immediately downstream from the extracellular receptor domain, is a hydrophobic transmembrane region. The transmembrane region is immediately followed by a basic catalytic domain, which may easily be identified by reference to the Hanks et al. and Wilks articles discussed above.

The present invention includes the extracellular receptor domain lacking the transmembrane region and catalytic domain. Preferably, the hydrophobic leader sequence is also removed from the extracellular domain. In the case of flk-2, the hydrophobic leader sequence includes amino acids 1–27. (See SEQ. ID. NOS. 2 and 4)

These regions and domains may easily be visually identified by those having ordinary skill in the art by reviewing the amino acid sequence in a suspected pTK and comparing it to known pTKs. For example, referring to FIG. 1A, the transmembrane region of flk-2, which separates the extracellular receptor domain from the catalytic domain, is encoded by nucleotides 1663 (T) to 1722 (C). These nucleotides correspond to amino acid residues 545 (Phe) to 564 (Cys) (See SEQ. ID. NOS. 1–2). The amino acid sequence between the transmembrane region and the catalytic subdomain (amino acids 618–623) identified by Hanks et al. as sub-domain I (i.e., GXGXXG) is characteristic of receptor protein tyrosine kinases.

The extracellular domain may also be identified through commonly recognized criteria of extracellular amino acid sequences. The determination of appropriate criteria is known to those skilled in the art, and has been described, for example, by Hopp et al, Proc. Nat'l Acad. Sci. U.S.A. 78, 3824–3828 (1981); Kyte et al, J. Mol. Biolo 157, 105–132 (1982); Emini, J. Virol. 55, 836–839 (1985); Jameson et al, CA BIOS 4, 181–186 (1988); and Karplus et al, Naturwissenschaften 72, 212–213 (1985). Amino acid domains predicted by these criteria to be surface exposed characteristic of extracellular domains.

As will be discussed in more detail below, the nucleic acid molecules that encode the receptors of the invention may be inserted into known vectors for use in standard recombinant DNA techniques. Standard recombinant DNA techniques are those such as are described in Sambrook et al , "Molecular Cloning," Second Edition, Cold Spring Harbor Laboratory Press (1987) and by Ausubel et al., Eds, "Current Protocols in Molecular Biology," Green Publishing Associates and Wiley-Interscience, New York (1987). The vectors may be circular (i.e. plasmids) or non-circular. Standard vectors are available for cloning and expression in a host. The host may be prokaryotic or eucaryotic. Prokaryotic hosts are preferably *E. coli*. Preferred eucaryotic hosts include yeast, insect and mammalian cells. Preferred mammalian cells include, for example, CHO, COS and human cells.

Ligands

The invention also includes ligands that bind to the receptor pTKs of the invention. In addition to binding, the ligands stimulate the proliferation of additional primitive stem cells, differentiation into more mature progenitor cells, or both.

The ligand may be a growth factor that occurs naturally in a mammal, preferably the same mammal that produces the corresponding receptor. The growth factor may be isolated and purified, or be present on the surface of an isolated population of cells, such as stromal cells.

The ligand may also be a molecule that does not occur naturally in a mammal. For example, antibodies, preferably monoclonal, raised against the receptors of the invention or against anti-ligand antibodies mimic the shape of, and act as, ligands if they constitute the negative image of the receptor or anti-ligand antibody binding site. The ligand may also be a non-protein molecule that acts as a ligand when it binds to, or otherwise comes into contact with, the receptor.

In another embodiment, nucleic acid molecules encoding the ligands of the invention are provided. The nucleic acid molecule may be RNA, DNA or cDNA.

Stimulating Proliferation of Stem Cells

The invention also includes a method of stimulating the proliferation and/or differentiation of primitive mammalian hematopoietic stem cells as defined above. The method comprises contacting the stem cells with a ligand in accordance with the present invention. The stimulation of proliferation and/or differentiation may occur in vitro or in vivo.

The ability of a ligand according to the invention to stimulate proliferation of stem cells in vitro and in vivo has important therapeutic applications. Such applications include treating mammals, including humans, whose primitive stem cells do not sufficiently undergo self-renewal. Example of such medical problems include those that occur when defects in hematopoietic stem cells or their related growth factors depress the number of white blood cells. Examples of such medical problems include anemia, such as macrocytic and aplastic anemia. Bone marrow damage resulting from cancer chemotherapy and radiation is another example of a medical problem that would be helped by the stem cell factors of the invention.

Functional Equivalents

The invention includes functional equivalents of the pTK receptors, receptor domains, and ligands described above as well as of the nucleic acid sequences encoding them. A protein is considered a functional equivalent of another protein for a specific function if the equivalent protein is immunologically cross-reactive with, and has the same function as, the receptors and ligands of the invention. The equivalent may, for example, be a fragment of the protein, or a substitution, addition or deletion mutant of the protein.

For example, it is possible to substitute amino acids in a sequence with equivalent amino acids. Groups of amino acids known normally to be equivalent are:

(a) Ala(A) Ser(S) Thr(T) Pro(P) Gly(G);

(b) Asn(N) Asp(D) Glu(E) Gln(Q);

(c) His(H) Arg(R) Lys(K);

(d) Met(M) Leu(L) Ile(I) Val(V); and (e) Phe(F) Tyr(Y) Trp(W).

Substitutions, additions and/or deletions in the receptors and ligands may be made as long as the resulting equivalent receptors and ligands are immunologically cross reactive with, and have the same function as, the native receptors and ligands.

The equivalent receptors and ligands will normally have substantially the same amino acid sequence as the native receptors and ligands. An amino acid sequence that is substantially the same as another sequence, but that differs from the other sequence by means of one or more substitutions, additions and/or deletions is considered to be an equivalent sequence. Preferably, less than 25%, more preferably less than 10%, and most preferably less than 5% of the number of amino acid residues in the amino acid sequence of the native receptors and ligands are substituted for, added to, or deleted from.

Equivalent nucleic acid molecules include nucleic acid sequences that encode equivalent receptors and ligands as defined above. Equivalent nucleic acid molecules also include nucleic acid sequences that differ from native nucleic acid sequences in ways that do not affect the corresponding amino acid sequences.

ISOLATION OF NUCLEIC ACID MOLECULES AND PROTEINS

Isolation of Nucleic Acid Molecules Encoding Receptors

In order to produce nucleic acid molecules encoding mammalian stem cell receptors, a source of stem cells is provided. Suitable sources include fetal liver, spleen, or thymus cells or adult marrow or brain cells.

For example, suitable mouse fetal liver cells may be obtained at day 14 of gestation. Mouse fetal thymus cells may be obtained at day 14–18, preferably day 15, of gestation. Suitable fetal cells of other mammals are obtained at gestation times corresponding to those of mouse.

Total RNA is prepared by standard procedures from stem cell receptor-containing tissue. The total RNA is used to direct cDNA synthesis. Standard methods for isolating RNA and synthesizing cDNA are provided in standard manuals of molecular biology such as, for example, in Sambrook et al, "Molecular Cloning," Second Edition, Cold Spring Harbor Laboratory Press (1987) and in Ausubel et al., (Eds), "Current Protocols in Molecular Biology," Greene Associates/ Wiley Interscience, New York (1990).

The cDNA of the receptors is amplified by known methods. For example, the cDNA may be used as a template for amplification by polymerase chain reaction (PCR); see Saiki et al., Science, 239, 487 (1988) or Mullis et al., U.S. Pat. No. 4,683,195. The sequences of the oligonucleotide primers for the PCR amplification are derived from the sequences of known receptors, such as from the sequences given in FIGS. 1A and 1B for flk-2 and in FIG. 2 for flk-1, respectively, preferably from flk-2 (See SEQ. ID. NOS. 1, 3 and 5, respectively). The oligonucleotides are synthesized by methods known in the art. Suitable methods include those described by Caruthers in Science 230, 281–285 (1985).

In order to isolate the entire protein-coding regions for the receptors of the invention, the upstream oligonucleotide is complementary to the sequence at the 5' end, preferably encompassing the ATG start codon and at least 5–10 nucleotides upstream of the start codon. The downstream oligonucleotide is complementary to the sequence at the 3' end, optionally encompassing the stop codon. A mixture of upstream and downstream oligonucleotides are used in the PCR amplification. The conditions are optimized for each particular primer pair according to standard procedures. The PCR product is analyzed by electrophoresis for the correct size cDNA corresponding to the sequence between the primers.

Alternatively, the coding region may be amplified in two or more overlapping fragments. The overlapping fragments are designed to include a restriction site permitting the assembly of the intact cDNA from the fragments.

The amplified DNA encoding the receptors of the invention may be replicated in a wide variety of cloning vectors in a wide variety of host cells. The host cell may be prokaryotic or eukaryotic. The DNA may be obtained from natural sources and, optionally, modified, or may be synthesized in whole or in part.

The vector into which the DNA is spliced may comprise segments of chromosomal, non-chromosomal and synthetic DNA sequences. Some suitable prokaryotic cloning vectors include plasmids from *E. coli*, such as colE1, pCR1, pBR322, pMB9, pUC, pKSM, and RP4. Prokaryotic vectors also include derivatives of phage DNA such as M13 and other filamentous single-stranded DNA phages.

Isolation of Receptors

DNA encoding the receptors of the invention are inserted into a suitable vector and expressed in a suitable prokaryotic or eucaryotic host. Vectors for expressing proteins in bacteria, especially *E. coli*, are known. Such vectors include the PATH vectors described by Dieckmann and Tzagoloff in J. Biol. Chem. 260, 1513–1520 (1985). These vectors contain DNA sequences that encode anthranilate synthetase (TrpE) followed by a polylinker at the carboxy terminus. Other expression vector systems are based on beta-galactosidase (pEX); lambda $P_L$; maltose binding protein (pMAL); and glutathione S-transferase (pGST)—see Gene 67, 31 (1988) and Peptide Research 3, 167 (1990).

Vectors useful in yeast are available. A suitable example is the 2u plasmid.

Suitable vectors for use in mammalian cells are also known. Such vectors include well-known derivatives of SV40, adenovirus, retrovirus-derived DNA sequences and shuttle vectors derived from combination of functional mammalian vectors, such as those described above, and functional plasmids and phage DNA.

Further eukaryotic expression vectors are known in the art (e.g., P. J. Southern and P. Berg, J. Mol. Appl. Genet. 1, 327–341 (1982); S. Subramani et al, Mol. Cell. Biol. 1, 854–864 (1981); R. J. Kaufmann and P. A. Sharp, "Amplification And Expression Of Sequences Cotransfected with A Modular Dihydrofolate Reductase Complementary DNA Gene," J. Mol. Biol. 159, 601–621 (1982); R. J. Kaufmann and P. A. Sharp, Mol. Cell. Biol. 159, 601–664 (1982); S. I. Scahill et al, "Expression And Characterization Of The Product Of A Human Immune Interferon DNA Gene In Chinese Hamster Ovary Cells," Proc. Natl. Acad. Sci. U.S.A. 80, 4654–4659 (1983); G. Urlaub and L. A. Chasin, Proc. Natl. Acad. Sci. U.S.A. 77, 4216–4220, (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Vectors containing the receptor-encoding DNA and control signals are inserted into a host cell for expression of the receptor. Some useful expression host cells include well-known prokaryotic and eukaryotic cells. Some suitable prokaryotic hosts include, for example, *E. coli*, such as *E. coli* SG-936, *E. coli* HB 101, *E. coli* W3110, *E. coli* X1776, *E. coli* X2282, *E. coli* DHI, and *E. coli* MRC1, Pseudomonas, Bacillus, such as *Bacillus subtilis*, and Streptomyces. Suitable eukaryotic cells include yeast and other fungi, insect, animal cells, such as COS cells and CHO cells, human cells and plant cells in tissue culture.

The human homologs of the mouse receptors described above are isolated by a similar strategy. RNA encoding the receptors are obtained from a source of human cells enriched for primitive stem cells. Suitable human cells include fetal spleen, thymus and liver cells, and umbilical cord blood as well as adult brain and bone marrow cells. The human fetal cells are preferably obtained on the day of gestation corresponding to mid-gestation in mice. The amino acid sequences of the human flk receptors as well as of the nucleic acid sequences encoding them are homologous to the amino acid and nucleotide sequences of the mouse receptors.

In the present specification, the sequence of a first protein, such as a receptor or a ligand, or of a nucleic acid molecule that encodes the protein, is considered homologous to a second protein or nucleic acid molecule if the amino acid or nucleotide sequence of the first protein or nucleic acid molecule is at least about 30% homologous, preferably at least about 50% homologous, and more preferably at least about 65% homologous to the respective sequences of the second protein or nucleic acid molecule. In the case of proteins having high homology, the amino acid or nucleotide sequence of the first protein or nucleic acid molecule is at least about 75% homologous, preferably at least about 85% homologous, and more preferably at least about 95% homologous to the amino acid or nucleotide sequence of the second protein or nucleic acid molecule.

Combinations of mouse oligonucleotide pairs are used as PCR primers to amplify the human homologs from the cells to account for sequence divergence. The remainder of the procedure for obtaining the human flk homologs are similar to those described above for obtaining mouse flk receptors. The less than perfect homology between the human flk homologs and the mouse oligonucleotides is taken into account in determining the stringency of the hybridization conditions.

Assay for expression of Receptors on Stem Cells

In order to demonstrate the expression of flk receptors on the surface of primitive hematopoietic stem cells, antibodies that recognize the receptor are raised. The receptor may be the entire protein as it exists in nature, or an antigenic fragment of the whole protein. Preferably, the fragment comprises the predicted extra-cellular portion of the molecule.

Antigenic fragments may be identified by methods known in the art. Fragments containing antigenic sequences may be selected on the basis of generally accepted criteria of potential antigenicity and/or exposure. Such criteria include the hydrophilicity and relative antigenic index, as determined by surface exposure analysis of proteins. The determination of appropriate criteria is known to those skilled in the art, and has been described, for example, by Hopp et al, Proc. Nat'l Acad. Sci. U.S.A. 78, 3824–3828 (1981); Kyte et al, J. Mol. Biol. 157, 105–132 (1982); Emini, J. Virol. 55, 836–839 (1985); Jameson et al, CA BIOS 4, 181–186 (1988); and Karplus et al, Naturwissenschaften 72, 212–213 (1985). Amino acid domains predicted by these criteria to be surface exposed are selected preferentially over domains predicted to be more hydrophobic or hidden.

The proteins and fragments of the receptors to be used as antigens may be prepared by methods known in the art. Such methods include isolating or synthesizing DNA encoding the proteins and fragments, and using the DNA to produce recombinant proteins, as described above.

Fragments of proteins and DNA encoding the fragments may be chemically synthesized by methods known in the art from individual amino acids and nucleotides. Suitable methods for synthesizing protein fragments are described by Stuart and Young in "Solid Phase Peptide Synthesis," Second Edition, Pierce Chemical Company (1984). Suitable methods for synthesizing DNA fragments are described by Caruthers in Science 230, 281–285 (1985).

If the receptor fragment defines the epitope, but is too short to be antigenic, it may be conjugated to a carrier molecule in order to produce antibodies. Some suitable carrier molecules include keyhole limpet hemocyanin, Ig sequences, TrpE, and human or bovine serum albumen. Conjugation may be carried out by methods known in the art. One such method is to combine a cysteine residue of the fragment with a cysteine residue on the carrier molecule.

The antibodies are preferably monoclonal. Monoclonal antibodies may be produced by methods known in the art. These methods include the immunological method described by Kohler and Milstein in Nature 256, 495–497 (1975) and Campbell in "Monoclonal Antibody Technology, The Production and Characterization of Rodent and Human Hybridomas" in Burdon et al., Eds, Laboratory Techniques in Biochemistry and Molecular Biology, Volume 13, Elsevier Science Publishers, Amsterdam (1985); as well as by the recombinant DNA method described by Huse et al in Science 246, 1275–1281 (1989).

Polyclonal or monoclonal antisera shown to be reactive with receptor-encoded native proteins, such as with flk-1 and flk-2 encoded proteins, expressed on the surface of viable cells are used to isolate antibody-positive cells. One method for isolating such cells is flow cytometry; see, for example, Loken et al., European patent application 317,156. The cells obtained are assayed for stem cells by engraftment into radiation-ablated hosts by methods known in the art; see, for example, Jordan et al., Cell 61, 953–963 (1990).

Criteria for Novel Stem Cell Receptor Tyrosine Kinases Expressed in Stem Cells

Additional novel receptor tyrosine kinase cDNAs are obtained by amplifying cDNAs from stem cell populations using oligonucleotides as PCR primers; see above. Examples of suitable oligonucleotides are PTK1 and PTK2, which were described by Wilks et al. in Proc. Natl. Acad. Sci. U.S.A. 86, 1603–1607 (1989). Novel cDNA is selected on the basis of differential hybridization screening with probes representing known kinases. The cDNA clones hybridizing only at low stringency are selected and sequenced. The presence of the amino acid triplet DFG confirms that the sequence represents a kinase. The diagnostic methionine residue in the WMAPES motif is indicative of a receptor-like kinase, as described above. Potentially novel sequences obtained are compared to available sequences using databases such as Genbank in order to confirm uniqueness. Gene-specific oligonucleotides are prepared as described above based on the sequence obtained. The oligonucleotides are used to analyze stem cell enriched and depleted populations for expression. Such cell populations in mice are described, for example, by Jordan et al. in Cell 61, 953–956 (1990); Ikuta et al. in Cell 62, 863–864 (1990); Spangrude et al. in Science 241, 58–62 (1988); and Szilvassy et al. in Blood 74, 930–939 (1989). Examples of such human cell populations are described as CD33$^-$CD34$^+$ by Andrews et al. in the Journal of Experimental Medicine 169, 1721–1731 (1989). Other human stem cell populations are described, for example, in Civin et al., European Patent Application 395,355 and in Loken et al., European Patent Application 317,156.

Isolating Ligands and Nucleic Acid Molecules Encoding Ligands

Cells that may be used for obtaining ligands include stromal cells, for example stromal cells from fetal liver, fetal spleen, fetal thymus and fetal or adult bone marrow. Cell lines expressing ligands are established and screened.

For example, cells such as stromal (non-hematopoietic) cells from fetal liver are immortalized by known methods. Examples of known methods of immortalizing cells include transduction with a temperature sensitive SV40 T-antigen expressed in a retroviral vector. Infection of fetal liver cells with this virus permits the rapid and efficient establishment of multiple independent cell lines. These lines are screened for ligand activity by methods known in the art, such as those outlined below.

Ligands for the receptors of the invention, such as flk-1 and flk-2, may be obtained from the cells in several ways. For example, a bioassay system for ligand activity employs chimeric tagged receptors; see, for example, Flanagan et al., Cell 63, 185–194 (1990). One strategy measures ligand binding directly via a histochemical assay. Fusion proteins comprising the extracellular receptor domains and secretable alkaline phosphatase (SEAP) are constructed and transfected into suitable cells such as NIH/3T3 or COS cells. Flanagan et al. refer to such DNA or amino acid constructs as APtag followed by the name of the receptor—i.e. APtag-c-kit. The fusion proteins bind with high affinity to cells expressing surface-bound ligand. Binding is detectable by the enzymatic activity of the alkaline phosphatase secreted into the medium. The bound cells, which are often stromal cells, are isolated from the APtag-receptor complex.

For example, some stromal cells that bind APtag-flk1 and APtag-flk2 fusion proteins include mouse fetal liver cells (see example 1); human fetal spleen cells (see example 3); and human fetal liver (example 3). Some stromal fetal thymus cells contain flk-1 ligand (example 3).

To clone the cDNA that encodes the ligand, a cDNA library is constructed from the isolated stromal cells in a suitable expression vector, preferably a phage such as CDMS, pSV Sport (BRL Gibco) or piH3, (Seed et al., Proc. Natl. Acad. Sci. U.S.A. 84, 3365–3369 (1987)). The library is transfected into suitable host cells, such as COS cells. Cells containing ligands on their surface are detected by known methods, see above.

In one such method, transfected COS cells are distributed into single cell suspensions and incubated with the secreted alkaline phosphatase-flk receptor fusion protein, which is present in the medium from NIH/3T3 or COS cells prepared by the method described by Flanagan et al., see above. Alkaline phosphatase-receptor fusion proteins that are not bound to the cells are removed by centrifugation, and the cells are panned on plates coated with antibodies to alkaline phosphatase. Bound cells are isolated following several washes with a suitable wash reagent, such as 5% fetal bovine serum in PBS, and the DNA is extracted from the cells. Additional details of the panning method described above may be found in an article by Seed et al., Proc. Natl. Acad. Sci. U.S.A. 84, 3365–3369 (1987).

In a second strategy, the putative extracellular ligand binding domains of the receptors are fused to the transmembrane and kinase domains of the human c-fms tyrosine kinase and introduced into 3T3 fibroblasts. The human c-fms kinase is necessary and sufficient to transduce proliferative signals in these cells after appropriate activation i.e. with the flk-1 or flk-2 ligand. The 3T3 cells expressing the chimeras are used to screen putative sources of ligand in a cell proliferation assay.

An alternate approach for isolating ligands using the fusion receptor-expressing 3T3 cells and insertional activation is also possible. A retrovirus is introduced into random chromosomal positions in a large population of these cells. In a small fraction, the retrovirus is inserted in the vicinity of the ligand-encoding gene, thereby activating it. These cells proliferate due to autocrine stimulation of the receptor. The ligand gene is "tagged" by the retrovirus, thus facilitating its isolation.

EXAMPLES

Example 1

Cells containing mouse flk-1 and flk-2 ligands. Murine stromal cell line 2018.

In order to establish stromal cell lines, fetal liver cells are disaggregated with collagen and grown in a mixture of Dulbecco's Modified Eagle's Medium (DMEM) and 10% heat-inactivated fetal calf serum at 37° C. The cells are immortalized by standard methods. A suitable method involves introducing DNA encoding a growth regulating- or oncogene-encoding sequence into the target host cell. The DNA may be introduced by means of transduction in a recombinant viral particle or transfection in a plasmid. See, for example, Hammerschmidt et al., Nature 340, 393–397 (1989) and Abcouwer et al, Biotechnology 7, 939–946 (1989). Retroviruses are the preferred viral vectors, although SV40 and Epstein-Barr virus can also serve as donors of the growth-enhancing sequences. A suitable retrovirus is the ecotropic retrovirus containing a temperature sensitive SV40 T-antigen (tsA58) and a G418 resistance gene described by McKay in Cell 66, 713–729 (1991). After several days at 37° C., the temperature of the medium is lowered to 32° C. Cells are selected with G418 (0.5 mg/ml). The selected cells are expanded and maintained.

A mouse stromal cell line produced by this procedure is called 2018 and was deposited on Oct. 30, 1991 in the American Type Culture Collection, Rockville, Md., U.S.A. (ATCC); accession number CRL 10907.

Example 2

Cells containing human flk-1 and flk-2 ligands.

Human fetal liver (18, 20, and 33 weeks after abortion), spleen (18 weeks after abortion), or thymus (20 weeks after abortion) is removed at the time of abortion and stored on ice in a balanced salt solution. After mincing into 1 mm fragments and forcing through a wire mesh, the tissue is washed one time in Hanks Balanced Salt Solution (HBSS).

The disrupted tissue is centrifuged at 200×g for 15 minutes at room temperature. The resulting pellet is resuspended in 10–20 ml of a tissue culture grade trypsin-EDTA solution (Flow Laboratories). The resuspended tissue is transferred to a sterile flask and stirred with a stirring bar at room temperature for 10 minutes. One ml of heat-inactivated fetal bovine calf serum (Hyclone) is added to a final concentration of 10% in order to inhibit trypsin activity. Collagenase type IV (Sigma) is added from a stock solution (10 mg/ml in HBSS) to a final concentration of 100 ug/ml in order to disrupt the stromal cells. The tissue is stirred at room temperature for an additional 2.5 hours; collected by centrifugation (400×g, 15 minutes); and resuspended in "stromal medium," which contains Iscove's modification of DMEM supplemented with 10% heat-inactivated fetal calf serum, 5% heat-inactivated human serum (Sigma), 4 mM L-glutamine, 1× sodium pyruvate, (stock of 100× Sigma), 1× non-essential amino acids (stock of 100×, Flow), and a mixture of antibiotics kanomycin, neomycin, penicillin, streptomycin. Prior to resuspending the pellet in the stromal medium, the pellet is washed one time with HBSS. It is convenient to suspend the cells in 60 ml of medium. The number of cultures depends on the amount of tissue.

Example 3

Isolating Stromal cells

Resuspended Cells (example 2) that are incubated at 37° C. with 5% carbon dioxide begin to adhere to the plastic plate within 10–48 hours. Confluent monolayers may be observed within 7–10 days, depending upon the number of cells plated in the initial innoculum. Non-adherent and highly refractile cells adhering to the stromal cell layer as colonies are separately removed by pipetting and frozen. Non-adherent cells are likely sources of populations of self-renewing stem cells containing flk-2. The adherent stromal cell layers are frozen in aliquots for future studies or expanded for growth in culture.

An unexpectedly high level of APtag-flk-2 fusion protein binding to the fetal spleen cells is observed. Two fetal spleen lines are grown in "stromal medium," which is described in example 2.

Non-adherent fetal stem cells attach to the stromal cells and form colonies (colony forming unit—CFU). Stromal cells and CFU are isolated by means of sterile glass cylinders and expanded in culture. A clone, called Fsp 62891, contains the flk-2 ligand. Fsp 62891 was deposited in the American Type Culture Collection, Rockville, Md., U.S.A on Nov. 21, 1991, accession number CRL 10935.

Fetal liver and fetal thymus cells are prepared in a similar way. Both of these cell types produce ligands of flk-1 and, in the case of liver, some flk-2. One such fetal thymus cell line, called F.thy 62891, and one such fetal liver cell line, called FL 62891, were deposited in the American Type Culture Collection, Rockville, Md., U.S.A on Nov. 21, 1991 and Apr. 2, 1992, respectively, accession numbers CRL 10936 and CRL 11005, respectively.

Stable human cell lines are prepared from fetal cells with the same temperature sensitive immortalizing virus used to prepare the murine cell line described in example 1.

Example 4

Isolation of human stromal cell clone

Highly refractile cells overgrow patches of stromal cells, presumably because the stromal cells produce factors that allow the formation of the CFU. To isolate stromal cell clones, sterile glass cylinders coated with vacuum grease are positioned over the CFU. A trypsin-EDTA solution (100 ml) is added in order to detach the cells. The cells are added to 5 ml of stromal medium and each (clone) plated in a single well of 6-well plate.

Example 5

Plasmid (AP-tag) for expressing secretable alkaline phosphatase (SEAP)

Plasmids that express secretable alkaline phosphatase are described by Flanagan and Leder in Cell 63, 185–194 (1990). The plasmids contain a promoter, such as the LTR promoter; a polylinker, including HindIII and BglII; DNA encoding SEAP; a poly-A signal; and ampicillin resistance gene; and replication site.

Example 6

Plasmid for expressing APtag-flk-2 and APtag-flk-1 fusion proteins

Plasmids that express fusion proteins of SEAP and the extracellular portion of either flk-1 or flk-2 are prepared in accordance with the protocols of Flanagan and Leder in Cell 53, 185–194 (1990) and Berger et al., Gene 66, 1–10 (1988). Briefly, a HindIII-Bam HI fragment containing the extracellular portion of flk-1 or flk-2 is prepared and inserted into the HindIII-BglII site of the plasmid described in example 5.

Example 7

Production Of APtaq-flk-1 Or -flk-2 Fusion Protein

The plasmids from Example 6 are transfected into Cos-7 cells by DEAE-dextran (as described in Current Protocols in Molecular Biology, Unit 16.13, "Transient Expression of Proteins Using Cos Cells," 1991); and cotransfected with a selectable marker, such as pSV7neo, into NIH/3T3 cells by calcium precipitation. The NIH/3T3 cells are selected with 600 μg/ml G418 in 100 mm plates. Over 300 clones are screened for secretion of placental alkaline phosphatase activity. The assay is performed by heating a portion of the supernatant at 65° C. for 10 minutes to inactivate background phosphatase activity, and measuring the $OD_{405}$ after incubating with 1M diethanolamine (pH 9.8), 0.5 mM $MgCl_2$, 10 mM L-homoarginine (a phosphatase inhibitor), 0.5 mg/ml BSA, and 12 mM p-nitrophenyl phosphate. Human placental alkaline phosphatase is used to perform a standard curve. The APtaq-flk-1 clones (F-1AP21-4) produce up to 10 μg alkaline phosphatase activity/ml and the APtaq-flk-2 clones (F-2AP26-0) produce up to 0.5 μg alkaline phosphatase activity/ml.

Example 8

Assay For APtaq-flk-1 Or APtaq-flk-2 Binding To Cells

The binding of APtaq-flk-1 or APtag-flk-2 to cells containing the appropriate ligand is assayed by standard methods. See, for example, Flanagan and Leder, Cell 63:185–194, 1990). Cells (i.e., mouse stromal cells, human fetal liver, spleen or thymus, or various control cells) are grown to confluency in six-well plates and washed with HBHA (Hank's balanced salt solution with 0.5 mg/ml BSA, 0.02% $NaN_3$, 20 mM HEPES, pH 7.0). Supernatants from transfected COS or NIH/3T3 cells containing either APtaq-flk-1 fusion protein, APtag-flk-2 fusion protein, or APtag without a receptor (as a control) are added to the cell monolayers and incubated for two hours at room temperature on a rotating platform. The concentration of the APtaq-flk-1 fusion protein, APtag-flk-2 fusion protein, or APtag without a receptor is 60 ng/ml of alkaline phosphatase as determined by the standard alkaline phosphatase curve (see above). The cells are then rinsed seven times with HBHA and lysed in 350 μl of 1% Triton X-100, 10 mM Tris-HCl (pH 8.0). The lysates are transferred to a microfuge tube, along with a further 150 μl rinse with the same solution. After vortexing vigorously, the samples are centrifuged for five minutes in a microfuge, heated at 65° C. for 12 minutes to inactivate cellular phosphatases, and assayed for phosphatase activity as described previously. Results of experiments designed to show the time and dose responses of binding between stromal cells containing the ligands to flk-2 and flk-1 (2018) and APtag-flk-2, APtag-flk-1 and APtag without receptor (as a control) are shown in FIGS. 3 and 4, respectively.

Example 8A

Plasmids for expressing flk1/fms and flk2/fms fusion proteins

Plasmids that express fusion proteins of the extracellular portion of either flk-1 or flk-2 and the intracellular portion of c-fms (also known as colony-stimulating factor-1 receptor) are prepared in a manner similar to that described under Example 6 (Plasmid for expressing APtag-flk-2 and APtag-flk-1 fusion proteins). Briefly, a Hind III-Bam HI fragment containing the extracellular portion of flk1 or flk2 is prepared and inserted into the Hind III-Bgl II site of a pLH expression vector containing the intracellular portion of c-fms.

8B. Expression of flk1/fms or flk2/fms in 3T3 cells

The plasmids from Example 11 are transfected into NIH/3T3 cells by calcium. The intracellular portion of c-fms is detected by Western blotting.

Example 9

Cloning and Expression of cDNA Coding For Mouse Ligand To flk-1 and flk-2 Receptors cDNA expressing mouse ligand for flk-1 and flk-2 is prepared by known methods. See, for example, Seed, B., and Aruffo, A. PNAS 84:3365–3369, 1987; Simmons, D. and Seed, B. J. Immunol. 141:2797–2800; and D'Andrea, A. D., Lodish, H. F. and Wong, G. G. Cell 57:277–285, 1989).

The protocols are listed below in sequence: (a) RNA isolation; (b) poly A RNA preparation; (c) cDNA synthesis; (d) cDNA size fractionation; (e) propagation of plasmids (vector); (f) isolation of plasmid DNA; (g) preparation of vector pSV Sport (BRL Gibco) for cloning; (h) compilation of buffers for the above steps; (i) Transfection of cDNA encoding Ligands in Cos 7 Cells; (j) panning procedure; (k) Expression cloning of flk-1 or flk-2 ligand by establishment of an autocrine loop.

9a. Guanidinium thiocyanate/LiCl Protocol for RNA Isolation

For each ml of mix desired, 0.5 g guanidine thiocyanate (GuSCN) is dissolved in 0.55 ml of 25% LiCl (stock filtered through 0.45 micron filter). 20 μl of mercaptoethanol is added. (The resulting solution is not good for more than about a week at room temperature.)

The 2018 stromal cells are centrifuged, and 1 ml of the solution described above is added to up to $5 \times 10^7$ cells. The cells are sheared by means of a polytron until the mixture is non-viscous. For small scale preparations ($<10^8$ cells), the sheared mixture is layered on 1.5 ml of 5.7M CsCl (RNase free; 1.26 g CsCl added to every ml 10 mM EDTA pH8), and overlaid with RNase-free water if needed. The mixture is spun in an SW55 rotor at 50 krpm for 2 hours. For large scale preparations, 25 ml of the mixture is layered on 12 ml CsCl in an SW28 tube, overlaid as above, and spun at 24 krpm for 8 hours. The contents of the tube are aspirated carefully with a sterile pasteur pipet connected to a vacuum flask. Once past the CsCl interface, a band around the tube is scratched with the pipet tip to prevent creeping of the layer on the wall down the tube. The remaining CsCl solution is aspirated. The resulting pellet is taken up in water, but not redissolved. 1/10 volume of sodium acetate and three volumes of ethanol are added to the mixture, and spun. The pellet is resuspended in water at 70° C., if necessary. The concentration of the RNA is adjusted to 1 mg/ml and frozen.

It should be noted that small RNA molecules (e.g., 5S) do not come down. For small amounts of cells, the volumes are scaled down, and the mixture is overlaid with GuSCN in RNase-free water on a gradient (precipitation is inefficient when RNA is dilute).

9b. Poly A⁻ RNA preparation (All buffers mentioned are compiled separately below)

A disposable polypropylene column is prepared by washing with 5M NaOH and then rinsing with RNase-free water. For each milligram of total RNA, approximately 0.3 ml (final packed bed) of oligo dT cellulose is added. The oligo dT cellulose is prepared by resuspending approximately 0.5 ml of dry powder in 1 ml of 0.1M NaOH and transferring it into the column, or by percolating 0.1M NaOH through a previously used column. The column is washed with several column volumes of RNase-free water until the pH is neutral, and rinsed with 2–3 ml of loading buffer. The column bed is transferred to a sterile 15 ml tube using 4–6 ml of loading buffer.

Total RNA from the 2018 cell line is heated to 70° C. for 2–3 minutes. LiCl from RNase-free stock is added to the mixture to a final concentration of 0.5M. The mixture is combined with oligo dT cellulose in the 15 ml tube, which is vortexed or agitated for 10 minutes. The mixture is poured into the column, and washed with 3 ml loading buffer, and then with 3 ml of middle wash buffer. The mRNA is eluted directly into an SW55 tube with 1.5 ml of 2 mM EDTA and 0.1% SDS, discarding the first two or three drops.

The eluted mRNA is precipitated by adding 1/10 volume of 3M sodium acetate and filling the tube with ethanol. The contents of the tube are mixed, chilled for 30 minutes at −20° C., and spun at 50 krpm at 5° C. for 30 minutes. After the ethanol is decanted, and the tube air dried, the mRNA pellet is resuspended in 50–100 µl of RNase-free water. 5 µl of the resuspended mRNA is heated to 70° C. in MOPS/EDTA/formaldehyde, and examined on an RNase-free 1% agarose gel.

9c. cDNA Synthesis

The protocol used is a variation of the method described by Gubler and Hoffman in Gene 25, 263–270 (1983).

1. First Strand. 4 µg of mRNA is added to a microfuge tube, heated to approximately 100° C. for 30 seconds, quenched on ice. The volume is adjusted to 70 µl with RNAse-free water. 20 µl of RT1 buffer, 2 µl of RNAse inhibitor (Boehringer 36 u/µl), 1 µl of 5 µg/µl of oligo dT (Collaborative Research), 2.5 µl of 20 mM dXTP's (ultrapure—US Biochemicals), 1 µl of 1M DTT and 4 µl of RT-XL (Life Sciences, 24 u/µl) are added. The mixture is incubated at 42° C. for 40 minutes, and inactivated by heating at 70° C. for 10 minutes.

2. Second Strand. 320 µl of RNAse-free water, 80 µl of RT2 buffer, 5 µl of DNA Polymerase I (Boehringer, 5 U/µl), 2 µl RNAse H (BRL 2 u/µl) are added to the solution containing the first strand. The solution is incubated at 15° C. for one hour and at 22° C. for an additional hour. After adding 20 µl of 0.5M EDTA, pH 8.0, the solution is extracted with phenol and precipitated by adding NaCl to 0.5M linear polyacrylamide (carrier) to 20 µg/ml, and filling the tube with EtOH. The tube is spun for 2–3 minutes in a microfuge, vortexed to dislodge precipitated material from the wall of the tube, and respun for one minute.

3. Adaptors. Adaptors provide specific restriction sites to facilitate cloning, and are available from BRL Gibco, New England Biolabs, etc. Crude adaptors are resuspended at a concentration of 1 µg/µl. MgSO$_4$ is added to a final concentration of 10 mM, followed by five volumes of EtOH. The resulting precipitate is rinsed with 70% EtOH and resuspended in TE at a concentration of 1 µg/µl. To kinase, 25 µl of resuspended adaptors is added to 3 µl of 10× kinasing buffer and 20 units of kinase. The mixture is incubated at 37° C. overnight. The precipitated cDNA is resuspended in 240 µl of TE (10/1). After adding 30 µl of 10× low salt buffer, 30 µl of 10× ligation buffer with 0.1 mM ATP, 3 µl (2.4 µg) of kinased 12-mer adaptor sequence, 2 µl (1.6 µg) of kinased 8-mer adaptor sequence, and 1 µl of T4 DNA ligase (BioLabs, 400 u/µl, or Boehringer, 1 Weiss unit ml), the mixture is incubated at 15° C. overnight. The cDNA is extracted with phenol and precipitated as above, except that the extra carrier is omitted, and resuspended in 100 µl of TE.

9d. cDNA Size Fractionation.

A 20% KOAc, 2 mM EDTA, 1 µg/ml ethidium bromide solution and a 5% KOAc, 2 mM EDTA, 1 µg/ml ethidium bromide solution are prepared. 2.6 ml of the 20% KOAc solution is added to the back chamber of a small gradient maker. Air bubbles are removed from the tube connecting the two chambers by allowing the 20% solution to flow into the front chamber and forcing the solution to return to the back chamber by tilting the gradient maker. The passage between the chambers is closed, and 2.5 ml of 5% solution is added to the front chamber. Any liquid in the tubing from a previous run is removed by allowing the 5% solution to flow to the end of the tubing, and then to return to its chamber. The apparatus is placed on a stirplate, and, with rapid stirring, the topcock connecting the two chambers and the front stopcock are opened. A polyallomer 5W55 tube is filled from the bottom with the KOAc solution. The gradient is overlaid with 100 µl of cDNA solution, and spun for three hours at 50 k rpm at 22° C. To collect fractions from the gradient, the SW55 tube is pierced close to the bottom of the tube with a butterfly infusion set (with the luer hub clipped off). Three 0.5 ml fractions and then six 0.25 ml fractions are collected in microfuge tubes (approximately 22 and 11 drops, respectively). The fractions are precipitated by adding linear polyacrylamide to 20 µg/ml and filling the tube to the top with ethanol. The tubes are cooled, spun in a microfuge tube for three minutes, vortexed, and respun for one minute. The resulting pellets are rinsed with 70% ethanol and respun, taking care not to permit the pellets to dry to completion. Each 0.25 ml fraction is resuspended in 10 µl of TE, and 1 µl is run on a 1% agarose minigel. The first three fractions, and the last six which contain no material smaller than 1 kb are pooled.

9e. Propagation of Plasmids

SupF plasmids are selected in nonsuppressing bacterial hosts containing a second plasmid, p3, which contains amber mutated ampicillin and tetracycline drug resistance elements. See Seed, Nucleic Acids Res., 11, 2427–2445 (1983). The p3 plasmid is derived from RP1, is 57 kb in length, and is a stably maintained, single copy episome. The ampicillin resistance of this plasmid reverts at a high rate so that amp$^r$ plasmids usually cannot be used in p3-containing strains. Selection for tetracycline resistance alone is almost as good as selection for ampicillin-tetracycline resistance. However, spontaneous appearance of chromosomal suppressor tRNA mutations presents an unavoidable background (frequency about $10^{-9}$) in this system. Colonies arising from spontaneous suppressor mutations are usually larger than colonies arising from plasmid transformation. Suppressor plasmids are selected in Luria broth (LB) medium containing ampicillin at 12.5 µg/ml and tetracycline at 7.5 µg/ml. For scaled-up plasmid preparations, M9 Casamino acids medium containing glycerol (0.8%) is employed as a carbon source. The bacteria are grown to saturation.

Alternatively, pSV Sport (BRL, Gaithersberg, Md.) may be employed to provide SV40 derived sequences for replication, transcription initiation and termination in COS 7 cells, as well as those sequences necessary for replication and ampicillin resistance in E. coli.

9f. Isolation of Vector DNA/Plasmid

One liter of saturated bacterial cells are spun down in J6 bottles at 4.2 k rpm for 25 minutes. The cells are resuspended in 40 ml 10 mM EDTA, pH 8. 80 ml 0.2M NaOH and 1% SDS are added, and the mixture is swirled until it is clear and viscous. 40 ml 5M KOAc, pH 4.7 (2.5M KOAc, 2.5M HOAc) is added, and the mixture is shaken semivigorously until the lumps are approximately 2–3 mm in size. The bottle is spun at 4.2 k rpm for 5 minutes. The supernatant is poured through cheesecloth into a 250 ml bottle, which is then filled with isopropyl alcohol and centrifuged at 4.2 k rpm for 5 minutes. The bottle is gently drained and rinsed with 70% ethanol, taking care not to fragment the pellet. After inverting the bottle and removing traces of ethanol, the mixture is resuspended in 3.5 ml Tris base/EDTA (20 mM/10 mM). 3.75 ml of resuspended pellet and 0.75 ml 10 mg/ml ethidium bromide are added to 4.5 g CsCl. VTi80 tubes are filled with solution, and centrifuged for at least 2.5 hours at 80 k rpm. Bands are extracted by visible light with 1 ml syringe and 20 gauge or lower needle. The top of the tube is cut off with scissors, and the needle is inserted upwards into the tube at an angle of about 30 degrees with respect to the tube at a position about 3 mm beneath the band, with the bevel of the needle up. After the band is removed, the contents of the tube are poured into bleach. The extracted band is deposited in a 13 ml Sarstedt tube, which is then filled to the top with n-butanol saturated with 1M NaCl extract. If the amount of DNA is large, the extraction procedure may be repeated. After aspirating the butanol into a trap containing 5M NaOH to destroy ethidium, an approximately equal volume of 1M ammonium acetate and approximately two volumes of 95% ethanol are added to the DNA, which is then spun at 10 k rpm for 5 minutes. The pellet is rinsed carefully with 70% ethanol, and dried with a swab or lyophilizer.

9g. Preparation of Vector for Cloning

20 μg of vector is cut in a 200 μl reaction with 100 units of BstXI (New York Biolabs) at 50° C. overnight in a well thermostated, circulating water bath. Potassium acetate solutions (5 and 20%) are prepared in 5W55 tubes as described above. 100 μl of the digested vector is added to each tube and spun for three hours, 50 k rpm at 22° C. Under 300 nm UV light, the desired band is observed to migrate ⅔ of the length of the tube. Forward trailing of the band indicates that the gradient is overloaded. The band is removed with a 1 ml syringe fitted with a 20 gauge needle. After adding linear polyacrylamide and precipitating the plasmid by adding three volumes of ethanol, the plasmid is resuspended in 50 μl of TE. Trial ligations are carried out with a constant amount of vector and increasing amounts of cDNA. Large scale ligation are carried out on the basis of these trial ligations. Usually the entire cDNA prep requires 1–2 μg of cut vector.

9h. Buffers

| Loading Buffer: | .5M LiCl, 10 mM Tris pH 7.5, 1 mM EDTA .1% SDS. |
|---|---|
| Middle Wash Buffer: | .15M LiCl, 10 mM Tris pH 7.5, 1 mM EDTA .1% SDS. |
| RT1 Buffer: | .25M Tris pH 8.8 (8.2 at 42⁻), .25M KCl, 30 mM MgCl$_2$. |
| RT2 Buffer: | .1M Tris pH 7.5, 25 mM MgCl2, .5M KCl, .25 mg/ml BSA, 50 mM dithiothreitol (DTT). |
| 10 X Low Salt: | 60 mM Tris pH 7.5, 60 mM MgCl$_2$, 50 mM NaCl, 2.5 mg/ml BSA 70 mM DME |
| 10 X Ligation Additions: | 1 mM ATP, 20 mM DTT, 1 mg/ml BSA 10 mM spermidine. |
| 10 X Kinasing Buffer: | .5M Tris pH 7.5, 10 mM ATP, 20 mM DTT, 10 mM spermidine, 1 mg/ml BSA 100 mM MgCl$_2$ |

9i. Transfection of cDNA encoding Ligands in Cos 7 Cells

Cos 7 cells are split 1:5 into 100 mm plates in Dulbecco's modified Eagles medium (DME)/10% fetal calf serum (FCS), and allowed to grow overnight. 3 ml Tris/DME (0.039M Tris, pH 7.4 in DME) containing 400 μg/ml DEAE-dextran (Sigma, D-9885) is prepared for each 100 mm plate of Cos 7 cells to be transfected. 10 ug of plasmid DNA preparation per plate is added. The medium is removed from the Cos-7 cells and the DNA/DEAE-dextran mixture is added. The cells are incubated for 4.5 hours. The medium is removed from the cells, and replaced with 3 ml of DME containing 2% fetal calf serum (FCS) and 0.1 mM chloroquine. The cells are incubated for one hour. After removing the chloroquine and replacing with 1.5 ml 20% glycerol in PBS, the cells are allowed to stand at room temperature for one minute. 3 ml Tris/DME is added, and the mixture is aspirated and washed two times with Tris/DME. 10 ml DME/10% FCS is added and the mixture is incubated overnight. The transfected Cos 7 cells are split 1:2 into fresh 100 mm plates with (DME)/10% FCS and allowed to grow.

9j. Panning Procedure for Cos 7 cells Expressing Ligand

1) Antibody-coated plates:

Bacteriological 100 mm plates are coated for 1.5 hours with rabbit anti-human placental alkaline phosphatase (Dako, Calif.) diluted 1:500 in 10 ml of 50 mM Tris.HCl, pH 9.5. The plates are washed three times with 0.15M NaCl, and incubated with 3 mg BSA/ml PBS overnight. The blocking solution is aspirated, and the plates are utilized immediately or frozen for later use.

2) Panning cells:

The medium from transfected Cos 7 cells is aspirated, and 3 ml PBS/0.5 mM EDTA/0.02% sodium azide is added. The plates are incubated at 37° C. for thirty minutes in order to detach the cells. The cells are triturated vigorously with a pasteur pipet and collected in a 15 ml centrifuge tube. The plate is washed with a further 2 ml PBS/EDTA/azide solution, which is then added to the centrifuge tube. After centrifuging at 200×g for five minutes, the cells are resuspended in 3 ml of APtaq-flk-1 (F-1AP21-4) or flk-2 (F-2AP26-0) supernatant from transfected NIH/3T3 cells (see Example 7.), and incubated for 1.5 hours on ice. The cells are centrifuged again at 200×g for five minutes. The supernatant is aspirated, and the cells are resuspended in 3 ml PBS/EDTA/azide solution. The cell suspension is layered carefully on 3 ml PBS/EDTA/azide/2% Ficoll, and centrifuged at 200×g for four minutes. The supernatant is aspirated, and the cells are resuspended in 0.5 ml PBS/EDTA/azide solution. The cells are added to the antibody-coated plates containing 4 ml PBS/EDTA/azide/5% FBS, and allowed to stand at room temperature one to three hours. Non-adhering cells are removed by washing gently two or three times with 3 ml PBS/5% FBS.

3) Hirt Supernatant:

0.4 ml 0.6% SDS and 10 mM EDTA are added to the panned plates, which are allowed to stand 20 minutes. The viscous mixture is added by means of a pipet into a microfuge tube. 0.1 ml 5M NaCl is added to the tube, mixed, and chilled on ice for at least five hours. The tube is spun for four minutes, and the supernatant is removed carefully. The contents of the tube are extracted with phenol once, or, if the first interface is not clean, twice. Ten micrograms of linear polyacrylamide (or other carrier) is added, and the tube is filled to the top with ethanol. The resulting precipitate is resuspended in 0.1 ml water or TE. After adding 3 volumes of EtOH/NaOAc, the cells are reprecipitated and resuspended in 0.1 ml water or TE. The cDNA obtained is transfected into any suitable *E. coli* host by electroporation. Suitable hosts are described in various catalogs, and include MC1061/p3 or Electromax DH10B Cells of BRL Gibco. The cDNA is extracted by conventional methods.

The above panning procedure is repeated until a pure *E. coli* clone bearing the cDNA as a unique plasmid recombinant capable of transfecting mammalian cells and yielding a positive panning assay is isolated. Normally, three repetitions are sufficient.

9k. Expression cloning of flk1 or flk2 ligand by establishment of an autocrine loop Cells expressing flk1/fms or flk2/fms (Example 10) are transfected with 20–30 ug of a cDNA library from either flk1 ligand or flk2 ligand expressing stromal cells, respectively. The cDNA library is prepared as described above (a–h). The cells are co-transfected with 1 ug pLTR neo cDNA. Following transfection the cells are passaged 1:2 and cultured in 800 ug/ml of G418 in Dulbecco's medium (DME) supplemented with 10% CS. Approximately 12 days later the colonies of cells are passaged and plated onto dishes coated with poly-D-lysine (1 mg/ml) and human fibronectin (15 ug/ml). The culture medium is defined serum-free medium which is a mixture (3:1) of DME and Ham's F12 medium. The medium supplements are 8 mM NaHCO$_3$, 15 mM HEPES pH 7.4, 3 mM histidine, 4 uM MnCl$_2$, 10 uM ethanolamine, 0.1 uM selenous acid, 2 uM hydrocortisone, 5 ug/ml transferrin, 500 ug/ml bovine serum albumin/linoleic acid complex, and 20 ug/ml insulin (Ref. Zhan, X, et al. Oncogene 1: 369–376,1987). The cultures are refed the next day and every 3 days until the only cells capable of growing under the defined medium condition remain. The remaining colonies of cells are expanded and tested for the presence of the ligand by assaying for binding of APtag-flk1 or APtag-flk2 to the cells (as described in Example 8). The DNA would be rescued from cells demonstrating the presence of the flk1 or flk2 ligand and the sequence.

Example 10

Expression of Ligand cDNA

The cDNA is sequenced, and expressed in a suitable host cell, such as a mammalian cell, preferably COS, CHO or NIH/3T3 cells. The presence of the ligand is confirmed by demonstrating binding of the ligand to APtag-flk2 fusion protein (see above).

Example 11

Chemical Cross Linking of Receptor and Ligand

Cross linking experiments are performed on intact cells using a modification of the procedure described by Blume-Jensen et al et al., EMBO J., 10, 4121–4128 (1991). Cells are cultured in 100 mm tissue culture plates to subconfluence and washed once with PBS-0.1% BSA.

To examine chemical cross linking of soluble receptor to membrane-bound ligand, stromal cells from the 2018 stromal cell line are incubated with conditioned media (CM) from transfected 3T3 cells expressing the soluble receptor Flk2-APtag. Cross linking studies of soluble ligand to membrane bound receptor are performed by incubating conditioned media from 2018 cells with transfected 3T3 cells expressing a Flk2-fms fusion construct.

Binding is carried out for 2 hours either at room temperature with CM containing 0.02% sodium azide to prevent receptor internalization or at 4° C. with CM (and buffers) supplemented with sodium vanadate to prevent receptor dephosphorylation. Cells are washed twice with PBS-0.1% BSA and four times with PBS.

Cross linking is performed in PBS containing 250 mM disuccinimidyl suberate (DSS; Pierce) for 30 minutes at room temperature. The reaction is quenched with Tris-HCL pH7.4 to a final concentration of 50 mM.

Cells are solubilized in solubilization buffer: 0.5% Triton-X100, 0.5% deoxycholic acid, 20 mM Tris pH 7.4, 150 mM NaCl, 10 mM EDTA, 1 mM PMFS, 50 mg/ml aprotinin, 2 mg/ml bestatin, 2 mg/ml pepstatin and 10 mg/ml leupeptin. Lysed cells are immediately transferred to 1.5 ml Nalgene tubes and solubilized by rolling end to end for 45 minutes at 4° C. Lysates are then centrifuged in a microfuge at 14,000 g for 10 minutes. Solubilized cross linked receptor complexes are then retrieved from lysates by incubating supernatants with 10% (v/v) wheat germ lectin-Sepharose 6MB beads (Pharmacia) at 4° C. for 2 hours or overnight.

Beads are washed once with Tris-buffered saline (TBS) and resuspended in 2× SDS-polyacrylamide nonreducing sample buffer. Bound complexes are eluted from the beads by heating at 95° C. for 5 minutes. Samples are analyzed on 4–12% gradient gels (NOVEX) under nonreducing and reducing conditions (0.35M 2-mercaptoethanol) and then transferred to PVDF membranes for 2 hours using a Novex blotting apparatus. Blots are blocked in TBS-3% BSA for 1 hour at room temperature followed by incubation with appropriate antibody.

Cross linked Flk2-APtag and Flk2-fms receptors are detected using rabbit polyclonal antibodies raised against human alkaline phosphatase and fms protein, respectively. The remainder of the procedure is carried out according to the instructions provided in the ABC Kit (Pierce). The kit is based on the use of a biotinylated secondary antibody and avidin-biotinylated horseradish peroxidase complex for detection.

SUPPLEMENTAL ENABLEMENT

The invention as claimed is enabled in accordance with the above specification and readily available references and starting materials. Nevertheless, Applicants have deposited with the American Type Culture Collection, Rockville, Md., U.S.A. (ATCC) the cell lines listed below:

2018, ATCC accession no. CRL 10907, deposited Oct. 30, 1991.

Fsp 62891, ATCC accession no. CRL 10935, deposited Nov. 21, 1991.

F.thy 62891, ATCC accession no. CRL 10936, deposited Nov. 21, 1991.

FL 62891, ATCC accession no. CRL 11005, deposited Apr. 2, 1992.

These deposits were made under the provisions of the Budapest Treaty on the International Recognition of the Deposit of Microorganisms for the Purposes of Patent Procedure and the regulations thereunder (Budapest Treaty). This assures maintenance of a viable culture for 30 years from date of deposit. The organisms will be made available by ATCC under the terms of the Budapest Treaty, and subject to an agreement between Applicants and ATCC which assures unrestricted availability upon issuance of the pertinent U.S. patent. Availability of the deposited strains is not to be construed as a license to practice the invention in contravention of the rights granted under the authority of any government in accordance with its patent laws.

What is claim is:

1. A recombinant nucleic acid molecule that encodes a protein comprising the extracellular domain of human flk-2 having the sequence shown in FIG. 1B and in SEQ. ID. NO. 3, wherein the protein lacks the flk-2 intracellular catalytic domain.

2. An isolated mRNA that encodes a protein comprising the extracellular domain of human flk-2 having the sequence shown in FIG. 1B and in SEQ. ID. NO. 3, wherein the protein lacks the flk-2 intracellular catalytic domain.

* * * * *